United States Patent
Gremyachinskiy et al.

(10) Patent No.: US 10,975,432 B2
(45) Date of Patent: Apr. 13, 2021

(54) TAGGED MULTI-NUCLEOTIDES USEFUL FOR NUCLEIC ACID SEQUENCING

(71) Applicant: Roche Sequencing Solutions, Inc., Pleasanton, CA (US)

(72) Inventors: Dmitriy Gremyachinskiy, San Francisco, CA (US); Meng Taing, Hayward, CA (US); Aruna Ayer, Santa Clara, CA (US); Peter J. Crisalli, Mountain View, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 0 days.

(21) Appl. No.: 16/822,802

(22) Filed: Mar. 18, 2020

(65) Prior Publication Data

US 2020/0263248 A1    Aug. 20, 2020

Related U.S. Application Data

(63) Continuation of application No. 15/604,611, filed on May 24, 2017, now Pat. No. 10,655,174.

(60) Provisional application No. 62/342,796, filed on May 27, 2016.

(51) Int. Cl.
| C12Q 1/68 | (2018.01) |
| C12Q 1/6874 | (2018.01) |
| C07H 19/10 | (2006.01) |
| G01N 27/447 | (2006.01) |
| G01N 33/487 | (2006.01) |

(52) U.S. Cl.
CPC .......... *C12Q 1/6874* (2013.01); *C07H 19/10* (2013.01); *G01N 27/44791* (2013.01); *G01N 33/48721* (2013.01)

(58) Field of Classification Search
CPC ................ C12Q 1/6869; C12Q 1/6874; G01N 33/48721
See application file for complete search history.

(56) References Cited

U.S. PATENT DOCUMENTS

| 5,795,782 A | 8/1998 | Church |
| 6,015,714 A | 1/2000 | Baldarelli |
| 6,267,872 B1 | 7/2001 | Akeson |
| 6,362,002 B1 | 3/2002 | Denison |
| 6,464,842 B1 | 10/2002 | Golovchenko |
| 6,617,113 B2 | 9/2003 | Deamer |
| 6,627,067 B1 | 9/2003 | Branton |
| 6,673,615 B2 | 1/2004 | Denison |
| 6,746,594 B2 | 6/2004 | Akeson |
| 7,005,264 B2 | 2/2006 | Su |
| 7,846,738 B2 | 12/2010 | Golovchenko |
| 8,637,650 B2 | 1/2014 | Cherkasov |
| 2003/0044781 A1 | 3/2003 | Korlach |
| 2003/0104428 A1 | 6/2003 | Branton et al. |
| 2003/0124576 A1 | 6/2003 | Branton |
| 2004/0121525 A1 | 6/2004 | Chopra |
| 2009/0186343 A1 | 7/2009 | Wang |
| 2009/0298072 A1 | 12/2009 | Ju |
| 2012/0052506 A1* | 3/2012 | Yue ................. G01N 33/52 435/6.12 |
| 2013/0244340 A1 | 9/2013 | Davis |
| 2013/0264207 A1 | 10/2013 | Ju |
| 2014/0134616 A1 | 5/2014 | Davis |
| 2014/0309144 A1* | 10/2014 | Turner ............ C12Q 1/6869 506/16 |
| 2015/0119259 A1 | 4/2015 | Ju |
| 2015/0368710 A1 | 12/2015 | Fuller |
| 2016/0333327 A1 | 11/2016 | Ayer et al. |
| 2017/0088588 A1 | 3/2017 | Dorwart |
| 2017/0088890 A1 | 3/2017 | Craig |
| 2017/0175183 A1 | 6/2017 | Ju |
| 2017/0306397 A1 | 10/2017 | Craig |
| 2018/0002750 A1 | 1/2018 | Ambroso |

FOREIGN PATENT DOCUMENTS

| WO | 2005044836 A | 5/2005 |
| WO | 2013154999 A2 | 10/2013 |
| WO | 2013191793 A1 | 12/2013 |
| WO | 2015148402 A1 | 10/2015 |
| WO | 2017042038 A | 3/2017 |

OTHER PUBLICATIONS

Crauste, et al., "Insights into the Soluble PEG-Supported Synthesis of Cytosine-Containing Nucleoside 5'-Mono-, Di-, and Triphosphates", The Journal of Organic Chemistry, 2009, vol. 74, No. 23, pp. 9165-9172, Dec. 4, 2009.

Fuller, C., et al., "Real-time single-molecule electronic DNA sequencing by synthesis using polymer-tagged nucleotides on a nanopore array", PNAS, 2016, pp. 5233-5238, vol. 113, No. 19.

International Search Report and Written Opinion of the International Searching Authority in PCT/EP2017/062552, dated Sep. 15, 2017.

Kumar, et al., "PEG-Labeled Nucleotides and Nanopore Detection for Single Molecule DNA Sequencing by Synthesis", Scientific Reports, 2012, 2:684; DOI: 10.1038/srep00684.

Pendergast, et al., "Synthesis and P2Y receptor activity of a series of uridine dinucleoside 5'-polyphosphates", Bioorganic & Medical Chemistry Letters, vol. 11, No. 2: pp. 157-160, Jan. 26, 2001.

Robertson, et al., "Single-molecule mass spectrometry in solution using a solitary nanopore", Proc Natl Acad Sci USA. May 15, 2007;104(20):8207-11. Epub: May 9, 2007.

(Continued)

*Primary Examiner* — Jezia Riley

(74) *Attorney, Agent, or Firm* — FisherBroyles, LLP; Victoria L. Boyd; Adam Kurt Whiting

(57) ABSTRACT

The present disclosure relates to tagged multi-nucleotide compounds, which comprise a single tag moiety covalently linked to a plurality of nucleoside-5'-oligophosphate moieties. As disclosed herein, these tagged multi-nucleotide compounds have improved characteristics as polymerase substrates and can be used in a range of nucleic acid detection and sequencing methods, including nanopore sequencing-by-synthesis.

17 Claims, 3 Drawing Sheets

Specification includes a Sequence Listing.

(56) References Cited

OTHER PUBLICATIONS

Shchepinov, et al., "Oligonucleotide dendrimers: synthesis and use as polylabelled DNA probes", Nucleic Acids Research, 1997, vol. 25, No. 22, 4447-4454.

Valeva, et al., "Membrane insertion of the heptameric staphylococcal alpha-toxin pore—A domino-like structural ransition that is allosterically modulated by the target cell membrane", J. Biol. Chem., 2012, 276(18): 14835-14841.

Zakeri, et al., "Spontaneous Intermolecular Amide Bond Formation between Side Chains for Irreversible Peptide Targeting", Journal of the American Chemical Society, 2010, 132:4526-4527.

* cited by examiner

TAGGED MULTI-NUCLEOTIDES USEFUL FOR NUCLEIC ACID SEQUENCING

CROSS-REFERENCE TO RELATED APPLICATIONS

The present application is an application is a continuation of U.S. patent application Ser. No. 15/604,611, filed May 24, 2017, which claims priority to U.S. Provisional Application No. 62/342,796, filed May 27, 2016, each of which is incorporated herein in their entirety by reference.

TECHNICAL FIELD

This application relates to tagged multi-nucleotide compounds comprising a single tag moiety covalently linked to a plurality of nucleoside-5'-oligophosphate moieties, methods of preparing and using the disclosed compounds as polymerase substrates in methods for sequencing nucleic acids, and in particular, nanopore-based sequencing methods.

REFERENCE TO SEQUENCE LISTING

The official copy of the Sequence Listing is submitted concurrently with the specification as an ASCII formatted text file via EFS-Web, with a file name of "04338-536US1_SL_ST25.txt", a creation date of May 8, 2017, and a size of 56,094 bytes. The Sequence Listing filed via EFS-Web is part of the specification and is incorporated in its entirety by reference herein.

BACKGROUND

Nucleic acid sequencing is the process for determining the nucleotide sequence of a nucleic acid. Such sequence information may be helpful in diagnosing and/or treating a subject. For example, the sequence of a nucleic acid of a subject may be used to identify, diagnose, and potentially develop treatments for genetic diseases. As another example, research into pathogens may lead to treatment for contagious diseases. Since some diseases are characterized by as little as one nucleotide difference in a chain of millions of nucleotides, highly accurate sequencing is essential.

Single-molecule sequencing-by-synthesis (SBS) techniques using nanopores have been developed. See e.g., US Pat. Publ. Nos. 2013/0244340 A1, 2013/0264207 A1, 2014/0134616 A1. Nanopore SBS involves using a DNA polymerase (or other strand-extending enzyme) to synthesize a DNA strand complementary to a target sequence template and concurrently determining the identity of each nucleotide monomer as it is added to the growing strand, thereby determining the target sequence. Each added nucleotide monomer is detected by monitoring current flow through a nanopore located adjacent to the polymerase active site over time as the strand is synthesized. Obtaining an accurate signal requires proper positioning of the polymerase active site near a nanopore, and the use of a tag on each added nucleotide which can enter the nanopore and provide an identifiable change in the current flowing through the pore. It also requires controlling the parameters of DNA polymerase strand extension reaction, including nucleotide monomer on-rate, processivity, transition rate, and overall read length. In order to provide for accurate nanopore sequencing, it is important for the tag to enter and reside in the nanopore for a sufficient amount of time (i.e., "dwell time"), and while residing in the nanopore, provide for a sufficiently detectable, and identifiable blockage of current through the nanopore (i.e., "blocking current"), such that the specific nucleotide associated with the tag can be distinguished unambiguously from the other tagged nucleotides.

Kumar et al., (2012) "PEG-Labeled Nucleotides and Nanopore Detection for Single Molecule DNA Sequencing by Synthesis," Scientific Reports, 2:684; DOI: 10.1038/srep00684, describes using a nanopore to distinguish four different length PEG-coumarin tags attached via a terminal 5'-phosphoramidate to a dG nucleotide, and separately demonstrates efficient and accurate incorporation of these four PEG-coumarin tagged dG nucleotides by DNA polymerase. See also, US Patent Application Publications US 2013/0244340 A1, published Sep. 19, 2013, US 2013/0264207 A1, published Oct. 10, 2013, and US 2014/0134616 A1, published May 14, 2014.

WO 2013/154999 and WO 2013/191793 describe the use of tagged nucleotides for nanopore SBS, and disclose the possible use of a single nucleotide attached to a single tag comprising branched PEG chains.

WO 2015/148402 describes the use of tagged nucleotides for nanopore SBS comprising a single nucleotide attached to a single tag, wherein the tag comprises any or a range of oligonucleotides (or oligonucleotide analogues) that have lengths of 30 monomer units or longer.

The above-described prior disclosures teach tagged nucleotide structures having a single nucleotide moiety attached to a single tag, or a branched tag. The general approach of these disclosures is to increase the size and structural variability of the tag and thereby facilitate better nanopore detection for SBS. The increased size these prior disclosed tagged nucleotides however creates a further obstacle to their utility for SBS by decreasing the substrate concentrations that can be achieved.

The above-described prior disclosures fail to teach specific tagged nucleotide structures that can provide high enough substrate concentrations to drive the polymerase extension reaction at rates desirable for efficient SBS, particularly in a nanopore setting where solution volumes are minimal and molecular concentrations critical. Accordingly, there remains a need for tagged nucleotide compositions and methods that can be used to improve efficiency and throughput in nanopore SBS and other sequencing techniques.

SUMMARY

The present disclosure provides tagged multi-nucleotide compounds comprising a single tag covalently linked to a plurality of nucleoside-5'-oligophosphate moieties, wherein the tag is a molecular moiety capable of producing a detectable signal, and each nucleoside-5'-oligophosphate moiety is capable of being a substrate for a polymerase. The disclosure also provides processes for preparing and using such tagged multi-nucleotide compounds, including their use in nanopore sequencing. These tagged multi-nucleotide compounds are well-suited for use in any nucleic acid sequencing-by-synthesis system that utilizes tagged nucleotides as polymerase substrates and identifies the unknown sequence by detection of the tagged by-products of the polymerase extension reaction. The specific tagged multi-nucleotide structure comprising a single tag covalently linked to a plurality of nucleoside-5'-oligophosphate moieties, each of which is capable of being a polymerase substrate, increases the effective concentration of substrate at the polymerase active site while without additional tag moieties that greatly increase the molecular mass and decrease solubility. This increase in effective concentration increases the overall efficiency of the polymerase strand extension reaction thereby increasing tag detection, sequence throughput, and sequencing accuracy.

In some embodiments, the present disclosure provides a compound comprising a single tag covalently linked to a plurality of nucleoside-5'-oligophosphate moieties, wherein the tag is a molecular moiety capable of producing a detectable signal, and each nucleoside-5'-oligophosphate moiety is capable of being a substrate for a polymerase. In various embodiments, the compound comprises the single tag covalently linked to from 2 to 12 nucleoside-5'-oligophosphate moieties, optionally from 2 to 6 nucleoside-5'-oligophosphate moieties.

In some embodiments, the compound has structural formula (I)

$$[\text{N-P-L}]_m\text{-T} \qquad (I)$$

wherein, N is a nucleoside; P is an oligophosphate covalently attached to a 5'-O group of the nucleoside, wherein the oligophosphate consists of 3 to 12 phosphate groups; L is a linker covalently attached to a terminal phosphate group of the oligophosphate; m is from 2 to 12 and indicates the number of N-P-L moieties; and T is a tag covalently attached the N-P-L moieties, wherein the tag is a molecular moiety capable of producing a detectable signal.

In some embodiments, the compound has structural formula (II)

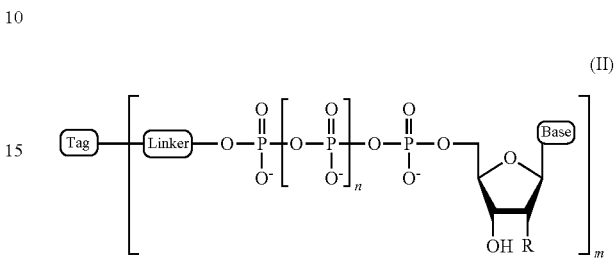

wherein, Base is selected from adenosine, cytidine, guanosine, thymidine, and uridine; R is selected from H and OH; n is from 1 to 4; Linker is a linker comprising a covalently bonded chain of 2 to 100 atoms; m is from 2 to 12; and Tag is a molecular moiety which is capable of producing a detectable signal.

In some embodiments, the compound of structural formula (I) or (II) comprises a compound wherein m is from 2 to 6, or optionally wherein m is from 2 to 3.

In some embodiments, the compound has structural formula (IIIa), (IIIb), or (IIIc):

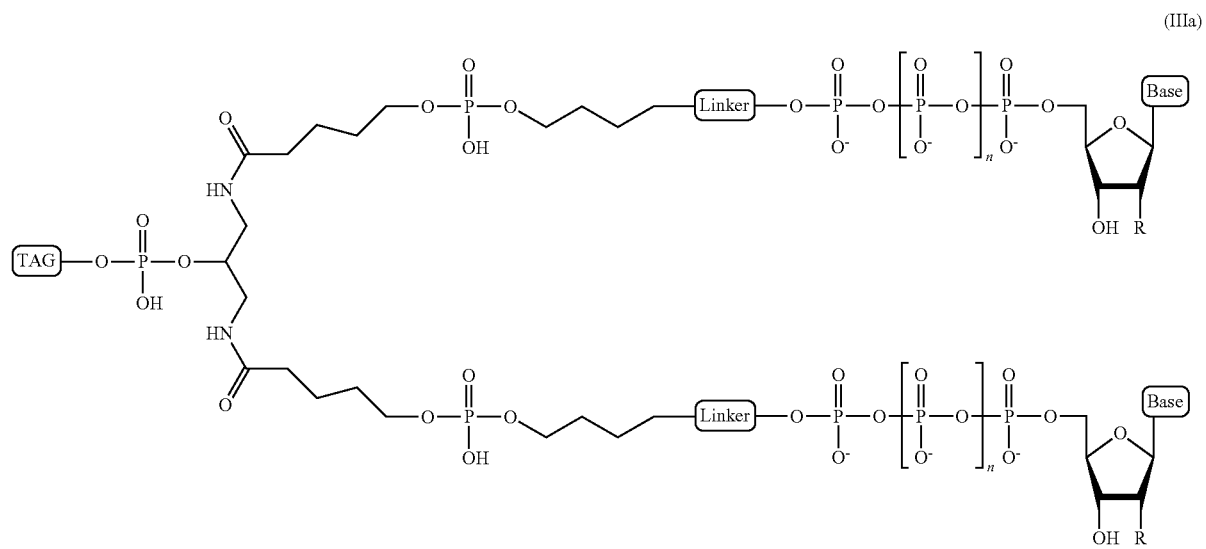

-continued
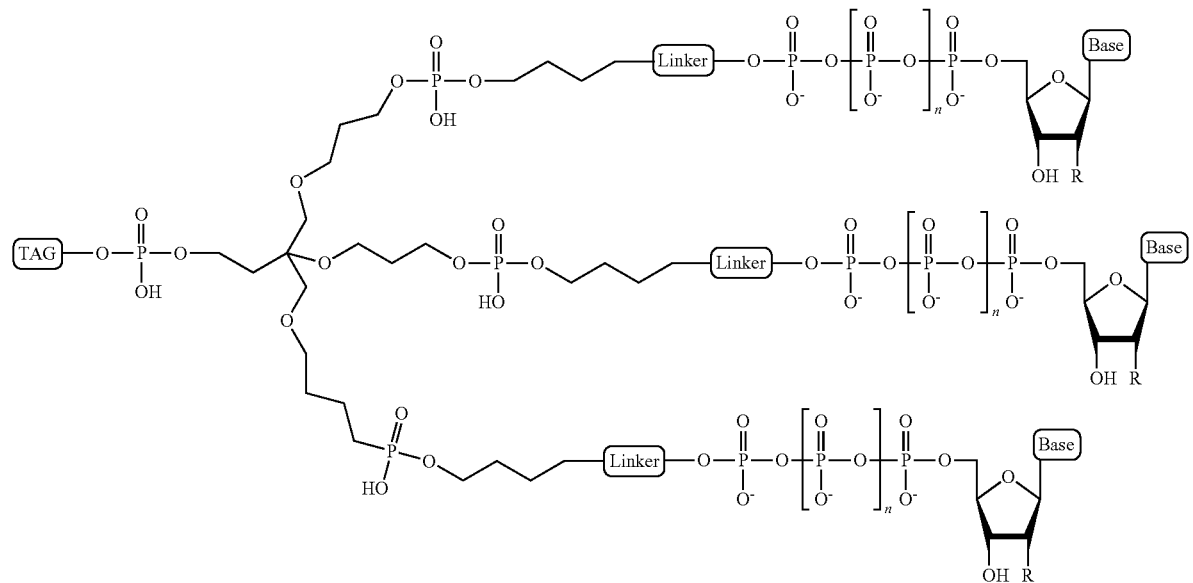
(IIIb)
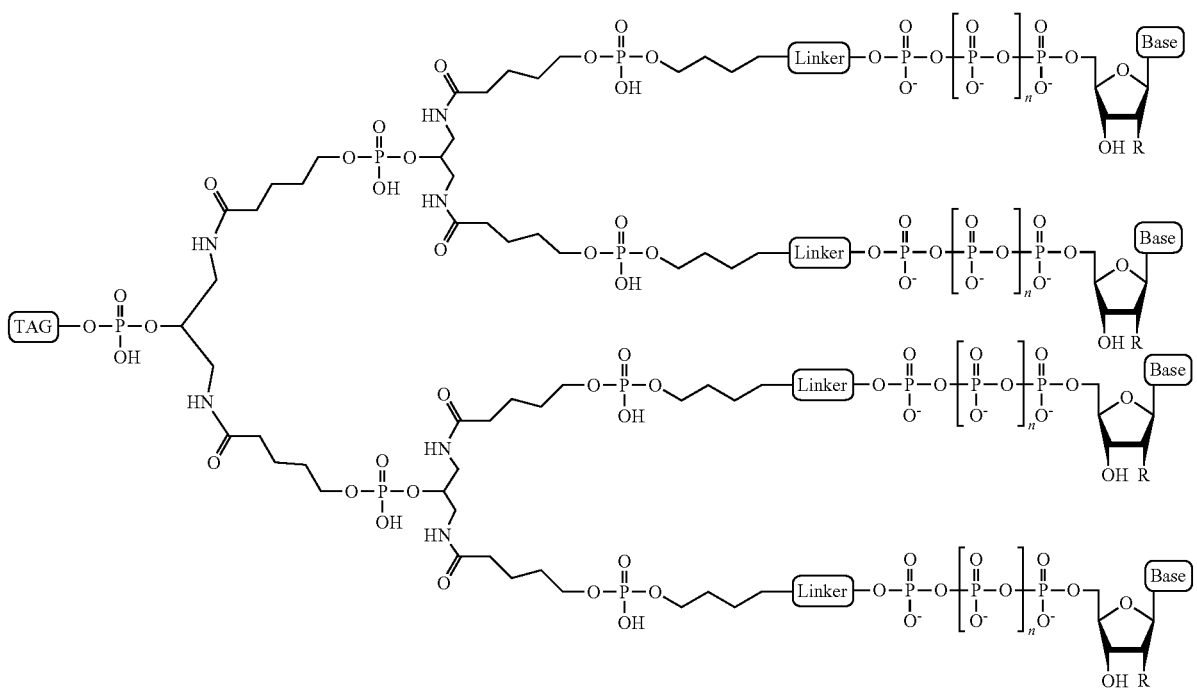
(IIIc)
wherein, Base is selected from adenosine, cytidine, guanosine, thymidine, and uridine; R is selected from H and OH; n is from 1 to 4; Linker is a linker comprising a covalently bonded chain of 2 to 100 atoms; and Tag is a molecular moiety capable of producing a detectable signal.

In some embodiments, the compound has structural formula structural formula (IIId), (IIIe), or (IIIf),
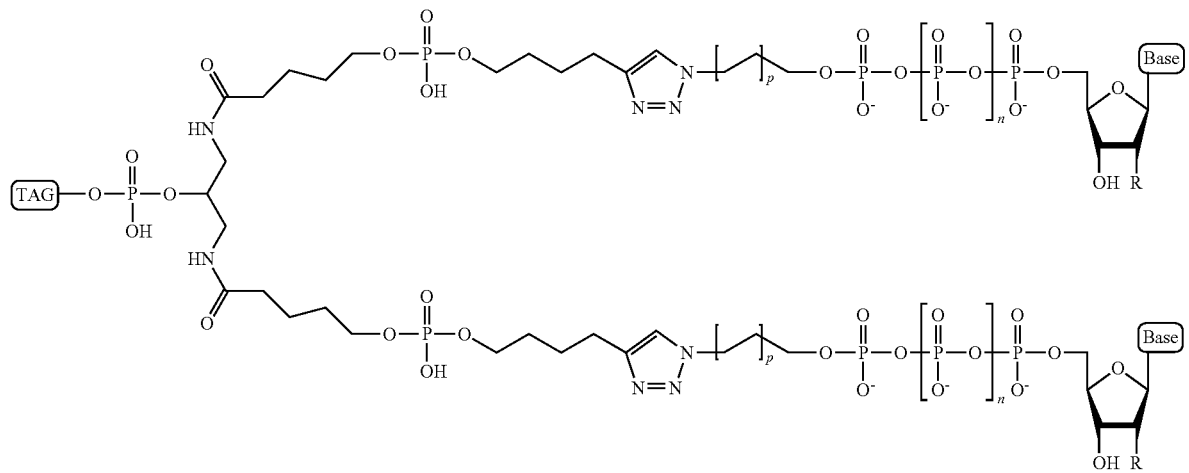
(IIId)
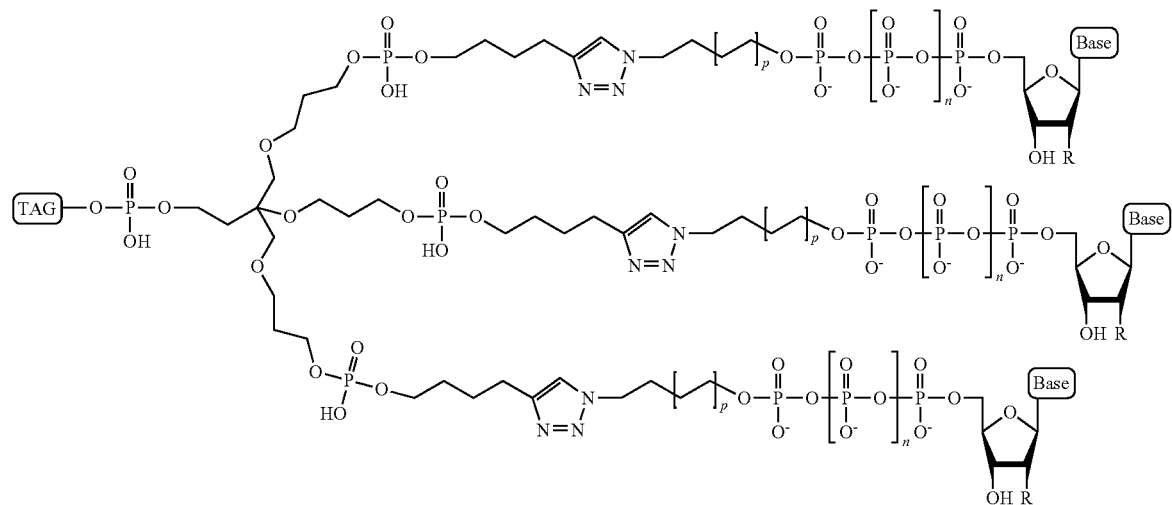
(IIIe)

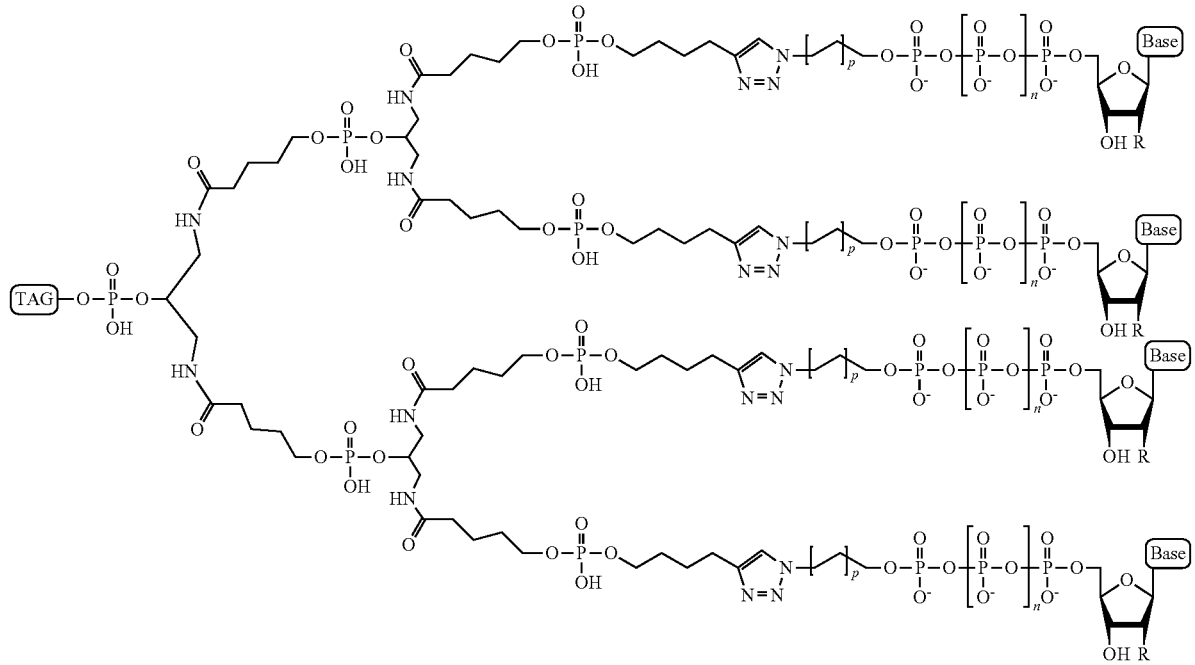

(IIIf)

wherein, Base is selected from adenosine, cytidine, guanosine, thymidine, and uridine; R is selected from H and OH; n is from 1 to 4; p is from 2 to 10; and Tag is a molecular moiety capable of producing a detectable signal.

In some embodiments of the compounds disclosed herein (e.g., compounds of structure formula (I) and (II)), the compound when used as a polymerase substrate results in increased extension efficiency relative to a compound comprising the single tag covalently linked to a single nucleoside-5'-oligophosphate; and optionally, the increase in extension efficiency resulting from the use of the compound as a polymerase substrate is at least 2-fold, at least 3-fold, at least 4-fold, at least 5-fold, at least 10-fold, or more.

In some embodiments of the compounds disclosed herein (e.g., compounds of structure formula (I) and (II)), the detectable signal is selected from a nanopore detectable signal, an optically detectable signal, and a mass spectrometrically detectable signal. In some embodiments, the detectable signal is an optically detectable, optionally a signal from a fluorescent moiety. In some embodiments, the detectable signal is a nanopore detectable signal and the tag is a molecular moiety capable of entering into, becoming positioned in, being captured by, translocating through, and/or traversing a nanopore, and thereby result in a detectable change in current through the nanopore.

In some embodiments of the compounds disclosed herein (e.g., compounds of structure formula (I) and (II)), the Tag comprises a molecular moiety selected from the group consisting of a polyethylene-glycol (PEG) oligomer, an organic dye moiety, an oligonucleotide (wherein the oligonucleotide comprises natural and/or non-natural analog monomer units), a polypeptide (wherein the polypeptide comprises natural and/or non-natural analog monomer units), and an oligomeric moiety comprising a combination of any of these. In some embodiments, the Tag comprises an oligonucleotide, optionally an oligonucleotide having a structure selected from Tables 3, 9, or 11. In some embodiments, the Tag comprises an oligonucleotide having a sequence selected from SEQ ID NO:1-109. In some embodiments, the Tag comprises an oligonucleotide having a monomer unit length of from 15-mer to 45-mer, from 20-mer to 40-mer, from 20-mer to 30-mer, or from 20-mer to 25-mer. In some embodiments, the Tag comprises a polymeric structure, optionally a polymeric structure comprising at least one monomer unit resulting from the reaction of an amidite reagent selected from Table 4. In some embodiments, the Tag comprises a polypeptide, optionally a polypeptide having a structure selected from Table 5. In some embodiments, the Tag comprises a polypeptide having a sequence selected from SEQ ID NO:110-123.

In some embodiments of the compounds disclosed herein (e.g., compounds of structure formula (I) and (II)), the oligophosphate consists of from 3 to 9 phosphate groups, optionally from 4 to 6 phosphate groups, or optionally 6 phosphate groups.

In some embodiments of the compounds disclosed herein (e.g., compounds of structure formula (I) and (II)), the tag or linker comprises a branched or dendrimeric moiety capable of forming covalent linkages with three or more molecular moieties. In some embodiments, the branched or dendrimeric moiety is a doubler linker, optionally wherein the doubler linker results from the reaction of an amidite reagent of compound (19). In some embodiments, the branched or dendrimeric moiety is a trebler linker, optionally wherein the trebler linker results from the reaction of an amidite reagent of compound (20).

In some embodiments of the compounds disclosed herein (e.g., compounds of structure formula (I) and (II)), the linker comprises a chemical group selected from the group consisting of: ester, ether, thioether, amine, amide, imide, benzene, benzyl ether, phenol, bis-hydroxyethylbenzene, carbonate, carbamate, squarate, thiazole, thiazolidine, hydrazone, oxime, triazole, dihydropyridazine, phosphodiester, polyethylene glycol (PEG), and combinations thereof.

In some embodiments of the compounds disclosed herein (e.g., compounds of structural formulas (I) and (II)), the linker comprises a chemical group of structural formulas (XVd) or (XVe).

In some embodiments, the disclosure provides methods of preparing compounds as disclosed herein (e.g., compounds of structure formula (I) and (II)), the method comprises the steps of: (a) providing (i) a nucleotide with from 3 to 12 phosphates attached to its 5'-position, wherein the terminal phosphate is coupled to a first linker forming group; and (ii) a tag, wherein the tag comprises a molecular moiety which is capable of producing a detectable signal, and is coupled to branched or dendrimeric linker comprising at least two second linker forming groups that are each capable of reacting with a first linker forming group to form a covalent linker between at least two nucleotides and a single tag; wherein the first linker forming group is selected from the compounds of structural formulas (IVa)-(XVIIa) and the second linker forming group is the corresponding reactive compound of structural formulas (IVb)-(XVIIb); or the first linker forming group is selected from the compounds of structural formulas (IVb)-(XVIIb) and the second linker forming group is the corresponding reactive compound of structural formulas (IVa)-(XVIIa); and (b) reacting the first linker forming group with the second linker forming group, thereby forming a covalent linkage between at least two nucleotides and a single tag.

In some embodiments, the present disclosure provide a composition comprising a set of any of the compounds as disclosed herein (e.g., compounds of structure formula (I) and (II)), wherein each compound in the set has a different tag, wherein each different tag causes a different detectable signal; optionally, wherein the detectable signal is selected from a nanopore detectable signal, an optically detectable signal, and a mass spectrometrically detectable signal. In some embodiments, the different detectable signal is a different blocking current when the tag is situated in a nanopore.

In some embodiments of the composition comprising a set of compounds, at least one of the different tags comprises an oligonucleotide, optionally an oligonucleotide having a structure selected from Table 3, 7, 8, or 10, optionally an oligonucleotide having a sequence selected from SEQ ID NO:1-109. In some embodiments, the set of compounds comprises $(dA6P)_2$-$dT_5$-(BHEB)-$dT_{14}$-C3; $(dC6P)_2$-$dT_{20}$-C3; $(dT6P)_2$-$dT_4$-(N3CE-dT)$_3$-$dT_{13}$-C3; and $(dG6P)_2$-$dT_6$-(Tmp)$_6$-$dT_8$-C3. In some embodiments, the set of compounds comprises $(dA6P)_2$-$dT_4$-(idSp-dT)$_4$-$dT_8$-C3; $(dC6P)_2$-$dT_{20}$-C3; $(dT6P)_2$-$dT_4$-(N3CE-dT)$_3$-$dT_{13}$-C3; and $(dG6P)_2$-$dT_6$-(Tmp)$_6$-$dT_8$-C3.

In some embodiments, the present disclosure provides a method for determining the sequence of a nucleic acid comprising: (a) providing a nanopore sequencing composition comprising: a membrane, an electrode on the cis side and the trans side of the membrane, a nanopore with its pore extending through the membrane, an electrolyte solution in contact with both electrodes, an active polymerase situated adjacent to the nanopore, and a primer strand complexed with the polymerase; (b) contacting the nanopore sequencing composition with (i) a strand of the nucleic acid; and (ii) a set of compounds each comprising a single tag covalently linked to a plurality of nucleoside-5'-oligophosphate moieties, wherein the tag is a molecular moiety capable of producing a detectable signal, and each nucleoside-5'-oligophosphate moiety is capable of being a substrate for a polymerase, and each member of the set of compounds has a different tag that produces a different blocking current and/or dwell time when the tag is situated in a nanopore; and (c) detecting the different blocking currents and/or different dwell times of the tags over time and correlating to each of the different tags the different compounds incorporated by the polymerase which are complementary to the nucleic acid sequence, and thereby determining the nucleic acid sequence. In some embodiments of the method, the at least two compounds having different tags have blocking currents that differ by at least 10%, at least 25%, at least 50%, or at least 75%. In some embodiments of the method, each compound in the set of compounds has a different tag, wherein each different tag causes a different detectable signal. In some embodiments, at least one of the different tags comprises an oligonucleotide, optionally an oligonucleotide having a structure selected from Table 3, 7, 8, or 10, optionally an oligonucleotide having a sequence selected from SEQ ID NO:1-109. In some embodiments of the method, the set of compounds comprises $(dA6P)_2$-$dT_5$-(BHEB)-$dT_{14}$-C3; $(dC6P)_2$-$dT_{20}$-C3; $(dT6P)_2$-$dT_4$-(N3CE-dT)$_3$-$dT_{13}$-C3; and $(dG6P)_2$-$dT_6$-(Tmp)$_6$-$dT_8$-C3. In some embodiments of the method, the set of compounds comprises $(dA6P)_2$-$dT_4$-(idSp-dT)$_4$-$dT_8$-C3; $(dC6P)_2$-$dT_{20}$-C3; $(dT6P)_2$-$dT_4$-(N3CE-dT)$_3$-$dT_{13}$-C3; and $(dG6P)_2$-$dT_6$-(Tmp)$_6$-$dT_8$-C3.

DETAILED DESCRIPTION

Figure 1:
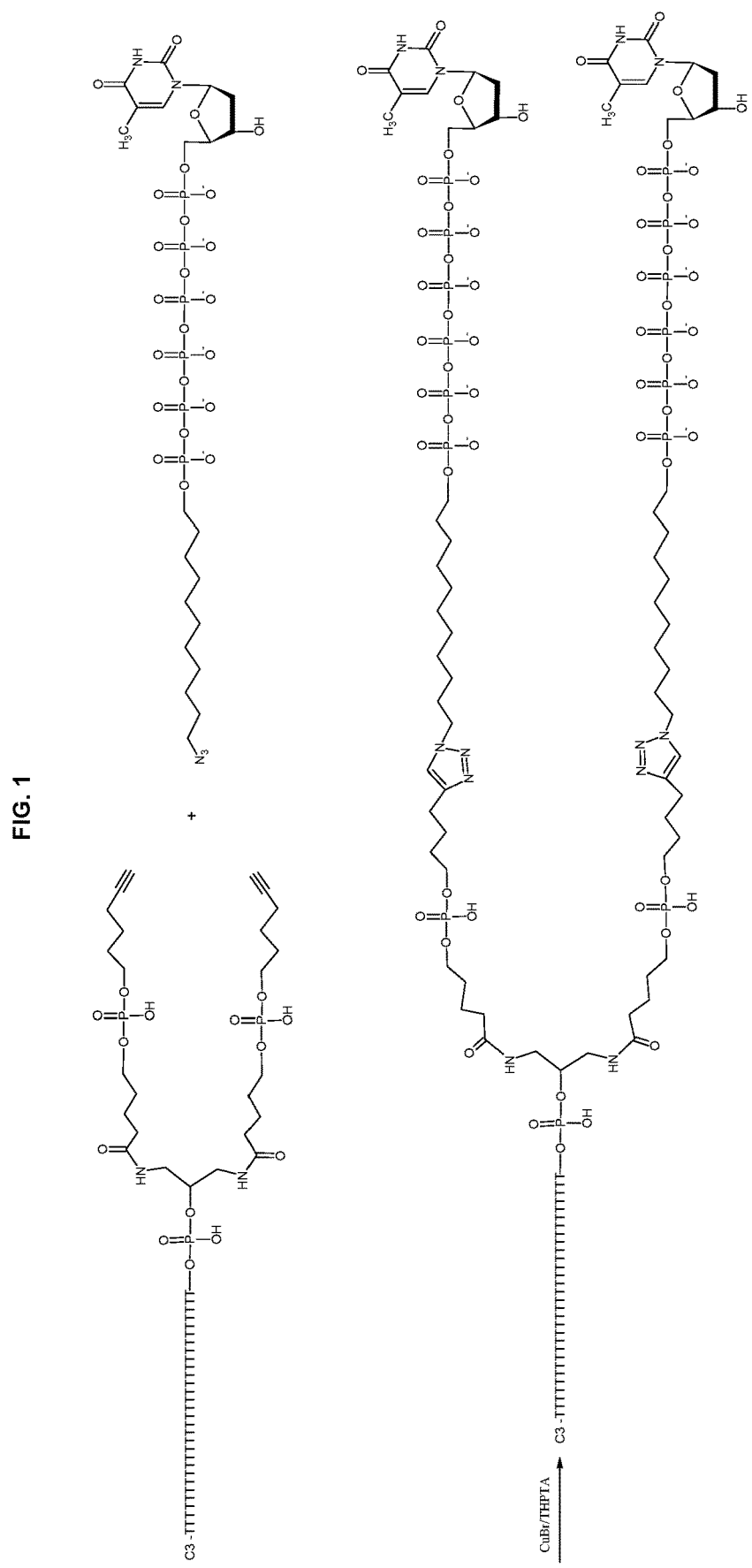
FIG. 1 depicts a doubler-linker conjugation reaction useful for preparing the tagged multi-nucleotide substrate of the structure [dT6P-linker]$_2$-$dT_{30}$ (compound (3a)).

For the descriptions herein and the appended claims, the singular forms "a", and "an" include plural referents unless the context clearly indicates otherwise. Thus, for example, reference to "a protein" includes more than one protein, and reference to "a compound" refers to more than one compound. The use of "comprise," "comprises," "comprising" "include," "includes," and "including" are interchangeable and not intended to be limiting. It is to be further understood that where descriptions of various embodiments use the term "comprising," those skilled in the art would understand that in some specific instances, an embodiment can be alternatively described using language "consisting essentially of" or "consisting of."

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding (i) either or (ii) both of those included limits are also included in the invention. For example "1 to 50" includes "2 to 25", "5 to 20", "25 to 50", "1 to 10", etc.

It is to be understood that both the foregoing general description, including the drawings, and the following detailed description are exemplary and explanatory only and are not restrictive of this disclosure.

Definitions

The technical and scientific terms used in the descriptions herein will have the meanings commonly understood by one of ordinary skill in the art, unless specifically defined otherwise. Accordingly, the following terms are intended to have the following meanings.

"Nucleic acid," as used herein, refers to a molecule of one or more nucleic acid subunits which comprise one of the nucleobases, adenine (A), cytosine (C), guanine (G), thymine (T), and uracil (U), or variants thereof. Nucleic acid can refer to a polymer of nucleotides (e.g., dAMP, dCMP, dGMP, dTMP), also referred to as a polynucleotide or oligonucleotide, and includes DNA, RNA, in both single and double-stranded form, and hybrids thereof.

"Nucleotide," as used herein, refers to a nucleoside-5'-oligophosphate compound, or structural analog of a nucleoside-5'-oligophosphate, which is capable of acting as a substrate or inhibitor of a nucleic acid polymerase. Exemplary nucleotides include, but are not limited to, nucleoside-5'-triphosphates (e.g., dATP, dCTP, dGTP, dTTP, and dUTP); nucleosides (e.g., dA, dC, dG, dT, and dU) with 5'-oligophosphate chains of 4 or more phosphates in length (e.g., 5'-tetraphosphosphate, 5'-pentaphosphosphate, 5'-hexaphosphosphate, 5'-heptaphosphosphate, 5'-octaphosphosphate); and structural analogs of nucleoside-5'-triphosphates that can have a modified base moiety (e.g., a substituted purine or pyrimidine base), a modified sugar moiety (e.g., an O-alkylated sugar), and/or a modified oligophosphate moiety (e.g., an oligophosphate comprising a thiophosphate, a methylene, and/or other bridges between phosphates).

Nucleoside," as used herein, refers to a molecular moiety that comprises a naturally occurring or non-naturally occurring nucleobase attached to a sugar moiety (e.g., ribose or deoxyribose).

"Oligophosphate," as used herein, refers to a molecular moiety that comprises an oligomer of phosphate groups. For example, an oligophosphate can comprise an oligomer of from 2 to 20 phosphates, an oligomer of from 3 to 12 phosphates, an oligomer of from 3 to 9 phosphates.

"Polymerase," as used herein, refers to any natural or non-naturally occurring enzyme or other catalyst that is capable of catalyzing a polymerization reaction, such as the polymerization of nucleotide monomers to form a nucleic acid polymer. Exemplary polymerases that may be used in the compositions and methods of the present disclosure include the nucleic acid polymerases such as DNA polymerase (e.g., enzyme of class EC 2.7.7.7), RNA polymerase (e.g., enzyme of class EC 2.7.7.6 or EC 2.7.7.48), reverse transcriptase (e.g., enzyme of class EC 2.7.7.49), and DNA ligase (e.g., enzyme of class EC 6.5.1.1).

"Linker," as used herein, refers to any molecular moiety that provides a bonding attachment with some space between two or more molecules, molecular groups, and/or molecular moieties.

"Tag," as used herein, refers to a moiety or part of a molecule that enables or enhances the ability to detect and/or identify, either directly or indirectly, a molecule or molecular complex, which is coupled to the tag. For example, the tag can provide a detectable property or characteristic, such as steric bulk or volume, electrostatic charge, electrochemical potential, optical and/or spectroscopic signature.

"Nanopore," as used herein, refers to a pore, channel, or passage formed or otherwise provided in a membrane or other barrier material that has a characteristic width or diameter of about 0.1 nm to about 1000 nm. A nanopore can be made of a naturally-occurring pore-forming protein, such as α-hemolysin from S. aureus, or a mutant or variant of a wild-type pore-forming protein, either non-naturally occurring (i.e., engineered) such as α-HL-C46, or naturally occurring. A membrane may be an organic membrane, such as a lipid bilayer, or a synthetic membrane made of a non-naturally occurring polymeric material. The nanopore may be disposed adjacent or in proximity to a sensor, a sensing circuit, or an electrode coupled to a sensing circuit, such as, for example, a complementary metal-oxide semiconductor (CMOS) or field effect transistor (FET) circuit.

"Nanopore-detectable tag" as used herein refers to a tag that can enter into, become positioned in, be captured by, translocate through, and/or traverse a nanopore and thereby result in a detectable change in current through the nanopore. Exemplary nanopore-detectable tags include, but are not limited to, natural or synthetic polymers, such as polyethylene glycol, oligonucleotides, polypeptides, carbohydrates, peptide nucleic acid polymers, locked nucleic acid polymers, any of which may be optionally modified with or linked to chemical groups, such as dye moieties, or fluorophores, that can result in detectable nanopore current changes.

"Background current" as used herein refers to the current level measured across a nanopore when a potential is applied and the nanopore is open and unblocked (e.g., there is no tag in the nanopore).

"Blocking current" as used herein refers to the current level measured across a nanopore when a potential is applied and a tag is present the nanopore. Generally, the presence of the tag in the nanopore restricts the flow of charged molecules through the nanopore thereby altering the background current level.

"Dwell time" as used herein in the context of capture of a tag in a nanopore refers to the time that the tag spends in the nanopore as detected by a blocking current.

"Extension efficiency" as used herein in the context of a tagged multi-nucleotide compound acting as a substrate for a polymerase refers to any parameter associated with the efficiency of the polymerase strand extension reaction, including but not limited to: processivity, transition rate, on-rate ($k_{on}$), read length, read length fidelity, elongation rate, sequencing accuracy, long continuous read capability.

DETAILED DESCRIPTION OF VARIOUS EMBODIMENTS

Overview: Tagged Multi-Nucleotide Compounds and Nanopore Sequencing

The present disclosure describes compositions of tagged multi-nucleotide compounds and related methods, devices, and systems that are useful for nanopore sequencing of nucleic acids. The tagged multi-nucleotide compounds can be used in methods to accurately detect individual nucleotide incorporation by a nucleic acid polymerase into a growing strand that is complementary to a template nucleic acid strand. Generally, the strand extending enzyme (e.g., DNA polymerase) specifically binds a tagged multi-nucleotide compound that is complimentary to a template nucleic acid strand which is hybridized to the growing nucleic acid strand at its active site. The strand extending enzyme then catalytically couples (i.e., incorporates) the complimentary nucleotide moiety of the tagged multi-nucleotide compound to the end of the growing nucleic acid strand. Completion of the catalytic incorporation event results in the release of the tag moiety and oligophosphate moiety (minus the one phosphate incorporated into the growing strand) which then passes through the adjacent nanopore.

Even before it undergoes catalytic process that releases it from the incorporated nucleotide however, the tag moiety of a tagged multi-nucleotide compound can enter the pore of the nanopore thereby altering the background current of the nanopore under a potential and causing a blocking current that can be detected. Various molecular properties of the tag moiety (e.g., mass, volume, 3-D structure, electrostatic charge) can greatly affect its interaction with the pore and thereby allowing for nanopore detection to distinguish different tag moieties each of which can correspond to a different nucleotide. A variety of nanopore systems and methods for using them to detect tagged molecules including tagged nucleotides in sequencing are known in the art. See, for example, U.S. patent application Ser. No. 12/308,091, Ju et al., filed May 18, 2009; U.S. patent application Ser. No. 13/994,431, Ju et al., filed Jun. 14, 2013; US Patent Application Publications US 2013/0244340 A1, published Sep. 19, 2013, US 2013/0264207 A1, published Oct. 10, 2013, and US 2014/0134616 A1, published May 14, 2014; PCT Appl. No. PCT/US13/35635, Ju et al., filed Apr. 8, 2013; and PCT Appl. No. PCT/US13/35640, Ju et al., filed Apr. 8, 2013, and PCT International Publication No. WO2015/148402, each of which is hereby incorporated herein by reference in its entirety.

In most embodiments, nanopore sequencing uses a mixture of four nucleotide analogs (e.g., dA6P, dC6P, dG6P, and dT6P) that can be incorporated by an enzyme into a growing strand, each nucleotide analog having a covalently attached tag moiety that provides an identifiable, and distinguishable signature when detected with a nanopore.

As described in the Background section, a range of tag moieties have been used in the context of nanopore detection, including a range of molecular moieties such as polyethylene-glycol (PEG) oligomers, organic dye moieties, oligonucleotides (wherein the oligonucleotide can comprise natural and non-natural analog monomer units), polypeptides (wherein the polypeptide can comprise natural and non-natural analog monomer units), and polymeric moieties comprising combinations of any of these. The wide range of monomeric units that can be synthesized (e.g., using automated phosphoramidite or peptide synthesis methods) provides for an extremely wide range of molecular properties that can mixed and matched to provide distinguishable nanopore detection. See e.g., PCT International Publication No. WO2015/148402, US Provisional Patent Appl. Nos. 62/235,551, filed Sep. 30, 2015, and 62/216,634, filed Sep. 10, 2015, each of which is hereby incorporated by reference herein.

Tagged Multi-Nucleotide Compound Structures

The present disclosure provides tagged multi-nucleotide compound embodiments that can be characterized by a range of structures. Generally, the tagged multi-nucleotide compound of the present disclosure comprise a single tag covalently linked to a plurality of nucleoside-5'-oligophosphate moieties, wherein the tag is a molecular moiety capable of producing a detectable signal, and each nucleoside-5'-oligophosphate moiety is capable of being a substrate for a polymerase. In some embodiments, the compound comprises the single tag covalently linked to from 2 to 12 nucleoside-5'-oligophosphate moieties, optionally from 2 to 6 nucleoside-5'-oligophosphate moieties.

As described elsewhere herein, tagged multi-nucleotide compound structure of the present disclosure results in technical advantages including increasing the effective concentration of the polymerase substrate and thereby resulted increased extension efficiency. Accordingly, in some embodiments, the tagged multi-nucleotide compounds of the present disclosure have increased extension efficiency as a substrate for a polymerase relative to a substrate compound comprising a single tag covalently linked to a single nucleoside-5'-oligophosphate. In some embodiments, the efficiency as a substrate for a polymerase is increased at least 2-fold, optionally an efficiency increased at least 3-fold, at least 4-fold, at least 5-fold, at least 10-fold, or more.

Although the present disclosure describes numerous embodiments where the tagged multi-nucleotide compounds can be used in SBS methods involving nanopore detection, it is also contemplated that the tagged multi-nucleotide compounds can be used in any method that involves detection of individual nucleotide incorporation by a nucleic acid strand-extending enzyme (e.g., polymerase). Thus, in some embodiments the present disclosure provides tagged multi-nucleotide compounds wherein the detectable signal produced by the tag moiety is selected from a nanopore detectable signal, an optically detectable signal, and a mass spectrometrically detectable signal.

Molecular moieties capable of producing mass spectrometrically, or optically detectable signals are well-known in the art. For example, there are numerous DNA detection or sequence techniques that utilize a single nucleotide with a fluorescent, fluorogenic, or chemiluminescent label attached to a terminal phosphate of the nucleotide (see e.g., U.S. Pat. No. 6,399,335 and published U.S. Patent Application Nos. 2003/0044781 and 2003/0124576, each of which is hereby incorporated by reference herein). It is contemplated that any of the assays using such terminal phosphate labelled nucleotides could be easily adapted tagged multi-nucleotide, wherein the tag can be any of these known fluorescent, fluorogenic, or chemiluminescent labels. Thus, the ordinary artisan can use the compound structures, branched or dendrimeric linkers, and synthesis methods disclosed herein to prepare such fluorescently tagged multi-nucleotide compounds.

Tags capable of producing a nanopore detectable signal generally include any molecular moiety capable of entering into, becoming positioned in, being captured by, translocating through, and/or traversing a nanopore, and thereby result in a detectable change in current through the nanopore. As noted in the Background section and elsewhere herein, a range of nanopore detectable molecular moieties have been described in the art, including polyethylene-glycol (PEG) oligomers, organic dye moieties, oligonucleotides (wherein the oligonucleotide can comprise natural and non-natural analog monomer units), polypeptides (wherein the polypeptide can comprise natural and non-natural analog monomer units), and polymeric moieties comprising combinations of any of these. Accordingly, in some embodiments, the tagged multi-nucleotide compounds comprise tags wherein the tag is a molecular moiety selected from the group consisting of a polyethylene-glycol (PEG) oligomer, an organic dye moiety, an oligonucleotide (wherein the oligonucleotide can comprise natural and/or non-natural analog monomer units), a polypeptide (wherein the polypeptide can comprise natural and/or non-natural analog monomer units), and an oligomeric moiety comprising a combination of any of these.

In some embodiments, the present disclosure provides a tagged multi-nucleotide compound of structural formula (I)

[N-P-L]$_m$-T  (I)

wherein, N is a nucleoside; P is an oligophosphate covalently attached to a 5'-O group of the nucleoside, wherein the oligophosphate consists of 3 to 12 phosphate groups; L is a linker covalently attached to a terminal phosphate group of the oligophosphate; m is from 2 to 12 and indicates the number of N-P-L moieties; and T is a tag covalently attached the N-P-L moieties, wherein the tag is a molecular moiety capable of producing a detectable signal.

The nucleoside (N) can be any nucleoside capable of being incorporated by a strand-extending enzyme, such as a polymerase, when the nucleoside is covalently coupled to an oligophosphate (P), such as a triphosphate. The nucleoside can comprise a naturally occurring or non-naturally occurring nucleobase, and a naturally occurring or non-naturally occurring sugar moiety, such as a ribose or deoxyribose group. In some embodiments, the nucleobase is selected from group consisting of adenosine, cytidine, guanosine, thymidine, and uridine. The sugar moiety should provide a free hydroxyl group at a position (e.g., a 3'-OH group) that can form a phosphodiester bond with a growing polynucleotide strand when catalytically incorporated by a strand extending enzyme. The nucleoside sugar moiety should also provide a group allowing covalent attachment of an oligophosphate moiety (e.g., a 5'-O group).

In some embodiments, the present disclosure provides a tagged multi-nucleotide compound of structural formula (II)

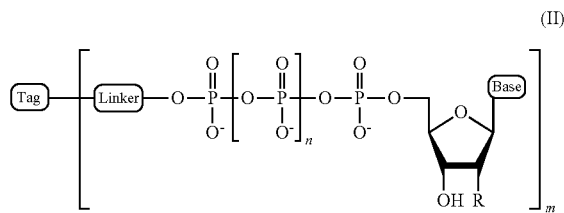

wherein, Base is selected from adenosine, cytidine, guanosine, thymidine, and uridine; R is selected from H and OH; n is from 1 to 4; Linker is a linker comprising a covalently bonded chain of 2 to 100 atoms; m is from 2 to 12; and Tag is a molecular moiety which is capable of producing a detectable signal.

In some embodiments, the nucleobase ("Base") can be any naturally or non-naturally occurring (e.g., chemically modified) base which is capable of being incorporated by a strand-extending enzyme, such as a polymerase. In some embodiments, the nucleobase is selected from group consisting of adenosine, cytidine, guanosine, thymidine, and uridine.

The oligophosphate (P) moiety of the tagged multi-nucleotide compounds can be any oligophosphate which, when attached to the 5'-O of the nucleoside, allows the resulting nucleotide to still be capable of being incorporated by a strand-extending enzyme, such as a polymerase. Generally, strand-extending enzymes, such as polymerase, are capable of incorporating nucleotides comprising oligophosphates having chains of from 3 to 12 phosphate groups. Accordingly, in a tagged multi-nucleotide compound of the present disclosure (e.g., the compound of structural formula (I) or (II)) the oligophosphate (P) group can comprise 3 to 12 phosphate groups.

As depicted in the compound of structural formula (II), the oligophosphate of 3 to 12 phosphate groups would be represented by values of n=1 to n=10. Thus, in some embodiments of the present disclosure, the tagged multi-nucleotide compound comprises an oligophosphate (P) group comprising 3 to 9 phosphate groups (or n=1 to 7 for formula (II)). In some embodiments, the oligophosphate group comprises 4 to 6 phosphate groups (or n=2 to 4 for formula (II)). In some embodiments, the oligophosphate group comprises 6 phosphate groups (or n=4 for formula (II)).

In other embodiments, the tagged multi-nucleotide compounds of the present disclosure can comprise oligophosphate chains of 4 to 20 phosphates, 4 to 12 phosphates, 4 to 9 phosphates, 4 to 6 phosphates, wherein the chain is attached at the 5' position of the nucleoside (e.g., 5'-tetraphosphate, 5'-pentaphosphate, 5'-hexaphosphate, 5'-heptaphosphate, 5'-octaphosphate, 5'-nonaphosphate, 5'-decaphosphate, etc.).

It is further contemplated that the tagged multi-nucleotide compounds of the present disclosure, can include oligophosphate moieties comprising modified phosphate groups, phosphate analogs, or other non-phosphate chemical groups, provided that the inclusion of such phosphate groups does not prevent the resulting tagged multi-nucleotide from being incorporated by a strand-extending enzyme when the oligophosphate is attached to the 5'-O of the nucleoside. Typically, incorporation by a strand-extending enzyme requires a naturally occurring phosphate group at the α-position and a phosphodiester bond between the α-position and β-positions of the oligophosphate. Thus, in some embodiments, the oligophosphate can comprise a thiophosphate group. Additionally, it is contemplated that the oligophosphate can include an oligomer of phosphate or phosphate-analog groups with one or more non-phosphate groups, such as a methylene, and/or a bridging group between two or more phosphate groups.

Linkers

It is also contemplated that a wide range of linkers can be used in the tagged multi-nucleotide compounds of structural formulas (I) and (II). Generally, the linker can comprise any molecular moiety that is capable of providing a covalent coupling and a desired spacing or structure between multiple nucleotides and a single tag.

The desired spacing or structure can be selected and optimized for the specific use of the tagged multi-nucleotide compound. For example, in a nanopore detection use, a linker can be selected that provides a spacing that allows the tag to enter and reside in the nanopore when any one of the multiple nucleotides forms a ternary complex with an adjacent polymerase. Depending on how the polymerase is coupled to the nanopore, a slightly shorter or longer spacing may be selected so as to provide a suitable nanopore detectable signal (e.g., blocking current) when the tag is situation in the pore. Generally, however, the linkers useful in the tagged multi-nucleotide compounds of the present disclosure (e.g., compounds of formulas (I) and (II)) comprise a covalently bonded chain of 2 to 100 atoms. In some embodiments, the linker chain of 2 to 100 atoms comprises one or more chemical moieties selected from the group consisting of: linear ($C_1$-$C_{12}$) alkyl, linear ($C_1$-$C_{12}$) alkene, linear ($C_1$-$C_{12}$) alkyne, ester, ether, thioether, amine, amide, imide, benzene, benzyl ether, phenol, bis-hydroxyethylbenzene, carbonate, carbamate, squarate, thiazole, thiazolidine, hydrazone, oxime, triazole, dihydropyridazine, phosphodiester, polyethylene glycol (PEG), and combinations thereof. A variety of linkers comprising a range of chemical moieties that are useful in the tagged multi-nucleotide compounds are described and exemplified herein.

Typically, the linker is formed during the preparation of a tagged multi-nucleotide compounds of structural formula (I) or (II), in a chemical reaction that covalent couples the terminal phosphate (or phosphate analog) of the oligophosphate moiety to the tag, or to a linker moiety that is attached to, or can be covalently attached to the tag. More specifically, this chemical reaction typically involves a tag modified with a reactive linker-forming group and a nucleotide comprising an oligophosphate moiety, wherein the terminus of the oligophosphate is also modified with a reactive linker-forming group. This linker forming chemical reaction can be depicted as in Scheme 1.

a "click" reaction between an azide linker forming group, and an alkyne linker forming group.

In addition, the overall linker can include $C_5$ linear alkyl and amide groups on one or both sides of the triazole moiety. Accordingly, in some embodiments, the linker comprises a chemical moiety, X, produced in the linker forming reaction between the linker forming reagents, $X_A$ and $X_B$, wherein X is a chemical moiety selected from the group consisting of ester, ether, thioether, amine, amide, imide, benzene, benzyl ether, phenol, bis-hydroxyethylbenzene, carbonate, carbamate, squarate, thiazole, thiazolidine, hydrazone, oxime, triazole, dihydropyridazine, phosphodiester, and polyethylene glycol (PEG).

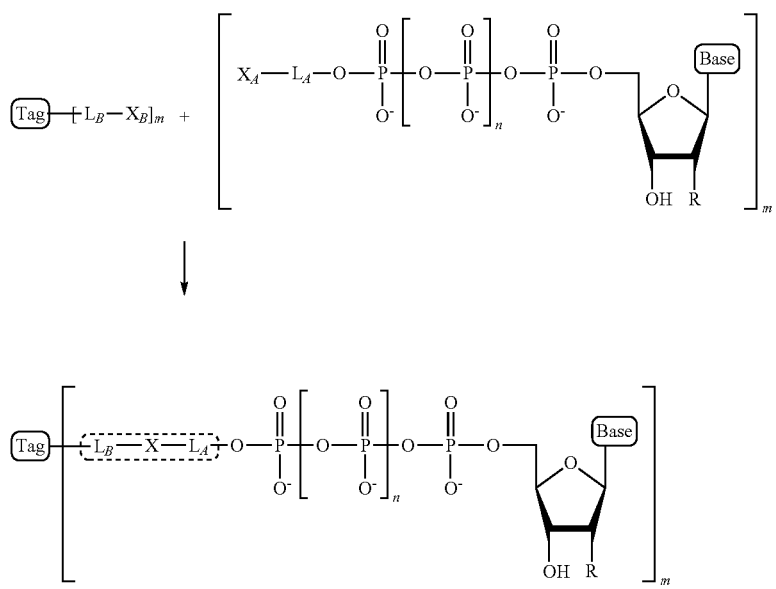

Scheme 1

As depicted in Scheme 1, $X_A$ and $X_B$ are the reactive linker forming groups, and $L_A$ and $L_B$, are chemical moieties that are precursor linkers to the finally formed linkers of structure -$L_B$-X-$L_A$-. Thus, $X_A$ and $X_B$ are chemical moieties which are capable of undergoing a chemical reaction that results in a covalent coupling between one of the multiple nucleotide and the tag. As in the structure of formula II, the large brackets with subscript m are used to indicate that from 2 to 12 of the reactive moieties within the brackets are present in the reaction. Accordingly the resulting product comprises m linkers of structure -$L_B$-X-$L_A$-coupling m nucleotide moieties to a single tag. The product of each covalent coupling reaction between the linker forming groups, $X_A$ and $X_B$, is a linker comprising a general structure -$L_B$-X-$L_A$-. Thus, in some embodiments of the present disclosure, the linker "L" or "Linker" as in the compounds of formula (I) and (II) is a linker of structural formula "-$L_B$-X-$L_A$-" as depicted in Scheme 1. The chemical moiety, "X" (of the "-$L_B$-X-$L_A$-") is the new chemical linker moiety produced in the linker forming reaction. Often, the name of the particular chemical group X is used to denote the type of linker, although the other parts of the linker provided by $L_A$ and $L_B$ may contribute substantially to the overall structure of the linker. For example, a characteristic linker moiety X can be a triazole group. The triazole group can be formed in The chemical moieties, $L_A$ and $L_B$ are chemical groups which can effectively act as linkers or spacers between the nucleotide oligophosphate or the tag and their linker forming groups, $X_A$ and $X_B$. Typically, $L_A$ and $L_B$ are chemical moieties that do not react in the linker forming reaction but which provide additional spacing or structure for the final formed linker. The $L_A$ and $L_B$ moieties can be the same or different. In some embodiments, $L_A$ or $L_B$ can be much longer or shorter than the other, and/or provide different structural features, for example features that result in more or less conformational flexibility. Accordingly, in some embodiments, $L_A$ and $L_B$ moieties useful in the tagged multi-nucleotide compounds of the present disclosure comprise a covalently bonded chain of 2 to 100 atoms, and optionally, one or more chemical moieties selected from the group consisting of: linear ($C_1$-$C_{12}$) alkyl, linear ($C_1$-$C_{12}$) alkene, linear ($C_1$-$C_{12}$) alkyne, ester, ether, thioether, amine, amide, imide, benzene, benzyl ether, phenol, bis-hydroxyethylbenzene, carbonate, carbamate, squarate, thiazole, thiazolidine, hydrazone, oxime, triazole, dihydropyridazine, phosphodiester, polyethylene glycol (PEG), and combinations thereof.

Thus, in some embodiments, the present disclosure provides a tagged multi-nucleotide compound of structural formula (III)

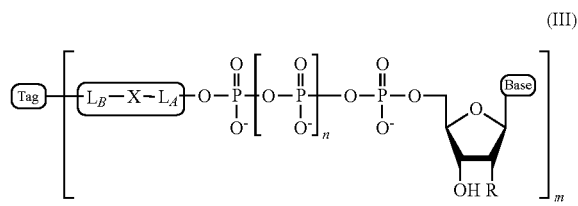

(III)

wherein, "Base" is a naturally occurring or non-naturally occurring nucleobase; R is selected from H and OH; n is from 1 to 10; m is from 2 to 12; Tag is a molecular moiety which is capable of producing a detectable signal; and "-$L_B$-X-$L_A$-" is a linker wherein $L_A$ and $L_B$ each comprise a covalently bonded chain of 2 to 100 atoms and X is a chemical moiety selected from the group consisting of ester, ether, thioether, amine, amide, imide, benzene, benzyl ether, phenol, bis-hydroxyethylbenzene, carbonate, carbamate, squarate, thiazole, thiazolidine, hydrazone, oxime, triazole, and dihydropyridazine. In some embodiments, $L_A$ and $L_B$ each independently comprises a chemical moiety selected from the group consisting of: linear ($C_1$-$C_{12}$) alkyl, linear ($C_1$-$C_{12}$) alkene, linear ($C_1$-$C_{12}$) alkyne, ester, ether, thioether, amine, amide, imide, benzene, benzyl ether, phenol, bis-hydroxyethylbenzene, carbonate, carbamate, squarate, thiazole, thiazolidine, hydrazone, oxime, triazole, dihydropyridazine, phosphodiester, polyethylene glycol (PEG), and combinations thereof.

Exemplary linker forming groups, $X_A$ and $X_B$, linker precursor moieties, $L_A$ and $L_B$ and the resulting linker that they form, of formula -$L_A$-X-$L_B$-, are shown in Table 1, below.

TABLE 1

| $R_1$-$L_A$-$X_A$* | $X_B$-$L_B$-$R_2$* | $R_1$-$L_A$-X-$L_B$-$R_2$*<br>(or $R_1$-Linker-$R_2$) |
|---|---|---|
| (IVa) | (IVb) | (IVc) |
| (Va) | (Vb) | (Vc) |
| (VIa) | (VIb) | (VIc) |
| (VIIa) | (VIIb)<br>wherein, Z is a suitable leaving group, e.g., F, Cl, Br, or I | (VIIc) |
| (VIIIa) | (VIIIb) | (VIIIc) |
| (IXa) | (IXb)<br>wherein, Z is a suitable leaving group, e.g., F, Cl, Br, or I. | (IXc) |

TABLE 1-continued
| $R_1$-$L_A$-$X_A$* | $X_B$-$L_B$-$R_2$* | $R_1$-$L_A$-X-$L_B$-$R_2$*<br>(or $R_1$-Linker-$R_2$) |
|---|---|---|
| 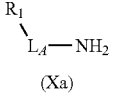<br>(Xa) | 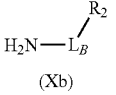<br>(Xb)<br>+<br>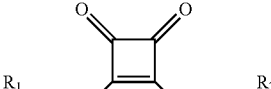 | 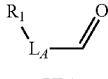<br>(Xc) |
| 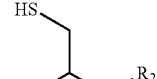<br>(XIa) | 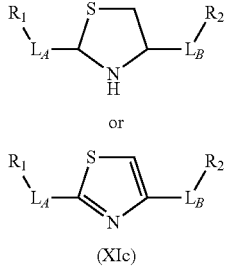<br>(XIb) | 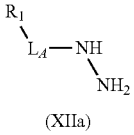<br>or<br>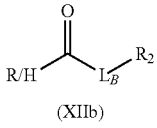<br>(XIc) |
| 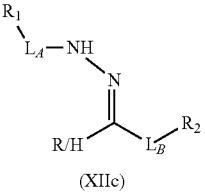<br>(XIIa) | 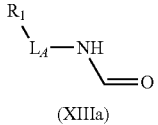<br>(XIIb) | <br>(XIIc) |
| 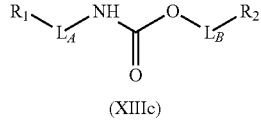<br>(XIIIa) | 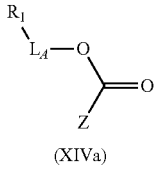<br>(XIIIb) | <br>(XIIIc) |
| 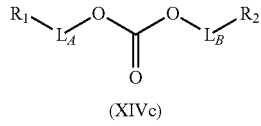<br>(XIVa)<br><br>wherein, Z is a suitable leaving group, e.g., —OSu, —OBt, or —OAt | <br>(XIVb) | 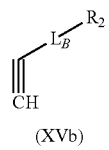<br>(XIVc) |
| 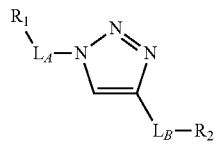<br>(XVa) | (XVb) | (XVc) |

TABLE 1-continued

| $R_1$-$L_A$-$X_A$* | $X_B$-$L_B$-$R_2$* | $R_1$-$L_A$-X-$L_B$-$R_2$*<br>(or $R_1$-Linker-$R_2$) |
|---|---|---|
| <br>(XVIa) | 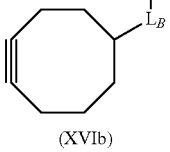<br>(XVIb) | 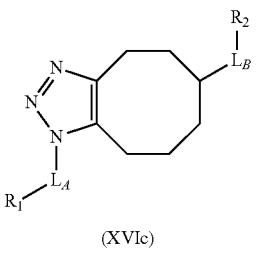<br>(XVIc) |
| 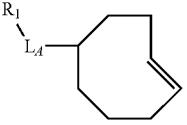<br>(XVIIa) | 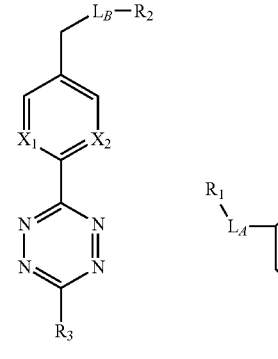<br>(XVIIb)<br>wherein, $X_1$ and $X_2$ are atoms independently selected from C and N; and $R_3$ is a chemical group selected from the group consisting of: H, F, Cl, Br, I, $CH_3$, $CF_3$, $NH_2$, $NO_2$, OH, C(O)OH, C(O)OCH$_3$, C(O)NH$_2$, linear or branched ($C_2$-$C_5$) alkyl, linear or branched ($C_2$-$C_5$) alkenyl, linear or branched ($C_2$-$C_5$) alkynyl, unsubstituted or para-substituted 6-membered aryl ring, and unsubstituted or para-substituted 6-membered heteroaryl ring. | 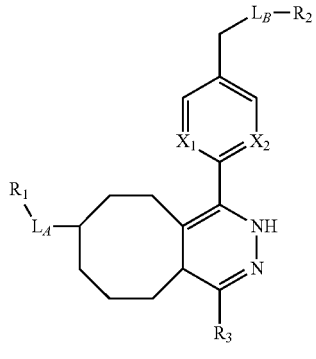<br>(XVIIc)<br>wherein, $X_1$ and $X_2$ are atoms independently selected from C and N; and $R_3$ is a chemical group selected from the group consisting of: H, F, Cl, Br, I, $CH_3$, $CF_3$, $NH_2$, $NO_2$, OH, C(O)OH, C(O)OCH$_3$, C(O)NH$_2$, linear or branched ($C_2$-$C_5$) alkyl, linear or branched ($C_2$-$C_5$) alkenyl, linear or branched ($C_2$-$C_5$) alkynyl, unsubstituted or para-substituted 6-membered aryl ring, and unsubstituted or para-substituted 6-membered heteroaryl ring. |

*$R_1$ and $R_2$ are a tag and nucleotide, respectively, or $R_1$ and $R_2$ are a nucleotide and tag, respectively Table 1 exemplifies range of linkers and the corresponding reactive linker-forming groups that undergo a reaction that results in the covalent coupling linker. These various linkers and reactions are well-known in the art. The ordinary artisan will be able to identify the reagents needed for these reactions and either synthesize them or obtain them commercially. For example, reagents for conjugating or crosslinking polypeptide (or proteins) to other biomolecules can be used as linker forming groups to prepare the tagged multi-nucleotide structures of the present disclosure. (See e.g., catalog of "crosslinking reagents" available from Thermo Scientific, USA at www.piercenet.com or Sigma-Aldrich, USA at www.sigmaaldrich.com). Similarly, terminal phosphate modified nucleosides and/or reagents for such modification with azide or alkyne groups (or other linker forming groups) are commercially available (see e.g., Jena Bioscience Gmbh, Jena, Germany). Additionally, a wide range of FMOC-protected amino acid residues modified with azide or alkyne groups (or other linker forming groups) that can be used in the automated solid-phase synthesis of polypeptides are commercially available (see e.g., AnaSpec, Fremont, Calif., USA). Similarly, It is contemplated that any of the pairs of linker forming groups of structural formulae (IVa)-(XVIIa) and (IVb)-

(XVIIb) can be used in either configuration in preparing a linker in a tagged multi-nucleotide compounds of the present disclosure (e.g., compound of formula (III)). That is, any of the linker forming groups, $X_A$ and $X_B$ can be used on either the tag or the nucleotide, as long as the linker forming groups are paired to provide the linker reaction forming the linker moiety X. Thus, any of the linker forming groups of structural formulae (IVa)-(XVIIIa) could be attached to either the tag or the nucleotide, and the conjugate linker forming group of structural formulae (IVb)-(XVIIb) would be attached to the other. Thus, the groups $R_1$ and $R_2$ as depicted in the linkers of form $R_1$-$L_A$-X-$L_B$-$R_2$ in Table 1, can represent either the tag and the nucleotide, or the nucleotide and the tag, respectively. Accordingly, in some embodiments, the present disclosure provides tagged multi-nucleotide compounds of formula (III), wherein the compound comprises a compound of formula $R_1$-$L_A$-X-$L_B$-$R_2$, wherein $R_1$ and $R_2$ are the nucleotide and the tag, or $R_1$ and $R_2$ are the tag and the nucleotide, respectively, and -$L_A$-X-$L_B$- comprises a chemical moiety selected from the moieties of structural formula (IVc)-(XVIIc) in Table 1.

As described above, the chemical moieties $L_A$ and $L_B$ which make up the linker can each independently comprise chemical moieties including linear ($C_1$-$C_{12}$) alkyl, ester, ether, thioether, amine, amide, imide, benzene, benzyl ether, phenol, bis-hydroxyethylbenzene, carbonate, carbamate, polyethylene glycol (PEG), and combinations thereof. Similar to the linker forming groups $X_A$ and $X_B$, it is contemplated that any of the chemical moieties $L_A$ and $L_B$, which make up the linker, can each independently be used with any of the linker forming groups, and can be used on either the tag or the nucleotide. Additionally, it is contemplated that the chemical moieties $L_A$ and $L_B$ can be the same or different. In some embodiments of the tagged multi-nucleotide compounds of formula (III), the $L_A$ and $L_B$ chemical moieties comprise chemical moieties independently selected from the group consisting of moiety structures of formula (XVIIIa)-formula (XVIIIf) as in Table 2.

TABLE 2

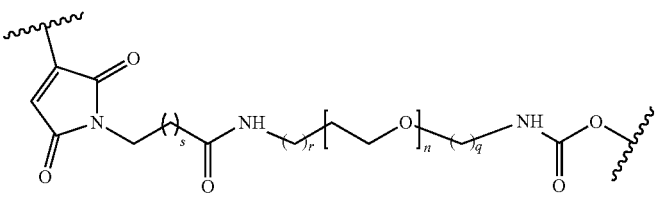

(XVIIIa)

wherein, n = 1 to 50, and q, r, and s each independently = 0, 1, 2, or 3;

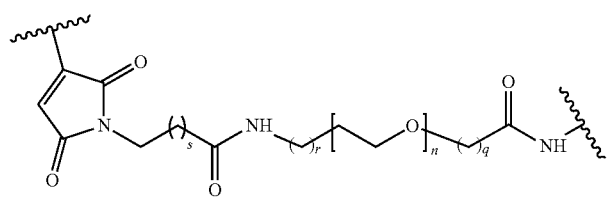

(XVIIIb)

wherein, n = 1 to 50, and q, r, and s each independently = 0, 1, 2, or 3;

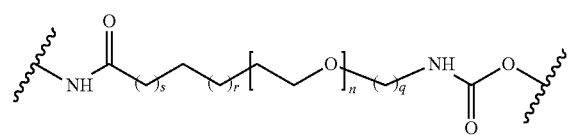

(XVIIIc)

wherein, n = 1 to 50, and q, r, and s each independently = 0, 1, 2, or 3;

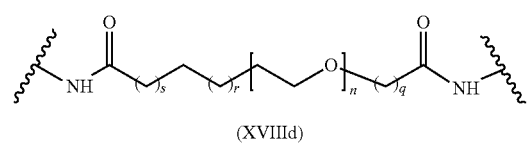

(XVIIId)

wherein, n = 1 to 50, and q, r, and s each independently = 0, 1, 2, or 3.

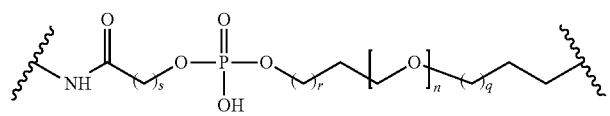

(XVIIIe)

wherein, n = 1 to 50, and q, r, and s each independently = 0, 1, 2, or 3.

TABLE 2-continued

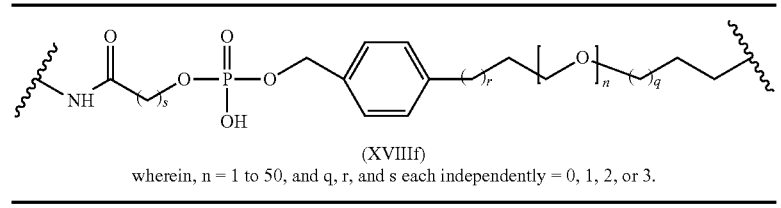

(XVIIIf)

wherein, n = 1 to 50, and q, r, and s each independently = 0, 1, 2, or 3.

Although the structural formula of compound (III) depicts the "-$L_B$-X-$L_A$-" linker that is formed as a moiety separate from the tag, it is contemplated that in some embodiments, the linker can be formed in a reaction with a linker forming group that can comprise part of the tag. For example, the tag can comprise an oligonucleotide, wherein the oligonucleotide includes a monomer unit modified with a propargyl or other alkynyl group which can be covalently coupled to a desired nucleotide (or nucleotide analog) via an azide-alkyne "click" reaction. This propargyl group which could also be considered part of the tag can act as a linker forming group (i.e., "$X_B$") and undergoes a linker forming reaction with a linker forming group attached to a nucleotide.

Branched or Dendrimeric Linkers

In addition to the wide range of linkers having two reactive ends capable of covalent coupling to molecular moieties, the tagged multi-nucleotides of the present disclosure generally include at least one "branched" or "dendrimeric" linker, which is a type of linker moiety that has three or more reactive ends. The use of linkers comprising a branched or dendrimeric linker moiety facilitate the covalent coupling of a single tag to two or more nucleotides. Branched or dendrimeric linker moieties capable of providing three or more reactive ends that can be used in the tagged multi-nucleotide compounds of the present disclosure are well-known in the art. See e.g., Shchepinov et al., "Oligonucleotide dendrimers: synthesis and use as polylabelled DNA probes," *Nucleic Acids Research,* 1997, Vol. 25, No. 22, 4447-4454. Branched or dendrimeric linker moieties providing three or more reactive ends useful in the compounds of the present disclosure are commercially available from various vendors of DNA synthesis reagents, e.g., Glen Research (Virginia, USA; www.glenresearch.com).

Accordingly, in some embodiments the tagged multi-nucleotide compounds of the present disclosure (e.g., structural formula (I) and (II) can comprise a linker, wherein the linker comprises a branched or dendrimeric moiety capable of forming covalent linkages with three or more molecular moieties.

Exemplary reagents useful for preparing tagged multi-nucleotide compound of the present disclosure wherein the linker comprises a branched or dendrimeric moiety include the protected phosphoramidite reagent compounds (19) and (20) shown below.

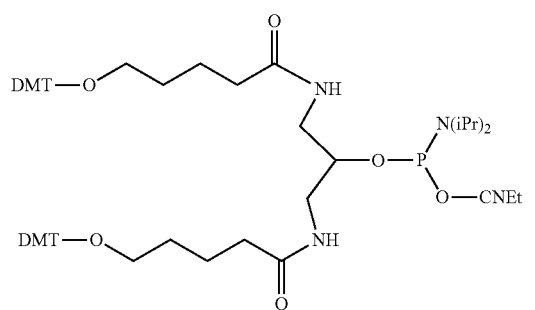

(19)

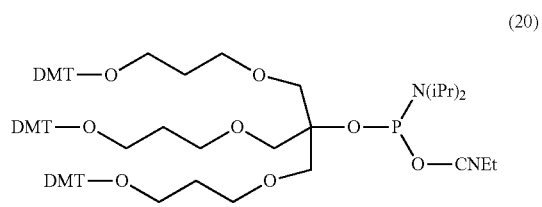

(20)

The branched or dendrimeric phosphoramidite "doubler" and "trebler" units of compounds (19) and (20) are easily attached to the end of oligonucleotide chains to generate a linker end on the oligonucleotide capable of attaching to 2 or more molecular moieties, including additional linkers (e.g., as disclosed elsewhere herein), which can then be attached to terminal oligophosphates of nucleotides. Accordingly, an oligonucleotide comprising natural and/or non-natural monomer units can be used as a tag for generating the tagged multi-nucleotides of the present disclosure.

In some embodiments of the present disclosure, the tagged multi-nucleotide compound comprises a branched or dendrimeric "doubler" linker moiety and has a structural formula (IIIa):

(IIIa)

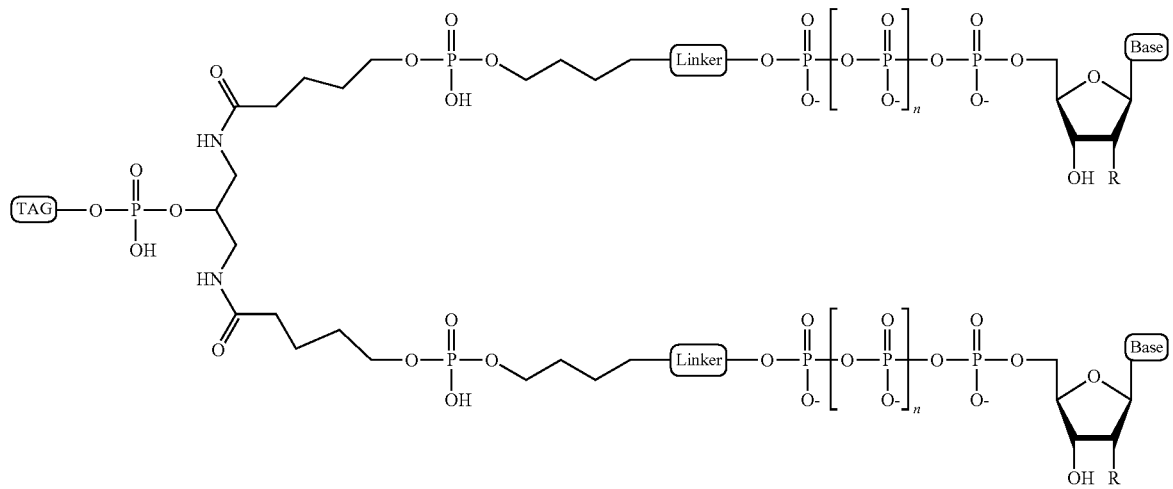

wherein, "Base" is a naturally occurring or non-naturally occurring nucleobase; R is selected from H and OH; n is from 2-12; Linker is a linker comprising a covalently bonded chain of 2 to 100 atoms; and Tag is a molecular moiety which is capable of producing a detectable signal.

In some embodiments of the present disclosure, the tagged multi-nucleotide compound comprises a branched or dendrimeric "trebler" linker moiety and has a structural formula (IIIb):

bonded chain of 2 to 100 atoms; and Tag is a molecular moiety which is capable of producing a detectable signal.

Additionally, two or more of the branched or dendrimeric phosphoramidite "doubler" units of compound (19) and/or the "trebler" units of compound (20) can be combined to create linkers capable of covalent coupling a single molecular moiety (e.g., a tag) to 4, 6, 8, 9, 12, or more nucleotides. Thus, in some embodiments of the present disclosure, the (IIIb)

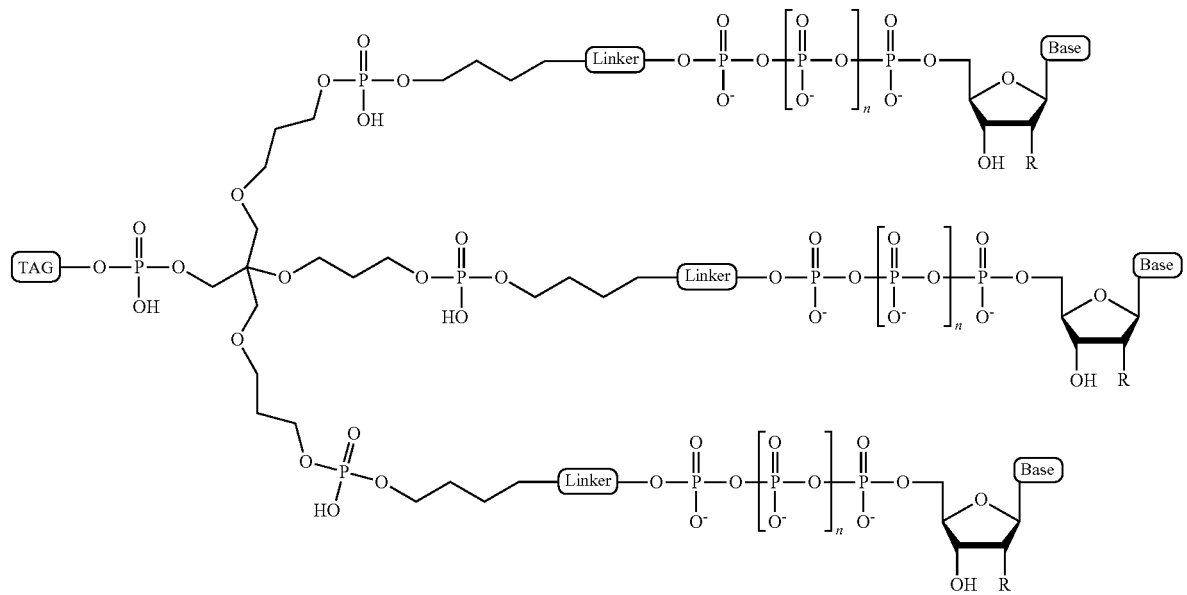

wherein, "Base" is a naturally occurring or non-naturally occurring nucleobase; R is selected from H and OH; n is from 2-12; Linker is a linker comprising a covalently tagged multi-nucleotide compound comprises a branched or dendrimeric quaternary linker moiety comprising two doubler units and has a structural formula (IIIc):

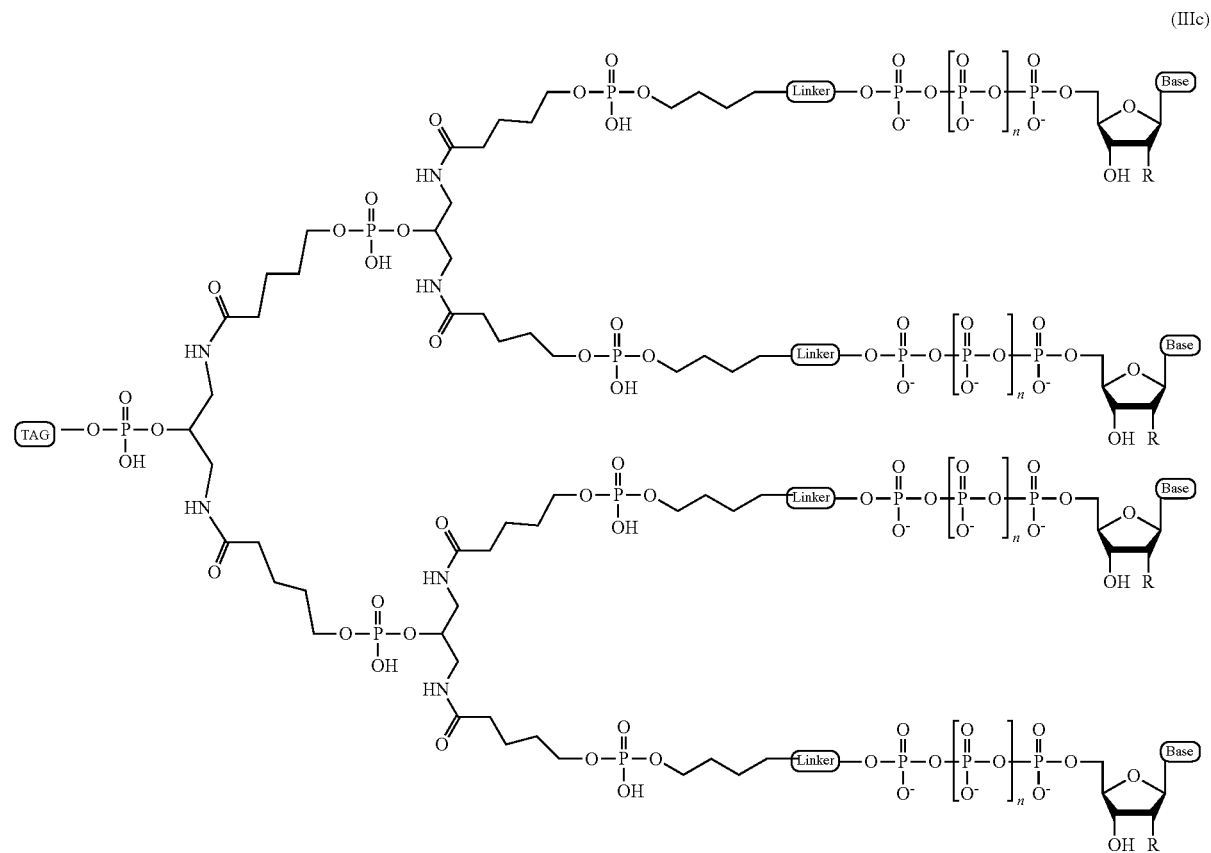

(IIIc)

wherein, "Base" is a naturally occurring or non-naturally occurring nucleobase; R is selected from H and OH; n is from 2-12; Linker is a linker comprising a covalently bonded chain of 2 to 100 atoms; and Tag is a molecular moiety which is capable of producing a detectable signal.

A variety of linkers comprising a range of chemical moieties that are useful in the tagged multi-nucleotide compounds of structural formulas (IIIa), (IIIb), and (IIIc). In some embodiments of the compounds of structural formulas (IIIa), (IIIb), and (IIIc), the linker of 2 to 100 atoms can comprise one or more chemical moieties selected from the group consisting of: linear ($C_1$-$C_{12}$) alkyl, linear ($C_1$-$C_{12}$) alkene, linear ($C_1$-$C_{12}$) alkyne, ester, ether, thioether, amine, amide, imide, benzene, benzyl ether, phenol, bis-hydroxyethylbenzene, carbonate, carbamate, squarate, thiazole, thiazolidine, hydrazone, oxime, triazole, dihydropyridazine, phosphodiester, polyethylene glycol (PEG), and combinations thereof.

In some embodiments of the present disclosure, the linker of the compounds of structural formulas (IIIa), (IIIb), and (IIIc), comprises a triazole group formed in a "click" reaction between an azide linker forming group, and an alkyne linker forming group (e.g., a propargyl group). Accordingly, in some embodiments, the tagged multi-nucleotide compound can have a structural formula (IIId), (IIIe), or (IIIf):

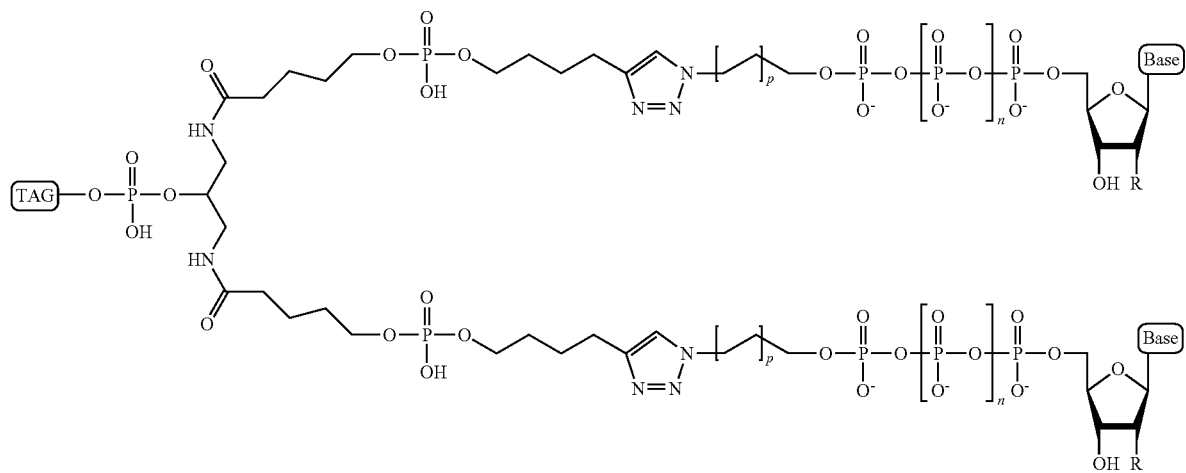
(IIId)
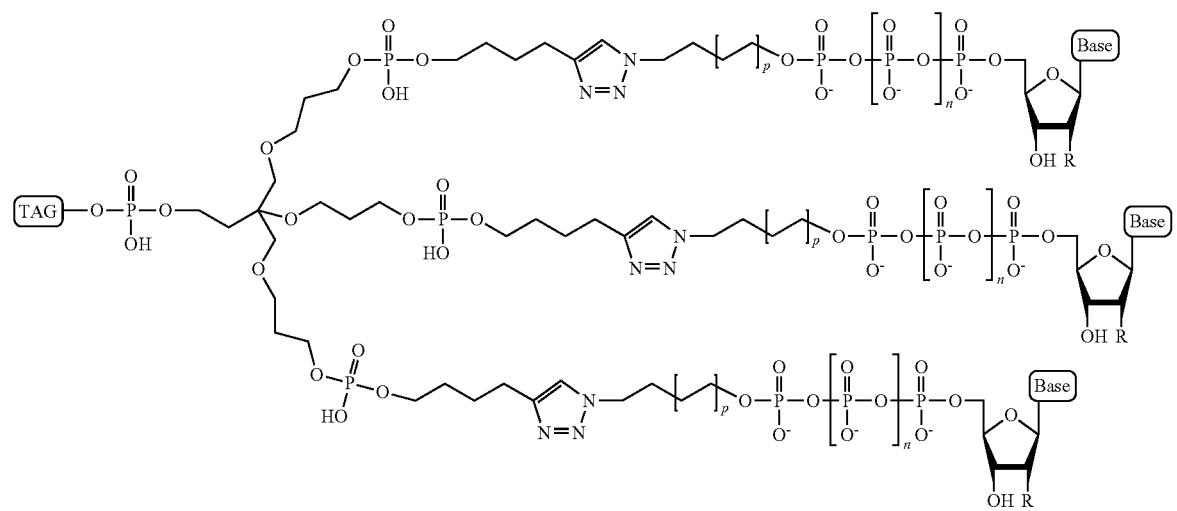
(IIIe)

(IIIf)

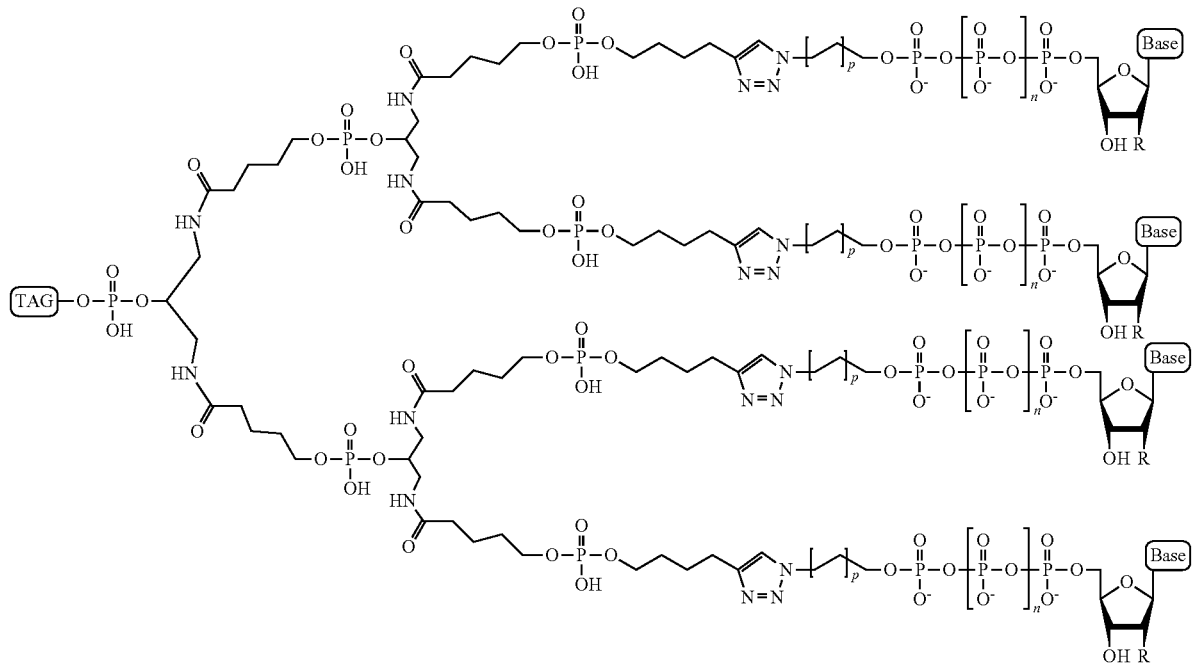

wherein, "Base" is a naturally occurring or non-naturally occurring nucleobase; R is selected from H and OH; n is from 2-12; p is from 2-10; and Tag is a molecular moiety which is capable of producing a detectable signal.

As shown above, in some embodiments of the compounds of structural formulas ((I)f), the branched or or (III), the linker connecting the terminal phosphate of dN6P moiety to the phosphate of the dendrimeric phosphoramidite linker (e.g., a doubler-linker or trebler-linker) comprises a "C11-triazole-C4" linker of formula (XVd) or a "C6-amide-C4-triazole-C4" linker of formula (XVe):

Also, as shown above for the compound of structural formula (IIIf), the branched or dendrimeric phosphoramidite "doubler" unit of compound (19) and the "trebler" unit of compound (20) can be easily combined to create linkers capable of covalent coupling a single molecular moiety (e.g., a tag) to 4, 6, 8, 9, 12, or more nucleotides. For example, a tag can be linked to compound (19) and then compound (20) via standard phosphoramidite synthesis methods to generate compound (21), which is capable of further linking to at least six additional molecular moieties, such as six nucleotides.

(XVd)

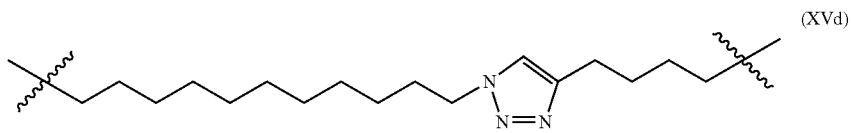

(XVe)

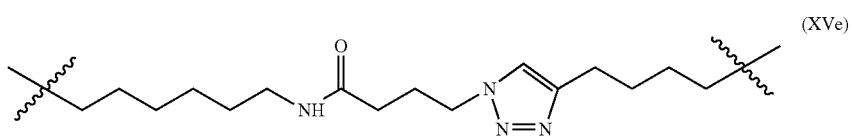

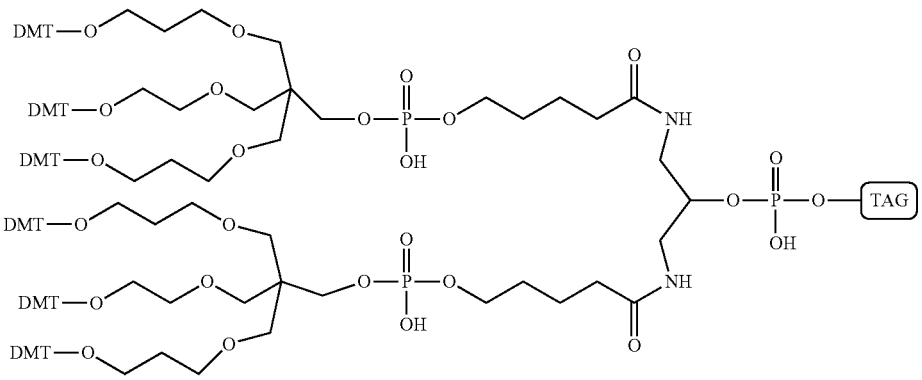

(21)

The three-ended phosphoramidite "doubler" unit of compound (19) can also be prepared (or commercially obtained) with one DMT protecting group and one FMOC protecting group. This "doubler" unit with two different protecting groups can then be used to attach subsequently two different branched or dendrimeric units. For example, a "doubler" unit of compound (19) and a "trebler" unit of compound (20) may be covalently attached in a serial fashion to a "doubler" unit having DMT and Fmoc protecting groups that was previously attached to a single tag. Such a combination provides a single tag with a linker moiety capable of further linking to at least five additional molecular moieties, such as five nucleotides.

The ordinary artisan will immediately recognize that the branched or dendrimeric phosphoramidite units of compounds (19) and (20), or other such branched or dendrimeric linker moieties can be combined in numerous ways to generate tagged multi-nucleotide compounds of the present disclosure.

Tags

Tags useful in the tagged multi-nucleotides of the present disclosure generally can include any molecular moiety that enables or enhances the ability to detect and/or identify, either directly or indirectly, the molecular moiety to which it is coupled (e.g., the nucleotide(s) that are being "tagged"). For example, tags of the present disclosure can include molecular moieties that provide a detectable property or characteristic, such as steric bulk or volume, electrostatic charge, electrochemical potential, optical and/or spectroscopic signature. The selection of a tag structure for use in a tagged multi-nucleotide compound of the present disclosure can be varied depending on the signal to be detected in the desired use of the compound.

In some embodiments, the tagged multi-nucleotides of the present disclosure comprise tags having polymeric structures. Tags having polymeric structures provide a wide range of easily modifiable molecular structures and properties, which allows for a range of detectable signals. Exemplary tags having polymeric structures include, but are not limited to, natural or synthetic polymers, such as polyethylene glycol, oligonucleotides, polypeptides, carbohydrates, peptide nucleic acid polymers, locked nucleic acid polymers, any of which may be optionally modified with or linked to chemical groups, such as dye moieties, or fluorophores. Such polymeric tags have been used as nanopore detectable tags, including polymers of nucleotides (e.g., oligonucleotides), amino acids (e.g., polypeptides), and/or ethylene glycol (e.g., various length PEGs), and found to result in a range of nanopore detectable signals (e.g., blocking currents).

Oligonucleotide Tags

WO2015/148402 (Fuller et al.) discloses a wide range of oligonucleotide-tagged nucleotides and their use in nanopore sequencing. The oligonucleotide-tagged nucleotides disclosed in WO2015/148402 have a single nucleotide covalently linked to a single oligonucleotide moiety, which typically has a length in the range of about 30 monomer units. The disclosed oligonucleotide tags can include naturally occurring DNA nucleotide units dA, dC, dG, and dT and/or a wide range of non-natural monomeric units. Indeed, WO2015/148402 discloses over 100 distinct tag structures comprising oligonucleotides made up of natural and/or non-natural monomer units (i.e., nucleotide analog or spacer units). It is contemplated that the tagged multi-nucleotides of the present disclosure can comprise any of tags disclosed in WO2015/148402. Many oligonucleotide tags useful in the tagged multi-nucleotides of the present disclosure are provided below in Table 3.

TABLE 3

| Tag Name | Tag Structure (using standard automated oligonucleotide synthesis abbreviations) | SEQ ID No. |
|---|---|---|
| -Cy3-dT$_{25}$ | /iCy3/TTTTT TTTTT TTTTT TTTTT TTTTT | 1 |
| -dT*$_{30}$_ODD | T*TT*TT*TT*TT*TT*TT*TT*TT*TT*TT*TT*TT*TT*TT*T | 2 |
| -dT$_{30}$ | TTTTT TTTTT TTTTT TTTTT TTTTT TTTTT | 3 |
| -dT$_6$-dSp$_8$-dT$_{16}$ | TTTTTT/idSp//idSp//idSp//idSp//idSp//idSp//idSp/TTTTT TTTTT TTTTT T | 4 |
| -dT$_6$-dT*$_{10}$-dT$_{14}$ | TTTTTTT*T*T*T*T*T*T*T*T*T*TTTTT TTTTT TTTT | 5 |
| -dT$_4$-dSp$_3$-dT$_{23}$ | TTTT/idSp//idSp//idSp/TTTTT TTTTT TTTTT TTTTT TTT | 6 |
| -dT$_7$-dSp$_3$-dT$_{20}$ | TTTTT TT/idSp//idSp//idSp/TTTTT TTTTT TTTTT TTTTT TTTTT | 7 |

TABLE 3-continued

| Tag Name | Tag Structure (using standard automated oligenucleotide synthesis abbreviations) | SEQ ID No. |
|---|---|---|
| -dT$_{10}$-dSp$_3$-dT$_{17}$ | TTTTT TTTTT/idSp//idSp/idSp/TTTTT TTTTT TTTTT TT | 8 |
| -dT$_{13}$-dSp$_3$-dT$_{14}$ | TTTTT TTTTT TTT/idSp//idSp//idSp/TTTTT TTTTT TTTT | 9 |
| -dT$_{30}$-C6 | TTTTT TTTTT TTTTT TTTTT TTTTT TTTTT/3C6/ | 10 |
| -Cy3-dT$_{30}$-C6 | /iCy3/TTTTT TTTTT TTTTT TTTTT TTTTT TTTTT/3C6/ | 11 |
| -dT$_4$-dSp$_{10}$-dT$_{16}$-C6 | TTTT/idSp//idSp//idSp//idSp//idSp//idSp//idSp//idSp//idSp//idSp/TTT TT TTTTT TTTTT T/3C6/ | 12 |
| -(dT$_4$-Npy$_2$)$_6$-C3 | TTTT/Npy//Npy/TTTT/Npy//Npy/TTTT/Npy//Npy/TTTT/Npy//Npy/TT TT/Npy//Npy/TTTT/Npy//Npy/3SpC3/ | 13 |
| -(dT$_4$-Neb$_2$)$_6$-C3 | TTTT/Neb//Neb/TTTT/Neb//Neb/TTTT/Neb//Neb/TTTT/Neb//Neb/T TTT/Neb//Neb/TTTT/Neb//Neb/3SpC3/ | 14 |
| -dT$_4$-Sp18-dT$_{22}$-C3 | TTTT/iSp18/TTTTT TTTTT TTTTT TTTTT TT/3SpC3/ | 15 |
| -dT$_4$-(Sp18)$_2$-dT$_{19}$-C3 | TTTT/iSp18//iSp18/TTTTT TTTTT TTTTT TTTT/3SpC3/ | 16 |
| -dT$_4$-(Sp9)$_2$-dT$_{22}$-C3 | TTTT/iSp9//iSp9/TTTTT TTTTT TTTTT TTTTT TT/3SpC3/ | 17 |
| -dT$_6$-(UniAmM)$_6$-dT$_{18}$-C3 | TTTTtT/iUniAmM//iUniAmM//iUniAmM//iUniAmM//iUniAmM//iUniAmM/TTTT TTTTT TTTTT TTT/3SpC3/ | 18 |
| -dT$_6$-(Pyrd)$_6$-dT$_{18}$-C3 | TTTTTT/Pyrd//Pyrd//Pyrd//Pyrd//Pyrd/TTTT TTTTT TTTTT TTTT/3SpC3/ | 19 |
| -dT$_6$-(AmMC6T)$_6$-dT$_{18}$-C3 | TTTTTT/iAmMC6T//iAmMC6T//iAmMC6T//iAmMC6T//iAmMC6T//iAmMC6T/TTTT TTTTT TTTTT TTTT/3SpC3/ | 20 |
| -dT$_4$-Spermine-dT$_{22}$-C3 | TTTT/Spermine/TTTTT TTTTT TTTTT TTTTT TT/3SpC3/ | 21 |
| -dT$_4$-Spermine-(dSp)$_3$-dT$_{19}$-C3 | TTTT/Spermine//idSp//idSp/idSp/TT TTTTT TTTTT TTTTT TT/3SpC3/ | 22 |
| -dT$_4$-Spermine-iFlrT-dT$_{21}$-C3 | TTTT/Spermine//iFluorT/TTTT TTTTT TTTTT TTTTT TT/3SpC3/ | 23 |
| -Spermine-dT$_{30}$-C3 | /Spermine/TTTTT TTTTT TTTTT TTTTT TTTTT TTTTT/3SpC3/ | 24 |
| -Cy3.5-dT$_{30}$-C3 | iCy3.5/TTTTT TTTTT TTTTT TTTTT TTTTT TTTTT/3SpC3/ | 25 |
| -Cy-Cy3-dT$_{30}$-C3 | iCy3//iCy3/TTTTT TTTTT TTTTT TTTTT TTTTT TTTTT/3SpC3/ | 26 |
| -dT$_6$-Cy3-dT$_{23}$-C3 | TTTTT T/iCy3/TTTTT TTTTT TTTTT TTTTT TTT/3SpC3/ | 27 |
| -dT$_{10}$-Cy3-dT$_{19}$-C3 | TTTTT TTTTT/iCy3/TTTTT TTTTT TTTTT/3SpC3/ | 28 |
| -Hairpin Block | TT TTC GGC GCG TAA GCG CCG TTT TTT TTT TTT TTT TTT | 29 |
| -T$_6$-(dSp)$_8$-dT$_{16}$-C3 | TTTTTT/idSp//idSp//idSp//idSp//idSp//idSp//idSp/TTTTT TTTTT TTTTT T/3SpC3/ | 30 |
| -Cy3-dT*$_{30}$_ODD | /iCy3/T*TT*TT*T*TT*TT*TT*TT*TT*TT*TT*TT*T*TT*T | 31 |
| -dT*$_{30}$ | T*T*T*T*T*T*T*T*T*T* T*T*T*T*T* T*T*T*T*T* T*T*T*T*T* T*T*T*T*T | 32 |
| -Cy3-dT*$_{30}$ | /iCy3/T*T*T*T*T* T*T*T*T*T* T*T*T*T*T* T*T*T*T*T* T*T*T*T*T* T*T*T*T*T | 33 |
| -Cy3-dT$_{30}$-C3 | /iCy3/TTTTT TTTTT TTTTT TTTTT TTTTT TTTTT/3SpC3/ | 34 |
| -Cy3-dT$_{15}$-C3 | /iCy3/TTTTT TTTTT TTTTT/3SpC3/ | 35 |
| -Cy3-dT$_{20}$-C3 | /iCy3/TTTTT TTTTT TTTTT TTTTT/3SpC3/ | 36 |
| -Cy3-dT$_{25}$-C3 | /iCy3/TTTTT TTTTT TTTTT TTTTT TTTTT/3SpC3/ | 37 |
| -Cy3-dT$_2$-Sp18-T$_{22}$-C3 | /iCy3/TT/iSP18/TTTTT TTTTT TTTTT TTTTT TT/3SpC3/ | 38 |
| -Cy3-dT$_4$-(dSp)$_8$-T$_{18}$-C3 | /iCy3/TTTT/idSp//idSp//idSp//idSp//idSp//idSp//idSp//TTTTT TTTTT TTTTT TTT/3SpC3/ | 39 |
| -Hex-dT$_6$-(AmMC2T)$_6$-dT$_{18}$-C3 | TTTTTT/iAmMC2T//iAmMC2T//iAmMC2T//iAmMC2T//iAmMC2T//iAmMC2T/TTTTT TTTTT TTTTT TTT/3SpC3/ | 40 |
| -Cy3-dT$_4$-Sp9-T$_{23}$-C3 | /iCy3/TTTT/iSP9/TTTTT TTTTT TTTTT TTTTT TTT/3SpC3/ | 41 |
| -Cy3-dT-(dSp)$_3$-dT$_{26}$-C3 | /iCy3/T/idSp//idSp//idSp/T TTTTT TTTTT TTTTT TTTTT TTTTT/3SpC3/ | 42 |
| -Cy3-dT$_4$-(dSp)$_3$-dT$_{23}$-C3 | /iCy3/TTTT/idSp//idSp//idSp/TTT TTTTT TTTTT TTTTT TTTTT/3SpC3/ | 43 |
| -Cy3-dT$_7$-(dSp)$_3$-dT$_{20}$-C3 | /iCy3/TTTTT TT/idSp//idSp//idSp/TTTTT TTTTT TTTTT TTTTT/3SpC3/ | 44 |
| -Cy3-dT$_{10}$-(dSp)$_3$-dT$_{17}$-C3 | /iCy3/TTTTT TTTTT/idSp//idSp//idSp/TTTTT TTTTT TTTTT TT/3SpC3/ | 45 |
| -Cy3-dT$_4$-(iFluorT)$_3$-dT$_{23}$-C3 | /iCy3/TTTT/iFluorT//iFluorT//iFluorT/TTT TTTTT TTTTT TTTTT/3SpC3/ | 46 |
| -Cy3-dT$_4$-iFluorT-dT-iFlourT-dT$_{23}$-C3 | /iCy3/TTTT/iFluorT/T/iFluorT/TTT TTTTT TTTTT TTTTT/3SpC3/ | 47 |
| -dT$_{30}$-Cy3-C3 | TTTTT TTTTT TTTTT TTTTT TTTTT TTTTT/iCy3//3SpC3/ | 48 |
| -dT$_8$-Spermine-dT$_{20}$-C3 | TTTTT TTT/Spermine/TTTTT TTTTT TTTTT TTTTT/3SpC3/ | 49 |
| -Cy3-dT$_4$-Aptamer-dT$_{25}$-C3 | /iCy3/TTT TGG TTG GTG TGG TTG GTT TTT TTT TTT TTT TTT TTT TTT TT/3SpC3/ | 50 |
| -Cy3-dT$_4$-12Hairpin-dT$_{25}$-C3 | /iCy3/TTT TCC GGC GCG GCG CGT AAG CGC CGC GCC GGT TTT TTT TTT TTT TTT TTT TTT TTT/3SpC3/ | 51 |
| -Cy3-dT$_5$-(dSp)$_3$-dT$_{22}$-C3 | /iCy3/TTT TT/idSp//idSp/idSp/T TTT TTT TTT TTT TTT TTT TTT TTT/3SpC3/ | 52 |

TABLE 3-continued

| Tag Name | Tag Structure (using standard automated oligenucleotide synthesis abbreviations) | SEQ ID No. |
|---|---|---|
| -Cy3-dT$_6$-(dSp)$_3$-dT$_{21}$-C3 | /iCy3/TTT TTT/idSp//idSp/idSp/TTT TTT TTT TTT TTT TTT TTT /3SpC3/ | 53 |
| -Cy3-dT$_4$-(dSp)$_4$-dT$_{22}$-C3 | /iCy3/TTT T/idSp//idSp//idSp/TT TTT TTT TTT TTT TTT TTT TT/3SpC3/ | 54 |
| -Cy3-dT$_4$-(dSp)$_5$-dT$_{21}$-C3 | /iCy3/TTTT/idSp//idSp//idSp//idSp/T TTT TTT TTT TTT TTT TT/3SpC3/ | 55 |
| -Cy3-dT$_5$-SpC12-dT$_{23}$-C3 | /iCy3/TTTTT/iSpC12/TTTTT TTTTT TTTTT TTTTT TTT/3SpC3/ | 56 |
| -Cy3-dT$_4$-SpC6-SpC6-dT$_{24}$-C3 | /iCy3/TTTT/iSpC6//iSpC6/T TTTTT TTTTT TTTTT TTTTT TTT/3SpC3/ | 57 |
| -Cy3-dT$_4$-(SpC3)$_3$-dT$_{23}$-C3 | /iCy3/TTTT/iSpC3//iSpC3//iSpC3/TT TTT TTT TTT TTT TTT TTT TTT /3SpC3/ | 58 |
| -Cy3-dT$_2$-(dSp)$_8$-dT$_{20}$-C3 | /iCy3/TT/idSp//idSp//idSp//idSp//idSp//idSp//idSp//idSp/TTT TTT TTT TTT TT/3SpC3/ | 59 |
| -Cy3-dT$_{30}$-(SpC$_3$)$_4$-PO$_4$ | /iCy3/TTT TTT TTT TTT TTT TTT TTT TTT TTT TTT/iSpC3//iSpC3//iSpC3//iSpC3//3Phos/ | 60 |
| -Cy3-dT$_{30}$-PO$_4$ | /iCy3/TTT TTT TTT TTT TTT TTT TTT TTT TTT TTT/3Phos/ | 61 |
| -Cy3-T$_{30}$-C3-NH$_2$ | /iCy3/TTT TTT TTT TTT TTT TTT TTT TTT TTT TTT/3Propylamine/ | 62 |
| Rev-P-T$_{30}$-Cy3- | /5Phos/TTTTT TTTTT TTTTT TTTTT TTTTT TTTTT/iCy3//3'-propylamine/ + propargyl-propionamide | 63 |
| Rev-P-T$_{24}$-(dSp)$_3$-T$_3$-Cy3- | /5Phos/TTTTT TTTTT TTTTT TTTTT TTTTT TTTT/idSp//idSp//idSp/TTT/iCy3//3'-propylamine/ + propargyl-propionamide | 64 |
| -Cy3-dT$_4$-HP6-dT$_{25}$-C3 | /iCy3/TT TTC GGC GCG TAA GCG CCG TTT TTT TTT TTT TTT TTT TTT T/3SpC3/ | 65 |
| -Cy3-dC$_{30}$-C3 | /iCy3/CCCCCCCCCCCCCCCCCCCCCCCCCCCCCC/3SpC3/ | 66 |
| -Cy3-dT$_4$-(ideoxyl)$_6$-dT$_{20}$-C3 | /iCy3/TTT T/ideoxyl//ideoxyl//ideoxyl//ideoxyl//ideoxyl//ideoxyl/TT TTT TTT TTT TTT TTT TTT /3SpC3/ | 67 |
| -Cy3-dT$_4$-(i5NitInd)$_6$-dT$_{20}$-C3 | /iCy3/TTT T/i5NitInd//i5NitInd//i5NitInd//i5NitInd//i5NitInd//i5NitInd/TT TTT TTT TTT TTT TTT/3SpC3/ | 68 |
| -Cy3-dT$_4$-dC$_6$-dT$_{20}$-C3 | /iCy3/TTTT CCCCCC TTTTT TTTTT TTTTT TTTTT/3SpC3/ | 69 |
| -Cy3-dT$_4$-(i5I-dU)$_6$-dT$_{20}$-C3 | /iCy3/TTT T/i5I-dU//i5I-dU//i5I-dU//i5I-dU//i5I-dU//i5I-dU/TT TTT TTT TTT TTT TTT /3SpC3/ | 70 |
| -Cy3-dT$_4$-(i5Pyrene-dU)$_6$-dT$_{20}$-C3 | /iCy3/TTT T/i5Pyrene-dU//i5Pyrene-dU//i5Pyrene-dU//i5Pyrene-dU//i5Pyrene-dU/TT TTT TTT TTT TTT TTT TTT/3SpC3/ | 71 |
| -Cy3-dT$_4$-(idSP-dT)$_4$-dT$_{18}$-C3 | /iCy3/TTTT/idSp/T/idSp/T/idSp/T/idSp/TTT TTTTT TTTTT TTTTT/3SpC3/ | 72 |
| -Cy3-dT$_5$-(idSP-dT)$_4$-dT$_{17}$-C3 | /iCy3/TTTTT/idSp/T/idSp/T/idSp/T/idSp/TT TTTTT TTTTT TTTTT/3SpC3/ | 73 |
| -Cy3-dT$_4$-(C3)$_6$-dT$_{20}$-C3 | /iCy3/TTTT/iSpC3//iSpC3//iSpC3//iSpC3//iSpC3//iSpC3/TT TTT TTT TTT TTT TTT TTT/3SpC3/ | 74 |
| -Cy3- ($_L$dT)$_{30}$-C3 | /iCy3/($_L$dT)$_{30}$/3SpC3/ | 75 |
| -Cy3-($_L$dT)$_4$-dSp$_3$-($_L$dT)$_{23}$-C3 | /iCy3/($_L$dT)$_4$/idSp//idSp//idSp/($_L$dT)$_{23}$/3SpC3/ | 76 |
| -Cy3-($_L$dT)$_4$-dSp$_8$-($_L$dT)$_{18}$-C3 | /Cy3/($_L$dT)$_4$/idSp//idSp//idSp//idSp//idSp//idSp//idSp//idSp/($_L$dT)$_{18}$/3SpC3/ | 77 |
| -Cy3-($_L$dT)$_4$-(ideoxyl)$_6$-LdT$_{20}$-C3 | /iCy3/($_L$dT)$_4$/ideoxyl//ideoxyl//ideoxyl//ideoxyl//ideoxyl//ideoxyl/($_L$dT)$_{20}$/3SpC3/ | 78 |
| -Cy3-dT$_4$-L111-dT$_{26}$-C3 | /iCy3/TTTT GGG T GGG T GGG T GGG TTTTTTTTTTTTTTTTTTTTTTTTTT/3SpC3/ | 79 |
| -Cy3-dT$_4$-L121-dT$_{26}$-C3 | /iCy3/TTTT GGG T GGG TT GGG T GGG TTTTTTTTTTTTTTTTTTTTTTTTTT/3SpC3/ | 80 |
| -Cy3-dT$_4$-SpC12-SpC12-dT$_{24}$-C3 | /iCy3/TTTT /iSpC12//iSpC12/TTTTT TTTTT TTTTT TTTTT TTTT/3SpC3/ | 81 |
| -Cy3-dT$_3$-(SpC12)$_3$-dT$_{24}$-C3 | /iCy3/TTT /iSpC12//iSpC12//iSpC12/TTTTT TTTTT TTTTT TTTTT TTTT/3SpC3/ | 82 |
| -Cy3-dT$_4$-(SpC6)$_4$-dT$_{25}$-C3 | /iCy3/TTTT/dSpC6//dSpC6//dSpC6//dSpC6/TTTTT TTTTT TTTTT TTTTT/3SpC3/ | 83 |
| -Cy3-dT$_4$-(SpC6)$_5$-dT$_{23}$-C3 | /Cy3/TTTT/dSpC6//dSpC6//dSpC6//dSpC6/TTT TTTTT TTTTT TTTTT TTTTT/3SpC3/ | 84 |
| -Cy3-dT$_5$-(SpC6)$_4$-dT$_{24}$-C3 | /iCy3/TTTTT/dSpC6//dSpC6//dSpC6//dSpC6/TTTTT TTTTT TTTTT TTTTT/3SpC3/ | 85 |
| -Cy3-dT$_2$-(SpC6)$_5$-dT$_{25}$-C3 | /iCy3/TT/dSpC6//dSpC6//dSpC6//dSpC6//dSpC6/TTTTT TTTTT TTTTT TTTTT TTTTT/3SpC3/ | 86 |
| -Cy3-dT$_4$-Spermine-dT$_{25}$-C3 | /iCy3/TTTT/Spermine/TTTTT TTTTT TTTTT TTTTT TTTTT/3SpC3/ | 87 |
| -Cy3-dT$_2$-Spermine-dT$_{27}$-C3 | /iCy3/TT/Spermine/TTTTT TTTTT TTTTT TTTTT TTTTT TT/3SpC3/ | 88 |
| -Cy3-dT$_2$-Spermine-Spermine-dT$_{25}$-C3 | /iCy3/TT/Spermine//Spermine/TTTTT TTTTT TTTTT TTTTT TTTTT T/3SpC3/ | 89 |
| -Cy3-dT$_4$-(i5Pyrene- | /iCy3/TTT T/i5Pyrene-dU/TT/i5Pyrene-dU/TTT TTT TTT TTT | 90 |

TABLE 3-continued

| Tag Name | Tag Structure (using standard automated oligenucleotide synthesis abbreviations) | SEQ ID No. |
|---|---|---|
| dU)-dT$_2$-(i5Pyrene-dU)-dT$_{22}$-C3 | TTT TTT TTT T/3SpC3/ | |
| -Cy3-dT$_4$-(dTmp)$_6$-dT$_{20}$-C3 | /iCy3/TTTT/dT(mp)//dT(mp)//dT(mp)//dT(mp)//dT(mp)//dT(mp)/ TTTTTTTTTTTTTTTTTTTT/3SpC3/ | 91 |
| -Cy3-dT$_4$-(Pyrrolidine)$_6$-dT$_{20}$-C3 | /iCy3/TTTT/{Pyrrolidine}//{Pyrrolidine}//{Pyrrolidine}//{Pyrrolidine}//{Pyrrolidine}//{Pyrrolidine}/TTTTT TTTTT TTTTT TTTTT/3SpC3/ | 92 |
| -Pyrrolidine-dT$_{30}$-C3 | /{Pyrrolidine}/TTTTT TTTTT TTTTT TTTTT TTTTT TTTTT/3SpC3/ | 93 |
| -Pyrrolidine-Pyrrolidine-dT$_{30}$-C3 | /{Pyrrolidine}//{Pyrrolidine}/TTTTT TTTTT TTTTT TTTTT TTTTT TTTTT/3SpC3/ | 94 |
| -(Pyrrolidine)$_3$-dT$_{30}$-C3 | /{Pyrrolidine}//{Pyrrolidine}//{Pyrrolidine}/TTTTT TTTTT TTTTT TTTTT TTTTT TTTTT/3SpC3/ | 95 |
| -SpC3-Cy3-dT$_{30}$-C3 | /iSpC3//iCy3/TTTTT TTTTT TTTTT TTTTT TTTTT TTTTT/3SpC3/ | 96 |
| -SpC3-SpC3-Cy3-dT$_{30}$-C3 | /iSpC3//iSpC3//iCy3/TTTTT TTTTT TTTTT TTTTT TTTTT TTTTT/3SpC3/ | 97 |
| -SpC6-Cy3-dT$_{30}$-C3 | /iSpC6//iCy3/TTTTT TTTTT TTTTT TTTTT TTTTT TTTTT/3SpC3/ | 98 |
| -Cy3-dT$_4$(alpha-dT)$_3$-dT$_{23}$-C3 | /iCy3/TTTT/alpha-dT//alpha-dT//alpha-dT/TTTTT TTTTT TTTTT TTTTT TTT/3SpC3/ | 99 |
| -Cy3-(N3CET)$_{30}$-C3 | /iCy3/N3CET//N3CET//N3CET//N3CET//N3CET//N3CET//N3CET//N3CET//N3CET//N3CET//N3CET//N3CET//N3CET//N3CET//N3CET//N3CET//N3CET//N3CET//N3CET//N3CET//N3CET//N3CET//N3CET//N3CET//N3CET//N3CET//N3CET//N3CET//N3CET//N3CET//3SpC3/ | 100 |
| -dT$_{30}$-C3 | /TTTTT TTTTT TTTTT TTTTT TTTTT TTTTT/3SpC3/ | 101 |
| -Cy3-dT$_4$-(N3CET)$_3$-dT$_{23}$-C3 | /iCy3/TTTT/N3CET//N3CET//N3CET/TTTTT TTTTT TTTTT TTTTT TTT/3SpC3/ | 102 |
| -dT$_6$-(dTmp)$_6$-dT$_{18}$-C3 | /TTTTT T/dT(mp)//dT(mp)//dT(mp)//dT(mp)//dT(mp)//dT(mp)/TTTTT TTTTT TTTTT TTT/3SpC3/ | 103 |
| -dT$_4$-(dSp-dT)$_4$-dT$_8$-C3 | /TTTT/idSp/T/idSp/T/idSp/T/idSp/T TTTT TTTT/3SpC3/ | 104 |
| -dT$_{20}$-C3 | /TTTTT TTTTT TTTTT TTTTT/3SpC3/ | 105 |
| dT$_4$-(N3CET)$_3$-dT$_{13}$-C3 | /TTTT/N3CET//N3CET//N3CET/TTTTT TTTTT TTT/3SpC3/ | 106 |
| -dT$_6$-(dTmp)$_6$-dT$_8$-C3 | /TTTTT T/dT(mp)//dT(mp)//dT(mp)//dT(mp)//dT(mp)//dT(mp)/TTTTT TTT/3SpC3/ | 107 |
| -Cy3-dT$_5$-(BHEB)-dT$_{24}$-C3 | /iCy3/TTTTT/BHEB/TTTTT TTTTT TTTTT TTTTT TTTT/3SpC3/ | 108 |
| -dT$_5$-(BHEB)-dT$_{14}$-C3 | /TTTTT/BHEB/TTTTT TTTTT TTTT/3SpC3/ | 109 |

Selected abbreviations
"*" = thiophosphate diester
"ODD" = thiophosphates only at odd-numbered linkages in sequence
"idSp" = furan amidite (abasic amidite)
"3C6" = 3'-hexanol
"Npy" = 3-nitropyrrole
"3SpC3" = 3'-propanol
"Neb" = nebularine
"iSp18" = polyethyleneglycol 18 atom length
"iSp9" = polyethyleneglycol 9 atom length
"UniAmM" = heptylamine amidite
"Pyrd" = pyrrolidine amidite"
"iAmMC6T" = aminohexyl dT amidite
"iFluorT" = fluorescein dT amidite
"iAmMC2T" = aminoethyl dT amidite
"iSpC12" = dodecyl amidite
"iSpC6" = hexyl amidite
"iSpC3" = propyl amidite
"Rev" = oligonucleotide tag has 5'-phosphate and is linked to nucleotide hexaphosphate via its 3'-end
"HP6" = hairpin structure
"ideoxyl" = 2'-deoxyinosine
"i5NitInd" = 5-nitroindole
"i5I-dU" = 5-iodo deoxyuridine
"i5Pyrene-dU" = 5-pyrene-deoxyuridine
"$_L$dT" = L isomer of thymidine
"L111" = G-quadraplex structure
"L121" = G-quadraplex structure
"dT(mp)" = thymidine methyl phosphonate
"{pyrrolidine}" = pyrrolidine amidite
"alpha-dT" = alpha anomer of thymidine
"N3CET" = 3-N-cyanoethyl-dT amidite (dT with a cyanoethyl group at position N3 of the base)
"BHEB" = bis-hydroxyethylbenzene, which is a spacer having that provides the following structure in the phosphodiester chain of the oligonucleotide:

TABLE 3-continued

| Tag Name | Tag Structure (using standard automated oligenucleotide synthesis abbreviations) | SEQ ID No. |
|---|---|---|
| | 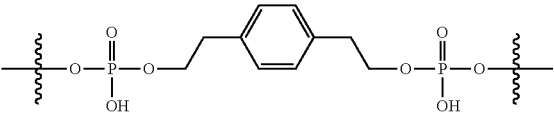 [SMILES: *OP(=O)(O)OCCc1ccc(CCOP(=O)(O)O*)cc1] | |

It is contemplated that the tagged multi-nucleotides of the present disclosure can comprise tags disclosed above in Table 3.

As described herein, a wide variety of natural nucleotide, non-natural nucleotide analog, or synthetic spacer monomer units are available and can be used in synthesizing the tags having polymeric structures useful in the tagged multi-nucleotides of the present disclosure. Generally, these tags are easily synthesized into a tag polymer via amidite coupling chemistry.

Table 4 (below) lists over 300 exemplary amidite reagents (e.g., phosphoramidite or phosphonamidite) that can be used to synthesize tags useful in the tagged multi-nucleotides of the present disclosure. Each of the amidite reagents in Table 4 is commercially available, however, there are hundreds, if not thousands, more amidite reagents having nucleotide analog structures that have been published and would be available to the skilled artisan for use in preparing tags having polymeric structures.

TABLE 4

| Amidite Reagent | Catalog No. |
|---|---|
| Commercially available from: Glen Research, 22825 Davis Drive, Sterling, VA, USA | |
| dA-5'-CE phosphoramidite | 10-0001 |
| dC-5'-CE phosphoramidite | 10-0101 |
| dT-5'-CE phosphoramidite | 10-0301 |
| 7-Deaza-dA-CE phosphoramidite | 10-1001 |
| N6-Me-dA-CE phosphoramidite | 10-1003 |
| 3'-dA-CE phosphoramidite | 10-1004 |
| Etheno-dA-CE phosphoramidite | 10-1006 |
| 8-Br-dA-CE phosphoramidite | 10-1007 |
| 8-oxo-dA-CE phosphoramidite | 10-1008 |
| pdC-CE phosphoramidite | 10-1014 |
| TMP-F-dU-CE phosphoramidite | 10-1016 |
| Pyrrolo-dC-CE phosphoramidite | 10-1017 |
| 5-Me-dC Brancher phosphoramidite | 10-1018 |
| Amino-Modifier C6 dC | 10-1019 |
| 7-deaza-dG-CE phosphoramidite | 10-1021 |
| 8-Br-dG-CE phosphoramidite | 10-1027 |
| 8-oxo-dG-CE phosphoramidite | 10-1028 |
| dmf-dG-CE phosphoramidite | 10-1029 |
| 5'-OMe-dT-CE phosphoramidite | 10-1031 |
| O4-Me-dT-CE phosphoramidite | 10-1032 |
| 4-Thio-dT-CE phosphoramidite | 10-1034 |
| Carboxy-dT | 10-1035 |
| 2-Thio-dT-CE phosphoramidite | 10-1036 |
| Amino-Modifier C2 dT | 10-1037 |
| Biotin-dT | 10-1038 |
| Amino-Modifier C6 dT | 10-1039 |
| dI-CE phosphoramidite | 10-1040 |
| 2'-DeoxyNebularine-CE phosphoramidite (Purine) | 10-1041 |
| O6-Phenyl-dI-CE phosphoramidite | 10-1042 |
| 5-Nitroindole-CE phosphoramidite | 10-1044 |
| 2-Aminopurine-CE phosphoramidite | 10-1046 |
| dP-CE phosphoramidite | 10-1047 |
| dK-CE phosphoramidite | 10-1048 |
| dU-CE phosphoramidite | 10-1050 |
| O4-Triazolyl-dU-CE phosphoramidite | 10-1051 |

TABLE 4-continued

| Amidite Reagent | Catalog No. |
|---|---|
| 4-Thio-dU-CE phosphoramidite | 10-1052 |
| 5-OH-dU-CE phosphoramidite | 10-1053 |
| pdU-CE phosphoramidite | 10-1054 |
| 2'-deoxypseudoU-CE phosphoramidite | 10-1055 |
| Fluorescein-dT phosphoramidite | 10-1056 |
| TAMRA-dT | 10-1057 |
| Dabcyl-dT | 10-1058 |
| EDTA-C2-dT-CE phosphoramidite | 10-1059 |
| 5-Me-dC-CE phosphoramidite | 10-1060 |
| 5-Me-2'-deoxyZebularine-CE phosphoramidite | 10-1061 |
| 5-Hydroxymethyl-dC-CE phosphoramidite | 10-1062 |
| 5-OH-dC-CE phosphoramidite | 10-1063 |
| 3'-dC-CE phosphoramidite | 10-1064 |
| dmf-5-Me-isodC-CE phosphoramidite | 10-1065 |
| 5-Carboxy-dC-CE phosphoramidite | 10-1066 |
| N4-Et-dC-CE phosphoramidite | 10-1068 |
| O6-Me-dG-CE phosphoramidite | 10-1070 |
| 6-thio-dG-CE phosphoramidite | 10-1072 |
| 7-Deaza-8-aza-dG-CE phosphoramidite (PPG) | 10-1073 |
| 3'-dG-CE phosphoramidite | 10-1074 |
| 7-deaza-dX-CE phosphoramidite | 10-1076 |
| dmf-isodG-CE phosphoramidite | 10-1078 |
| 8-Amino-dG-CE phosphoramidite | 10-1079 |
| 5-Br-dC-CE phosphoramidite | 10-1080 |
| 5-I-dC-CE phosphoramidite | 10-1081 |
| 2-F-dI-CE phosphoramidite | 10-1082 |
| 7-deaza-8-aza-dA-CE phosphoramidite | 10-1083 |
| 3'-dT-CE phosphoramidite | 10-1084 |
| 2-Amino-dA-CE phosphoramidite | 10-1085 |
| 8-Amino-dA-CE phosphoramidite | 10-1086 |
| 3-deaza-dA-CE phosphoramidite | 10-1088 |
| Amino-Modifier C6 dA | 10-1089 |
| 5-Br-dU-CE phosphoramidite | 10-1090 |
| 5-I-dU-CE phosphoramidite | 10-1091 |
| 5-F-dU-CE phosphoramidite | 10-1092 |
| 5-Hydroxymethyl-dU-CE phosphoramidite | 10-1093 |
| Thymidine Glycol CE phosphoramidite | 10-1096 |
| AP-dC-CE phosphoramidite | 10-1097 |
| 8,5'-Cyclo-dA CE phosphoramidite | 10-1098 |
| dA-Me phosphonamidite | 10-1100 |
| Ac-dC-Me phosphonamidite | 10-1115 |
| dG-Me phosphonamidite | 10-1120 |
| dT-Me phosphonamidite | 10-1130 |
| dA-PACE phosphoramidite | 10-1140 |
| Ac-dC-PACE phosphoramidite | 10-1150 |
| dG-PACE phosphoramidite | 10-1160 |
| dT-PACE phosphoramidite | 10-1170 |
| dA-H-Phosphonate, TEA Salt | 10-1200 |
| dC-H-Phosphonate, DBU Salt | 10-1210 |
| dG-H-Phosphonate, TEA Salt | 10-1220 |
| dT-H-Phosphonate, TEA Salt | 10-1230 |
| Pac-dA-Me phosphoramidite | 10-1301 |
| Ac-dC-Me phosphoramidite | 10-1315 |
| iPr-Pac-dG-Me phosphoramidite | 10-1321 |
| dT-Me phosphoramidite | 10-1330 |
| CleanAmp ™-Pac-dA-CE phosphoramidite | 10-1440 |
| CleanAmp ™-Ac-dC-CE phosphoramidite | 10-1450 |
| CleanAmp ™-Pac-dG-CE phosphoramidite | 10-1460 |
| CleanAmp ™-dT-CE phosphoramidite | 10-1470 |
| 1-Me-dA-CE phosphoramidite | 10-1501 |
| N6-Ac-N6-Me-dA-CE phosphoramidite | 10-1503 |
| 5-Hydroxymethyl-dC II-CE phosphoramidite | 10-1510 |
| 5-aza-5,6-dihydro-dC-CE phosphoramidite | 10-1511 |

TABLE 4-continued

| Amidite Reagent | Catalog No. |
| --- | --- |
| N4-Ac-N4-Et-dC-CE phosphoramidite | 10-1513 |
| 5-Formyl-dC-CE phosphoramidite | 10-1514 |
| to-CE phosphoramidite | 10-1516 |
| tC°-CE phosphoramidite | 10-1517 |
| tC-nitro-CE phosphoramidite | 10-1518 |
| 8-D-dG-CE phosphoramidite | 10-1520 |
| dDs-CE phosphoramidite | 10-1521 |
| Pac-ds-CE phosphoramidite | 10-1522 |
| dPa-CE phosphoramidite | 10-1523 |
| dDss-CE phosphoramidite | 10-1524 |
| N2-Amino-Modifier C6 dG | 10-1529 |
| 5,6-Dihydro-dT-CE phosphoramidite | 10-1530 |
| N3-Cyanoethyl-dT | 10-1531 |
| 5'-Dabsyl-dT-CE phosphoramidite | 10-1532 |
| N-POM Caged-dT-CE phosphoramidite | 10-1534 |
| NHS-Carboxy-dT | 10-1535 |
| Fmoc Amino-Modifier C6 dT | 10-1536 |
| dX-CE phosphoramidite | 10-1537 |
| S-Bz-Thiol-Modifier C6-dT | 10-1538 |
| DBCO-dT-CE phosphoramidite | 10-1539 |
| C8-Alkyne-dT-CE phosphoramidite | 10-1540 |
| C8-TIPS-Alkyne-dC-CE phosphoramidite | 10-1541 |
| C8-TMS-Alkyne-dC-CE phosphoramidite | 10-1542 |
| C8-Alkyne-dC-CE phosphoramidite | 10-1543 |
| C8-TIPS-Alkyne-dT-CE phosphoramidite | 10-1544 |
| C8-TMS-Alkyne-dT-CE phosphoramidite | 10-1545 |
| 5,6-Dihydro-dU-CE phosphoramidite | 10-1550 |
| 5-Ethynyl-dU-CE phosphoramidite | 10-1554 |
| Ac-5-Me-dC-CE phosphoramidite | 10-1560 |
| 5-Formyl dC III CE phosphoramidite | 10-1564 |
| Ferrocene-dT-CE phosphoramidite | 10-1576 |
| Pyrene-dU-CE phosphoramidite | 10-1590 |
| Perylene-dU-CE phosphoramidite | 10-1591 |
| 8,5'-Cyclo-dG-CE phosphoramidite | 10-1598 |
| Pac-dA-CE phosphoramidite | 10-1601 |
| iPr-Pac-dG-CE phosphoramidite | 10-1621 |
| dA-Thiophosphoramidite | 10-1700 |
| dC-Thiophosphoramidite | 10-1710 |
| dG-Thiophosphoramidite | 10-1720 |
| dT-Thiophosphoramidite | 10-1730 |
| Chemical Phosphorylation Reagent | 10-1900 |
| Chemical Phosphorylation Reagent II | 10-1901 |
| Solid Chemical Phosphorylation Reagent II | 10-1902 |
| 5'-Amino-Modifier 5 | 10-1905 |
| 5'-Amino-Modifier C6 | 10-1906 |
| 5'-DMS(O) MT-Amino-Modifier C6 | 10-1907 |
| 5'-Hexynyl phosphoramidite | 10-1908 |
| Spacer phosphoramidite 9 | 10-1909 |
| 5'-Amino-Modifier C12 | 10-1912 |
| Spacer phosphoramidite C3 | 10-1913 |
| Pyrrolidine-CE phosphoramidite | 10-1915 |
| 5'-Amino-Modifier C6-TFA | 10-1916 |
| 5'-Amino-Modifier TEG CE-phosphoramidite | 10-1917 |
| Spacer phosphoramidite 18 | 10-1918 |
| 5'-Aminooxy-Modifier-11-CE phosphoramidite | 10-1919 |
| Symmetric Doubler phosphoramidite | 10-1920 |
| Trebler phosphoramidite | 10-1922 |
| 5'-Amino-Modifier C3-TFA | 10-1923 |
| Long Trebler phosphoramidite | 10-1925 |
| 5'-Thiol-Modifier C6 | 10-1926 |
| Abasic II phosphoramidite | 10-1927 |
| Spacer C12 CE phosphoramidite | 10-1928 |
| 5'-I-dT-CE phosphoramidite | 10-1931 |
| 5'-Amino-dT-CE phosphoramidite | 10-1932 |
| 5'-Aldehyde-Modifier C2 phosphoramidite | 10-1933 |
| 5'-Formylindole-CE phosphoramidite | 10-1934 |
| 5'-Carboxy-Modifier C10 | 10-1935 |
| Thiol-Modifier C6 S-S | 10-1936 |
| Thiol-Modifier C6 S-S | 10-1936 |
| 5'-Maleimide-Modifier phosphoramidite | 10-1938 |
| Spermine phosphoramidite | 10-1939 |
| 5'-DBCO-TEG phosphoramidite | 10-1941 |
| 5'-Carboxy-Modifier C5 | 10-1945 |
| 5'-Bromohexyl phosphoramidite | 10-1946 |
| F-Amino-Modifier C6-PDA | 10-1947 |
| F-Amino-Modifier C12-PDA | 10-1948 |
| F-Amino-Modifier TEG PDA | 10-1949 |
| DesthiobiotinTEG phosphoramidite | 10-1952 |

TABLE 4-continued

| Amidite Reagent | Catalog No. |
| --- | --- |
| Biotin phosphoramidite | 10-1953 |
| BiotinTEG phosphoramidite | 10-1955 |
| Fluorescein phosphoramidite | 10-1963 |
| 6-Fluorescein phosphoramidite | 10-1964 |
| Acridine phosphoramidite | 10-1973 |
| Cholesteryl-TEG phosphoramidite | 10-1975 |
| 5'-Cholesteryl-TEG phosphoramidite | 10-1976 |
| α-Tocopherol-TEG phosphoramidite | 10-1977 |
| Stearyl phosphoramidite | 10-1979 |
| Psoralen C2 phosphoramidite | 10-1982 |
| Psoralen C6 phosphoramidite | 10-1983 |
| DNP-TEG phosphoramidite | 10-1985 |
| 5'-Trimethoxystilbene Cap phosphoramidite | 10-1986 |
| 5'-Pyrene Cap phosphoramidite | 10-1987 |
| Dithiol Serinol phosphoramidite | 10-1991 |
| Alkyne-Modifier Serinol phosphoramidite | 10-1992 |
| Protected Biotin Serinol phosphoramidite | 10-1993 |
| 6-Fluorescein Serinol phosphoramidite | 10-1994 |
| Protected BiotinLC Serinol phosphoramidite | 10-1995 |
| Amino-Modifier Serinol phosphoramidite | 10-1997 |
| Pac-A-CE phosphoramidite | 10-3000 |
| Bz-A-CE phosphoramidite | 10-3003 |
| A-TOM-CE phosphoramidite | 10-3004 |
| N6-Methyl-A-CE phosphoramidite | 10-3005 |
| Zebularine-CE phosphoramidite | 10-3011 |
| Pyridin-2-one-CE phosphoramidite | 10-3012 |
| C-TOM-CE phosphoramidite | 10-3014 |
| Ac-C-CE phosphoramidite | 10-3015 |
| Pyrrolo-C-TOM-CE phosphoramidite | 10-3017 |
| iPr-Pac-G-CE phosphoramidite | 10-3021 |
| G-TOM-CE phosphoramidite | 10-3024 |
| Ac-G-CE phosphoramidite | 10-3025 |
| U-CE phosphoramidite | 10-3030 |
| U-TOM-CE phosphoramidite | 10-3034 |
| Amino-Modifier C6-U phosphoramidite | 10-3039 |
| I-CE phosphoramidite | 10-3040 |
| 5-Me-U-CE phosphoramidite | 10-3050 |
| 4-Thio-U-TOM-CE phosphoramidite | 10-3052 |
| PseudoUridine-CE phosphoramidite | 10-3055 |
| 5-Me-C-TOM-CE phosphoramidite | 10-3064 |
| 2-Aminopurine-TBDMS-CE phosphoramidite | 10-3070 |
| 6-Thio-G-CE phosphoramidite | 10-3072 |
| 8-Aza-7-deaza-A-CE phosphoramidite | 10-3083 |
| 2,6-Diaminopurine-TOM-CE phosphoramidite | 10-3085 |
| Br-U-CE phosphoramidite | 10-3090 |
| 5-I-U-CE phosphoramidite | 10-3091 |
| 2'-OMe-A-CE phosphoramidite | 10-3100 |
| 2'-OMe-C-CE phosphoramidite | 10-3110 |
| 2'-OMe-TMP-5-F-U-CE phosphoramidite | 10-3111 |
| 2'-OMe-Ac-C-CE phosphoramidite | 10-3115 |
| 2'-OMe-3-deaza-5-aza-C-CE phosphoramidite | 10-3116 |
| 2'-OMe-ibu-G-CE phosphoramidite | 10-3120 |
| 2'-OMe-G-CE phosphoramidite | 10-3121 |
| 2'-OMe-2-Aminopurine-CE phosphoramidite | 10-3123 |
| 2'-OMe-2,6-Diaminopurine-CE phosphoramidite | 10-3124 |
| 2'-OMe-U-CE phosphoramidite | 10-3130 |
| 2'-OMe-5-Me-U-CE phosphoramidite | 10-3131 |
| 2'-OMe-5-F-U-CE phosphoramidite | 10-3132 |
| 2'-OMe-I-CE phosphoramidite | 10-3140 |
| 2'-OMe-5-Me-C-CE phosphoramidite | 10-3160 |
| 2'-OMe-5-Br-U-CE phosphoramidite | 10-3190 |
| 2'-F-A-CE phosphoramidite | 10-3400 |
| 2'-F-Ac-C-CE phosphoramidite | 10-3415 |
| 2'-F-G-CE phosphoramidite | 10-3420 |
| 2'-F-U-CE phosphoramidite | 10-3430 |
| 1-Me-A-CE phosphoramidite | 10-3501 |
| 2'-OMe-Pac-A-CE phosphoramidite | 10-3601 |
| 2'-OMe-iPr-Pac-G-CE phosphoramidite | 10-3621 |
| 2'-F-A-ANA-CE phosphoramidite | 10-3800 |
| 2'-F-C-ANA-CE phosphoramidite | 10-3810 |
| 2'-F-Ac-C-ANA-CE phosphoramidite | 10-3815 |
| 2'-F-G-ANA-CE phosphoramidite | 10-3820 |
| 2'-F-U-ANA-CE phosphoramidite | 10-3830 |
| rSpacer CE phosphoramidite | 10-3914 |
| PC Amino-Modifier phosphoramidite | 10-4906 |
| PC Spacer phosphoramidite | 10-4913 |
| PC Linker phosphoramidite | 10-4920 |
| PC Biotin phosphoramidite | 10-4950 |

TABLE 4-continued

| Amidite Reagent | Catalog No. |
| --- | --- |
| Azobenzene phosphoramidite | 10-5800 |
| 2,2'-Dipicolylamine phosphoramidite | 10-5801 |
| 5'-Fluorescein phosphoramidite | 10-5901 |
| 5'-Hexachloro-Fluorescein phosphoramidite | 10-5902 |
| 5'-Tetrachloro-Fluorescein phosphoramidite | 10-5903 |
| SIMA (HEX) phosphoramidite | 10-5905 |
| 5'-Dichloro-dimethoxy-Fluorescein phosphoramidite II | 10-5906 |
| 5'-Dabcyl phosphoramidite | 10-5912 |
| Cyanine 3 phosphoramidite | 10-5913 |
| Cyanine 3.5 phosphoramidite | 10-5914 |
| Cyanine 5 phosphoramidite | 10-5915 |
| Cyanine 5.5 phosphoramidite | 10-5916 |
| DyLight DY547 phosphoramidite | 10-5917 |
| DyLight DY647 phosphoramidite | 10-5918 |
| Epoch Redmond Red ™ phosphoramidite | 10-5920 |
| EpochYakima Yellow ™ phosphoramidite | 10-5921 |
| Epoch Gig Harbor Green ™ phosphoramidite | 10-5922 |
| Epoch Eclipse ™ Quencher phosphoramidite | 10-5925 |
| 5'-BHQ-1 phosphoramidite | 10-5931 |
| 5'-BHQ-2 phosphoramidite | 10-5932 |
| 5'-BBQ-650 ®-CE phosphoramidite | 10-5934 |
| BHQ-1-dT | 10-5941 |
| BHQ-2-dT | 10-5942 |
| BBQ-650 ®-dT-CE phosphoramidite | 10-5944 |
| SIMA (HEX)-dT phosphoramidite | 10-5945 |
| 5'-Biotin phosphoramidite | 10-5950 |
| Methylene Blue 03 phosphoramidite | 10-5960 |
| dmf-dG-5'-CE phosphoramidite | 10-9201 |
| Cis-syn Thymine Dimer phosphoramidite | 11-1330 |
| Commercially available from: Chemgenes Corporation, 33 Industrial Way, Wilmington, MA, USA | |
| DMT-butane-Diol phosphoramidite | CLP-9775 |
| DMT-dodecane-Diol phosphoramidite | CLP-1114 |
| DMT-ethane-Diol phosphoramidite | CLP-2250 |
| DMT-hexaethyloxy-Glycol phosphoramidite | CLP-9765 |
| DMT-hexane-Diol phosphoramidite | CLP-1120 |
| DMT-nonane-Diol phosphoramidite | CLP-9009 |
| DMT-propane-Diol phosphoramidite | CLP-9908 |
| DMT-tetraethyloxy-Glycol CED phosphoramidite | CLP-1368 |
| DMT-triethyloxy-Glycol phosphoramidite | CLP-1113 |
| Polyethyleneglycol 2000 CED phosphoramidite | CLP-2119 |
| Polyethyleneglycol 4500 CED phosphoramidite | CLP-3118 |
| L-dA (n-bz) CE phosphoramidite | ANP-8031 |
| L-dC (n-acetyl) CE phosphoramidite | ANP-8035 |
| L-dC (n-bz) CE phosphoramidite | ANP-8032 |
| L-dG (n-ibu) CE phosphoramidite | ANP-8033 |
| L-dT CE phosphoramidite | ANP-8034 |

The amidite reagents listed above in Table 4 can be used to prepare a tag having a polymeric structure via standard amidite coupling chemistry. That is, each of the phosphoramidite (or phosphonamidite) reagents will react in an amidite coupling reaction with a nucleotide polymer (e.g., oligonucleotide) to insert a monomer unit with its particular structure into the polymer. This resulting polymeric structure will have phosphate (or phosphonate) linkage to the adjacent monomer units in the polymer. Thus, Table 4 effectively provides a list of over 300 monomer units that can be used to prepare distinct tags. See e.g., U.S. Provisional Patent Appl. No. 62/235,551, filed Sep. 30, 2015, which is hereby incorporated by reference herein. Such tags can then be used to produce a tagged multi-nucleotide of the present disclosure via linking chemistry disclosed herein, and well-known to the skilled artisan. Accordingly, the present disclosure provides a tagged multi-nucleotide compound (e.g., having structural formula (I), (II), or (III)), wherein the tag comprised a polymeric structure having at least one monomer unit resulting from the reaction of an amidite reagent selected from Table 4.

Generally, in any of the embodiments of tagged multi-nucleotide compounds disclosed herein, the Tag can comprise an oligonucleotide of at least 10-mer, 15-mer, 20-mer, 25-mer, 30-mer, 35-mer, 40-mer, or more monomer units in length; optionally, wherein the oligonucleotide comprises monomer units selected from a nucleotide, a nucleotide analog, a spacer units, any non-natural monomer unit formed via a phosphoramidite reaction, and any combination thereof. Exemplary tagged multi-nucleotide compounds, wherein the tag comprises an oligonucleotide include the compounds disclosed in the Examples, including compound (3a) and compound (3b).

The ordinary artisan will recognize that some of the monomer units disclosed in Table 4 are also referred to in commercial oligonucleotide synthesis catalogs as "spacers" (e.g., "iSp"), "dyes" (e.g., "iCy3"), or "linkers" (e.g., "hexynyl"). The ordinary artisan will also recognize that some of the oligonucleotide tags described herein (e.g., Table 3 and the Examples) are referred to using well-known oligonucleotide synthesis nomenclature (see e.g., the web-site of Integrated DNA Technologies at www.idtdna.com for further description of commonly used oligonucleotide synthesis nomenclature).

The present disclosure provides the ordinary artisan with tools to prepare tagged multi-nucleotides with tags that provide detection characteristics useful across a wide range of assay schemes, and in particular, use with nanopore detection systems.

Polypeptide Tags

In some embodiments, the tagged multi-nucleotides of the present disclosure can comprise a tag comprising a polymer of amino acids—i.e., a polypeptide. The use of polypeptide as tags for tagged nucleotides useful in nanopore sequencing is described in U.S. provisional patent application 62/216,634, filed Sep. 10, 2015, which is hereby incorporated by reference herein. The polypeptide tags disclosed in U.S. Ser. No. 62/216,634 generally are polymeric chains of 30 or more amino acids that have an overall charge and at least one helical structure. The helical structures of the polypeptide tags is described as providing stronger blocking currents that show less variance when the tag structure enters and resides in a nanopore. It is proposed that polypeptide tags having helical structures, such as α-helix loops, of 16 amino acids or longer (e.g., from 16 to 80 amino acids), can fit in the pore of a nanopore better so as to provide stronger current blocking currents and longer dwell times than polypeptides having linear or random coil structures. U.S. Ser. No. 62/216,634 discloses a range polypeptide tags with amino acid sequences that have a range of lengths, helical structures, and overall charges.

Based on the utility of single nucleotides with single polypeptide tags in nanopore sequencing embodiments as disclosed in U.S. Ser. No. 62/216,634, it is contemplated that in any of the embodiments of tagged multi-nucleotide compounds disclosed herein, the tag can comprise a polypeptide. In some embodiments of the tagged multi-nucleotides, wherein the tag is a polypeptide, the polypeptide has a length is at least 10 amino acids, at least 16 amino acids, at least 20 amino acids, at least 25 amino acids, at least 30 amino acids, at least 40 amino acids, at least 50 amino acids, at least 60 amino acids, at least 70 amino acids, at least 80 amino acids, or even more amino acids. In some embodiments, the length of the polypeptide is from 10 to 100 amino acids, from 16 to 90 amino acids, from 30 to 90 amino acids, from 40 to 80 amino acids, or from 50 to 70 amino acids.

In some embodiments of the present disclosure, the polypeptide tag of the tagged multi-nucleotides comprises a helical structure. The polypeptide helical structure may comprise all of the amino acid residues of the polypeptide or some sub-portion(s) of the polypeptide. Accordingly, in some embodiments of the polypeptide tags of a tagged multi-nucleotide, the polypeptide helical structure comprises is at least 10 amino acids, at least 16 amino acids, at least 20 amino acids, at least 25 amino acids, at least 30 amino acids, at least 40 amino acids, at least 50 amino acids, or at least 60 amino acids.

In some embodiments of the present disclosure, the polypeptide tag of the tagged multi-nucleotides comprises a helical structure that comprises an α-helix. In some embodiments, the α-helix comprises at least two repeats of a sequence motif comprising at least three amino acids. Optionally, the sequence motif comprising at least three amino acids is a homopolymer, and further optionally, the homopolymeric sequence motif comprising at least three amino acids comprises the sequence AAA.

The capture and detection of a tagged nucleotide by a nanopore can be facilitated by the charge of the tag molecule. Generally, when a nanopore detection system is set-up under an alternating current (AC) or direct current (DC) potential with the cis side of the pore (i.e., reservoir side with nucleotides and polymerase) having a negatively-charged electrode and the trans side having a positively-charged electrode, it is preferred that the tag of the tagged nucleotide has a negative charge. Under such conditions, the capture and detection of the negatively-charged tag can be facilitated by the electromotive force provided by the trans side positive electrode. Alternatively, a positively-charged tag generally would be preferred under conditions wherein the trans side of the nanopore system comprises a negative electrode.

The present disclosure provides tagged multi-nucleotides comprising a polypeptide tag, wherein the polypeptide has 30 or more amino acids and an overall charge. The overall charge is that net charge of the whole polypeptide based on summing the charge of each of the amino acid side chains that make up the polypeptide. Because a large variety of charged amino acid residues are available that can be incorporated into a polypeptide sequence, the overall charge of a polypeptide tag of the present disclosure can be easily adjusted (or tuned) over a wide range to allow for a wide range of possible nanopore detection characteristics.

In some embodiments, the present disclosure provides tagged multi-nucleotides, wherein the overall charge of the polypeptide is negative. In some embodiments, the overall charge of the polypeptide is between about −10 and −30. In the embodiments where the overall charge of the polypeptide is negative, the polypeptide sequence can comprise one or more negatively charged amino acid residues, wherein the negatively charged residues can be the same or different. For example, in the case of polypeptide tag having an overall charge of −10, the polypeptide sequence would need to comprise at least 10 negatively charged residues. In some embodiments, the negatively charged residues are selected from the group consisting of: glutamic acid, aspartic acid, gamma-carboxy glutamic acid, homo-glutamic acid, cysteic acid, phospho-serine, phospho-threonine, phospho-tyrosine, and combinations thereof.

Alternatively, in some embodiments of the tagged multi-nucleotides wherein the tag comprises a polypeptide, the overall charge of the polypeptide is positive, and optionally has an overall charge of between about +10 and +30. In such embodiments, the polypeptide sequence can comprise one or more positively charged amino acid residues, optionally selected from the group consisting of: arginine, lysine, and histidine. It is contemplated that in some embodiments the overall charge of the polypeptide can be distributed equally over the length of the tag. In some embodiments, however, the overall charge of the polypeptide tag can be distributed unequally over the length of the polypeptide sequence. Such unequal charge distribution can provide the tag with further distinguishing characteristics under nanopore detection conditions, e.g., either AC or DC potential. Accordingly, in some embodiments the present disclosure provides a tagged multi-nucleotide, wherein the tag comprises a polypeptide and wherein the 25% of the amino acid residues located at the end of the polypeptide tag distal (i.e., further) from the linker have a net charge absolute value greater than the net charge absolute value of the 25% of the amino acid residues located at the end of the polypeptide proximal (i.e., nearer) to the linker. That is, if overall charge is negative, the 25% of the amino acid residues distal from the linker would be more negatively charged than the 25% of the amino acid residues proximal to the linker.

Utilizing the knowledge in the art regarding amino acid residues, the charge, length, volume, and mass characteristics, and their known propensities to form certain types of structures when polymerized in polypeptide sequences (e.g., α-helix-forming propensity), and following the present disclosure regarding tagged multi-nucleotides compounds and their use, it is possible to design a variety of tags comprising polypeptides that can provide a range of detectable signals, particular nanopore detectable signals. Table 5 shows exemplary polypeptide tags that can be used in the tagged multi-nucleotides of the present disclosure.

TABLE 5

| Tag | # amino acids | Overall charge | SEQ ID NO: |
|---|---|---|---|
| (EAAA)$_{16}$-E$_5$ | 69 | −21 | 110 |
| (EAAA)$_{13}$-E$_5$ | 57 | −18 | 111 |
| (EAAA)$_{10}$-E$_5$ | 45 | −15 | 112 |
| (EAAA)$_{15}$-Gla$_4$-E | 69 | −25 | 113 |
| Biotin-(UE)$_{25}$ | 51 | −25 | 114 |
| (EAAA)$_8$-P-(EAAA)$_8$-E$_5$ | 70 | −21 | 115 |
| (EAAA)$_4$-P-(EAAA)$_4$-P-(EAAA)$_4$-P-(EAAA)$_4$-E$_5$ | 70 | −21 | 116 |
| (EAAAKAAA)$_4$-(EAAA)$_8$-E$_5$ | 69 | −13 | 117 |
| (EAAAKAAA)$_8$-E$_5$ | 69 | −5 | 118 |
| (E-P$_9$)$_5$-E$_5$ | 55 | −10 | 119 |
| (E-P$_3$)$_{16}$-E$_5$ | 69 | −21 | 120 |
| P$_{45}$-E$_5$ | 50 | −5 | 121 |
| (RAAA)$_{16}$-R$_5$ | 69 | +21 | 122 |
| (EATA)$_{16}$-E$_5$ | 69 | −21 | 123 |

Abbreviations
"U" = beta-aianine
"Gia" = gamma-carboxy giutarnic acid

The exemplary polypeptide tags shown in Table 5 comprise natural and/or unnatural amino acid monomers and can be prepared by standard solid-phase polypeptide synthesis methods. Additionally, these polypeptide tags (and virtually any other polypeptide sequence of up to 80 amino acids) are commercially available from custom peptide vendors such Peptide 2.0 (Chantilly, Va., USA) or GenScript (Piscataway, N.J., USA).

Methods of Preparing Tagged Multi-Nucleotide Compounds

Standard synthetic methods can be used in preparing the tagged multi-nucleotide compounds of the present disclosure (e.g., compounds of structural formulas (I), (II), (III)). The standard azido-alkyne click reaction is described above (e.g., compounds of (XIX), (XX), (XXI), or (XXII)) and in the Examples. Tables 1 and 2 illustrate a range of linkers and linker forming group reactions that can be used in preparing the tagged multi-nucleotides of the present disclosure. In one embodiment, any of the linker forming groups of structural formulas (IVa)-(XVIIa) shown in Table 1 can be attached to a branched or dendrimeric linker attached to a tag, or to a terminal phosphate of a nucleotide, and the corresponding conjugate linker forming group of structural formulae (IVb)-(XVIIb) would be attached to other. The resulting covalent linker structures forming the multi-nucleotide-oligophosphate-linker-tag compound are exemplified by structural formulae (IVc)-(XVIIc) in Table 1. The covalent linkage structure and include the dihydropyrazidine group structure (XVIIc) that results from the click reaction of trans-cyclooctene (XVIIa) and tetrazine (XVIIb) linker forming groups.

Accordingly, the present disclosure provides a method of preparing a tagged multi-nucleotide comprising: (a) providing (i) a nucleotide with from 3 to 12 phosphates attached to its 5'-position, wherein the terminal phosphate is coupled to a first linker forming group (e.g., $X_A$ or $X_B$); and (ii) a tag, wherein the tag is coupled to a branched or dendrimeric linker comprising at least two second linker forming group (e.g., $X_B$ or $X_A$) that is capable of reacting with the first linker forming group to form a linker (e.g., —X—); and (b) reacting the first linker forming group with the two second linker forming groups on the branched or dendrimeric linker to link at least two nucleotides to the single tag. First and second linker forming groups that are capable of reacting to form a linker are exemplified in Table 1 above. Thus, in some embodiments of the method, the first linker forming group is selected from the compounds of structural formulas (IVa)-(XVIIa) and the second linker forming group is the corresponding reactive compound of structural formulas (IVb)-(XVIIb); or alternatively, the first linker forming group can selected from the compounds of structural formulas (IVb)-(XVIIb) and the second linker forming group is the corresponding reactive compound of structural formulas (IVa)-(XVIIa). Branched or dendrimeric linker structure can be generated using the doubler or trebler linker units of compounds (19) or (20). In some embodiments, the doubler or trebler linker units can be linked in a serial fashion to generate branched or dendrimeric linkers have four or more reactive linker forming groups available (e.g., as in compound (21)).

In some embodiments, the disclosure provides method of preparing a tagged multi-nucleotide compound of structural formula (II)

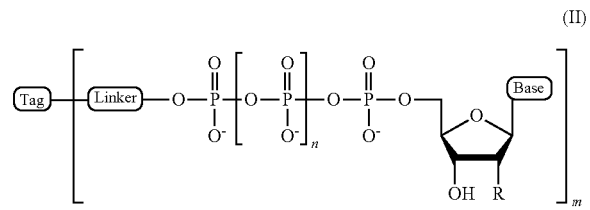

(II)

wherein, Base is selected from adenosine, cytidine, guanosine, thymidine, and uridine; R is selected from H and OH; n is from 1 to 4; Linker is a linker comprising a covalently bonded chain of 2 to 100 atoms; m is from 2 to 12; and Tag is a molecular moiety which is capable of producing a detectable signal; and the method comprises the steps of:
(a) providing (i) a nucleotide with from 3 to 12 phosphates attached to its 5'-position, wherein the terminal phosphate is coupled to a first linker forming group; and (ii) a tag, wherein the tag comprises a molecular moiety which is capable of producing a detectable signal, and is coupled to branched or dendrimeric linker comprising at least two second linker forming groups that are each capable of reacting with a first linker forming group to form a covalent linker between at least two nucleotides and a single tag;
wherein
(1) the first linker forming group is selected from the compounds of structural formulas (IVa)-(XVIIa) and the second linker forming group is the corresponding reactive compound of structural formulas (IVb)-(XVIIb); or
(2) the first linker forming group is selected from the compounds of structural formulas (IVb)-(XVIIb) and the second linker forming group is the corresponding reactive compound of structural formulas (IVa)-(XVIIa);
and
(b) reacting the first linker forming group with the second linker forming group, thereby forming a covalent linkage between at least two nucleotides and a single tag.

In some embodiments of the methods of preparing the tagged multi-nucleotide compound, the first linker forming group attached to the terminal phosphate is an azide group and the second linker forming group attached a branched or dendrimeric linker attached to a tag is an alkyne. In other embodiments, the first linker forming group attached to the terminal phosphate is an alkyne group and the second linker forming group attached a branched or dendrimeric linker attached to a tag is an azide.

In some embodiments of the methods of preparing the tagged multi-nucleotide, the first linker forming group attached to the terminal phosphate is a tetrazine and the second linker forming group attached a branched or dendrimeric linker attached to a tag is a trans-cyclooctene. In other embodiments, the first linker forming group attached to the terminal phosphate is a trans-cyclooctene and the second linker forming group attached the tag is a tetrazine.

Use of Tagged Multi-Nucleotides in Nanopore Sequencing

The tagged multi-nucleotide compounds of the present disclosure can be used in the known nanopore sequencing methods wherein a nanopore detects the presence of a tag attached to a complementary nucleotide as it is incorporated (or after it is incorporated and released) by a strand-extending enzyme (e.g., polymerase, ligase) located proximal to the nanopore and which is extending a primer complementary of a target nucleic acid sequence. General methods, materials, devices, and systems for carrying out nanopore sequencing using tagged nucleotides are described in US Pat. Publ. Nos. 2013/0244340 A1, 2013/0264207 A1, 2014/0134616 A1, 2015/0119259 A1, and U.S. Ser. No. 14/666,124, filed Mar. 23, 2015, each of which is hereby incorporated by reference herein. The tagged multi-nucleotides of the present disclosure can be employed in these general methods for using tagged-nucleotides for nanopore sequencing of nucleic acids. Indeed, as illustrated in the Examples herein, the tagged multi-nucleotide compounds of the present disclosure have improved characteristics as polymerase substrates that provide for faster, longer, and more accurate sequence reads in nanopore sequencing than the corresponding single-nucleotide-single-tag compounds.

Thus, in one embodiment, the present disclosure provides a method for determining the sequence of a nucleic acid comprising: (a) providing a nanopore sequencing composition comprising: a membrane, an electrode on the cis side and the trans side of the membrane, a nanopore with its pore extending through the membrane, an electrolyte solution in contact with both electrodes, an active polymerase situated adjacent to the nanopore, and a primer strand complexed with the polymerase; (b) contacting the nanopore sequencing composition with (i) a strand of the nucleic acid; and (ii) a set of tagged multi-nucleotides each with a different tag, wherein each different tag causes a different blocking current level across the electrodes when it is situated in the nanopore, and the set comprises at least one compound of structural formula (I)

wherein, N is a nucleoside; P is an oligophosphate covalently attached to a 5'-O group of the nucleoside, wherein the oligophosphate consists of 3 to 12 phosphate groups; L is a linker covalently attached to a terminal phosphate group of the oligophosphate; m is from 2 to 12 and indicates the number of N-P-L moieties; and T is a tag covalently attached the N-P-L moieties, wherein the tag is a molecular moiety capable of producing a detectable signal; and (d) detecting current levels across the electrodes over time and correlating to each of the different tagged multi-nucleotides incorporated by the polymerase which are complimentary to the nucleic acid sequence, and thereby determining the nucleic acid sequence.

In some embodiments of the method for determining the sequence of a nucleic acid, the set of tagged multi-nucleotides each with a different tag, comprises at least one compound that comprises a structure of formula (II):

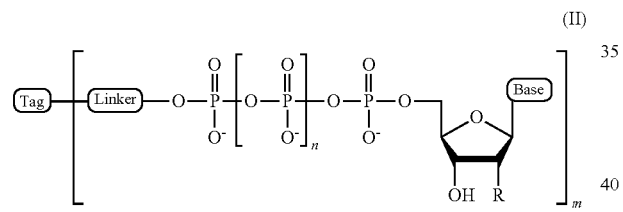

wherein, Base is selected from adenosine, cytidine, guanosine, thymidine, and uridine; R is selected from H and OH; n is from 1 to 4; Linker is a linker comprising a covalently bonded chain of 2 to 100 atoms; m is from 2 to 12; and Tag is a molecular moiety which is capable of producing a detectable signal.

When used in the methods for determining the sequence of a nucleic acid the tagged multi-nucleotide compounds comprising structures of formula (I) or (II) can include any of the ranges of compound embodiments disclosed elsewhere herein. For example, the nucleoside (N) of formula (I) can be any nucleoside capable of being incorporated by a strand-extending enzyme, such as a polymerase, when the nucleoside is covalently coupled to an oligophosphate (P), such as a triphosphate; and the nucleoside can comprise a naturally occurring or non-naturally occurring nucleobase, and a naturally occurring or non-naturally occurring sugar moiety, such as a ribose or deoxyribose group.

Sets of Tagged Multi-Nucleotides

As described elsewhere herein, methods for determining the sequence of a nucleic acid using nanopore detection generally require a set of tagged nucleotide compounds each capable of being a substrate for a strand-extending enzyme and each comprising a different tag associated with a nucleotide that is desired to be detected. In standard embodiments for sequencing DNA strands, the method requires a set of at least the four standard deoxy-nucleotides dA, dC, dG, and dT, wherein each different nucleotide is attached to a different single tag capable of being detected upon the nucleotide being incorporated by a proximal strand extending enzyme, and furthermore wherein the detection of the tag is distinguishable from the nanopore detection of each of the other three tags, thereby allowing identification of the specific nucleotide incorporated by the enzyme. Generally, each of the different tagged nucleotides in a set is distinguished by the distinctive detectable signal the tag produces when it is incorporated into a new complementary strand by a strand-extending enzyme.

Among the detectable signal characteristics, alone or in combination, that can be used to distinguish the tagged multi-nucleotides in a nanopore detection method are the blocking current level across the electrodes of the nanopore detection system (under either DC or AC potential), and the dwell time of the blocking current. Accordingly, in some embodiments, the present disclosure provides a set of tagged multi-nucleotides each with a different tag, wherein each different tag causes a different blocking current level across the electrodes and/or a different dwell time when it is situated in the nanopore, and the set comprises at least one compound of structural formula (I)

wherein, N is a nucleoside; P is an oligophosphate covalently attached to a 5'-O group of the nucleoside, wherein the oligophosphate consists of 3 to 12 phosphate groups; L is a linker covalently attached to a terminal phosphate group of the oligophosphate; m is from 2 to 12 and indicates the number of N-P-L moieties; and T is a tag covalently attached the N-P-L moieties, wherein the tag is a molecular moiety capable of producing a detectable signal.

In some embodiments of the set of tagged multi-nucleotides each with a different tag, the set comprises at least one compound that comprises a structure of formula (II):

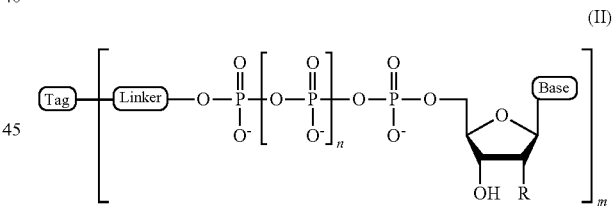

wherein, Base is selected from adenosine, cytidine, guanosine, thymidine, and uridine; R is selected from H and OH; n is from 1 to 4; Linker is a linker comprising a covalently bonded chain of 2 to 100 atoms; m is from 2 to 12; and Tag is a molecular moiety which is capable of producing a detectable signal.

It is contemplated that the tagged multi-nucleotides of the present disclosure may be used in sets of tagged nucleotides that also include tagged single nucleotides, and/or sets with tagged nucleotides having different types of tags, such as both oligonucleotide tags and polypeptide tags. For example, in some embodiments, the set of tagged multi-nucleotides can comprise a tagged multi-nucleotide of structural formula (I) or (II) and the other tagged nucleotides in the set can comprise single nucleotides attached to single tags. Alternatively, the set of tagged multi-nucleotides can include a range of tag structures, such as an oligonucleotide tag, a polypeptide tag, a polyethylene glycol tag, a carbohydrate tag, and/or a dye compound tag. Sets of oligonucleotide-tagged nucleotides useful for nanopore sequencing are known in the art and these tags can be used in the tagged multi-nucleotide embodiments disclosed herein. (See e.g., US Pat. Publ. Nos. 2013/0244340 A1, 2013/0264207 A1, 2014/0134616 A1, 2015/0119259 A1, and U.S. Ser. No. 14/666,124, filed Mar. 23, 2015, each of which is hereby incorporated by reference herein.)

In some embodiments, the set of tagged multi-nucleotides comprises at least two, at least three, or at least four tagged multi-nucleotide compounds of structural formula (I) or structural formula (II), wherein each of the different tags of the at least two, at least three, or at least four of the tagged multi-nucleotide compounds in the set produces a nanopore detectable signal that is distinguishable from the others in the set. Methods and techniques for determining the nanopore detectable signal characteristics, such as blocking current and/or dwell time, are known in the art. (See e.g., US Pat. Publ. Nos. 2013/0244340 A1, 2013/0264207 A1, 2014/0134616 A1, 2015/0119259 A1, and U.S. Ser. No. 14/666, 124, filed Mar. 23, 2015, each of which is hereby incorporated by reference herein.) Such methods include nanopore sequencing experiments under AC voltage potentials using a nanopore array as described in the Examples herein.

Accordingly, in some embodiments, the present disclosure provides a set of tagged multi-nucleotides comprising at least two different tagged multi-nucleotides each having a different tag, wherein the at least two different tags exhibit distinguishable blocking current levels and/or dwell times. In some embodiments of the set of tagged multi-nucleotides, the at least two different tagged multi-nucleotides comprise a compound of structure (I) or structure (II). In some embodiments, the at least two different tagged multi-nucleotides each comprise a different oligonucleotide tag structure selected from Table 3, 7, 8, or 10, and/or an oligonucleotide sequence selected from SEQ ID NO: 1-109. In some embodiments, the at least two different tags exhibit blocking current levels that differ by at least 10%, at least 25%, at least 50%, or at least 75%. The measurement of the difference between blocking current levels can be made using any suitable nanopore detection method. For example, the blocking currents of each of the at least two different tagged multi-nucleotides each having a different oligonucleotide tag can be measured in a nanopore sequencing experiment, as is generally described in the Examples herein.

Nanopore Devices

Nanopore devices and methods for making and using them in nanopore detection applications such as nanopore sequencing using tagged nucleotides are known in the art (See e.g., U.S. Pat. Nos. 7,005,264 B2; 7,846,738; 6,617, 113; 6,746,594; 6,673,615; 6,627,067; 6,464,842; 6,362, 002; 6,267,872; 6,015,714; 5,795,782; and U.S. Publication Nos. 2015/0119259, 2014/0134616, 2013/0264207, 2013/0244340, 2004/0121525, and 2003/0104428, each of which are hereby incorporated by reference in their entirety). Nanopore devices useful for measuring nanopore detection are also described in the Examples disclosed herein. Generally, the nanopore devices all comprise pore-forming protein embedded in a lipid-bilayer membrane, wherein the membrane is immobilized or attached to a solid substrate which comprises a well or reservoir. The pore of the nanopore extends through the membrane creating a fluidic connection between the cis and trans sides of the membrane. Typically, the solid substrate comprises a material selected from the group consisting of polymer, glass, silicon, and a combination thereof. Additionally, the solid substrate comprises adjacent to the nanopore, a sensor, a sensing circuit, or an electrode coupled to a sensing circuit, optionally, a complementary metal-oxide semiconductor (CMOS), or field effect transistor (FET) circuit. Typically, there are electrodes on the cis and trans sides of the membrane that allow for a DC or AC voltage potential to be set across the membrane which generates a baseline current flow (or Open Current level) through the pore of the nanopore. The presence of a tag, such as a tag of a tagged multi-nucleotide of the present disclosure results in blocking this current flow and thereby generating a blocking current level relative to the open current that can be measured.

It is contemplated that the tagged multi-nucleotide compounds of the present disclosure can be used with a wide range nanopore devices comprising nanopores generated by both naturally-occurring, and non-naturally occurring (e.g., engineered or recombinant) pore-forming proteins. A wide range of pore-forming proteins are known in the art that can be used to generate nanopores useful for nanopore detection of the tagged multi-nucleotides of the present disclosure. Representative pore forming proteins include, but are not limited to, α-hemolysin, β-hemolysin, γ-hemolysin, aerolysin, cytolysin, leukocidin, melittin, MspA porin and porin A. The pore-forming protein, α-hemolysin from *Staphylococcus aureus* (also referred to herein as "α-HL"), is one of the most-studied members of the class of pore-forming proteins, and has been used extensively in creating nanopore devices. (See e.g., U.S. Publication Nos. 2015/0119259, 2014/0134616, 2013/0264207, and 2013/0244340.) α-HL also has been sequenced, cloned, extensively characterized structurally and functionally using a wide range of techniques including site-directed mutagenesis and chemical labelling (see e.g., Valeva et al. (2001), and references cited therein). A heptameric complex of α-HL monomers spontaneously forms a nanopore that embeds in and creates a pore through a lipid bilayer membrane. It has been shown that heptamers of α-HL comprising a ratio of 6:1 native α-HL to mutant α-HL can form nanopores (see e.g., Valeva et al. (2001), and references cited therein). Further, α-HL has been engineered with cysteine residue substitutions inserted at numerous positions allowing for covalent modification of the protein through maleimide linker chemistry (Ibid.) For example, the engineered α-hemolysin-C46 ("α-HL-C46"), comprises a K46C amino acid residue substitution that allows for modification with a linker that can be used to covalently attach a strand-extending enzyme, such as polymerase, using common click reaction chemistry. Alternatively, the α-HL heptamer can be modified covalently with a DNA-polymerase using a SpyCatcher/SpyTag conjugation method.

Accordingly, in some embodiments, the tagged multi-nucleotide compositions of the present disclosure can be used with a nanopore device, wherein the nanopore comprises a heptameric α-HL complex, which has 6:1 native α-HL to a modified, or engineered version of α-HL, wherein the modified α-HL is conjugated covalently to a strand-extending enzyme, such as DNA polymerase. For example, the engineered α-HL-C46 can be modified with a linker allowing the use of tetrazine-trans-cyclooctene click chemistry to covalently attach a Bst2.0 variant of DNA polymerase to the heptameric 6:1 nanopore. Such an embodiments is described in U.S. Provisional Application No. 62/130,326, filed Mar. 9, 2015, which is hereby incorporated by reference herein.

The tagged multi-nucleotides and associated methods provided herein can be used with a wide range of strand-extending enzymes such as the polymerases and ligases known in the art.

DNA polymerases are a family of enzymes that use single-stranded DNA as a template to synthesize the complementary DNA strand. DNA polymerases add free nucleotides to the 3' end of a newly-forming strand resulting in extension of the new strand in the 5'-to-3' direction. Most DNA polymerases also possess exonucleolytic activity. For example, many DNA polymerases have 3'-5' exonuclease activity. Such multifunctional DNA polymerases can recognize an incorrectly incorporated nucleotide and use the 3'→5' exonuclease activity to excise the incorrect nucleotide, an activity known as proofreading. Following nucleotide excision, the polymerase can re-insert the correct nucleotide and strand extension can continue. Some DNA polymerases also have 5'→3' exonuclease activity.

DNA polymerases are used in many DNA sequencing technologies, including nanopore-based sequencing-by-synthesis. However, a DNA strand can move rapidly through the nanopore (e.g., at a rate of 1 to 5 μs per base), which can make nanopore detecting of each polymerase-catalyzed incorporation event difficult to measure and prone to high background noise, which can result in difficulties in obtaining single-nucleotide resolution. The ability to control the rate of DNA polymerase activity, as well as, increase the detectable signal from correct incorporation is important during sequencing-by-synthesis, particular when using nanopore detection. As shown in the Examples, the tagged multi-nucleotide compounds of the present disclosure provide the ability to control parameters of DNA polymerase activity, such as processivity, transition rate, and read length, that allow for more accurate and efficient nucleic acid detection and sequencing.

Exemplary polymerases that may be used with the tagged multi-nucleotide compounds and methods of the present disclosure include the nucleic acid polymerases such as DNA polymerase (e.g., enzyme of class EC 2.7.7.7), RNA polymerase (e.g., enzyme of class EC 2.7.7.6 or EC 2.7.7.48), reverse transcriptase (e.g., enzyme of class EC 2.7.7.49), and DNA ligase (e.g., enzyme of class EC 6.5.1.1).

In some embodiments, the polymerase useful with tagged multi-nucleotides is 9°N polymerase, E. coli DNA Polymerase I, Bacteriophage T4 DNA polymerase, Sequenase, Taq DNA polymerase, 9° N polymerase (exo-)A485L/Y409V or Phi29 DNA polymerase (φ29 DNA Polymerase).

In some embodiments, the strand extending enzyme that incorporates the tagged multi-nucleotides comprises a DNA polymerase from *Bacillus stearothermophilus*. In some embodiments, the large fragment of DNA polymerase from *B. stearothermophilus*. In one embodiment, the polymerase is DNA polymerase Bst 2.0 (commercially available from New England BioLabs, Inc., Massachusetts, USA).

In some embodiments, the polymerase is a Pol6 DNA polymerase, or an exonuclease deficient variant of a Pol6, such as Pol6 having the mutation D44A. A range of additional Pol6 variants useful with the tagged multi-nucleotides of the present disclosure are described in U.S. Ser. No. 15/151,264, filed May 10, 2016, which is hereby incorporated by reference herein.

EXAMPLES

Various features and embodiments of the disclosure are illustrated in the following representative examples, which are intended to be illustrative, and not limiting. Those skilled in the art will readily appreciate that the specific examples are only illustrative of the invention as described more fully in the claims which follow thereafter. Every embodiment and feature described in the application should be understood to be interchangeable and combinable with every embodiment contained within.

Example 1: Preparation of Tagged Multi-Nucleotide Compounds

This example illustrates a general method for preparation of a tagged multi-nucleotide of structural formula (I) or (II), wherein the compound comprises two or three nucleotide linked to a single tag having a polymeric structure, such as an oligonucleotide tag structure as listed in Table 3, and/or comprising a sequence of SEQ ID NO: 1-109. Generally, any tag that can be modified with a propargyl group or other alkyne moiety.

This example describes the preparation of tagged multi-nucleotide compounds, $(dT6P)_2$-$(dT)_{30}$-C3, and $(dT6P)_3$-$(dT)_{30}$-C3 which correspond to compounds (3a) and (3b) shown below.

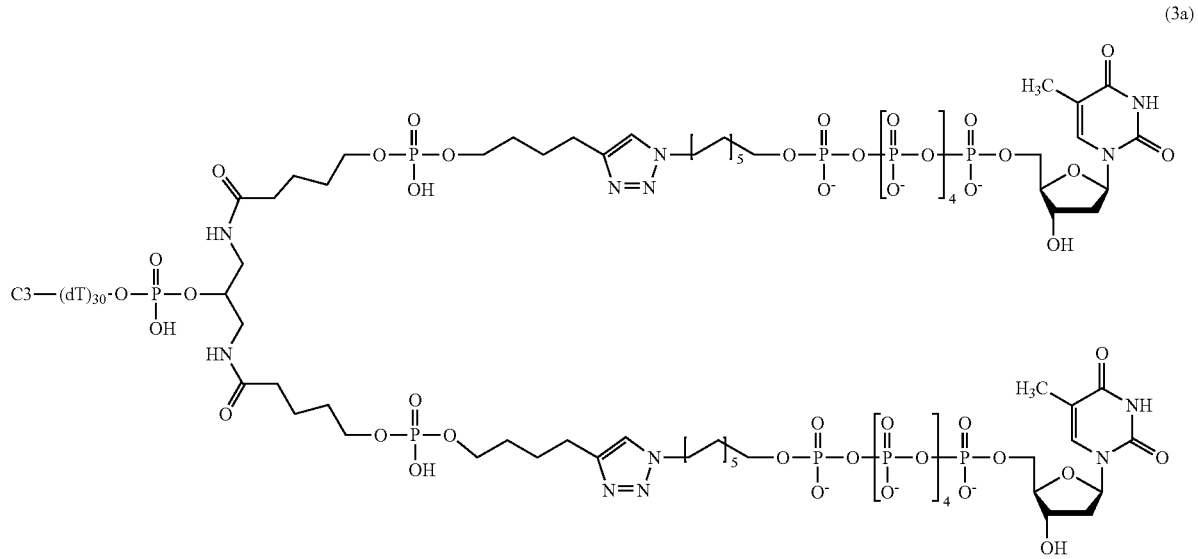

(3a)

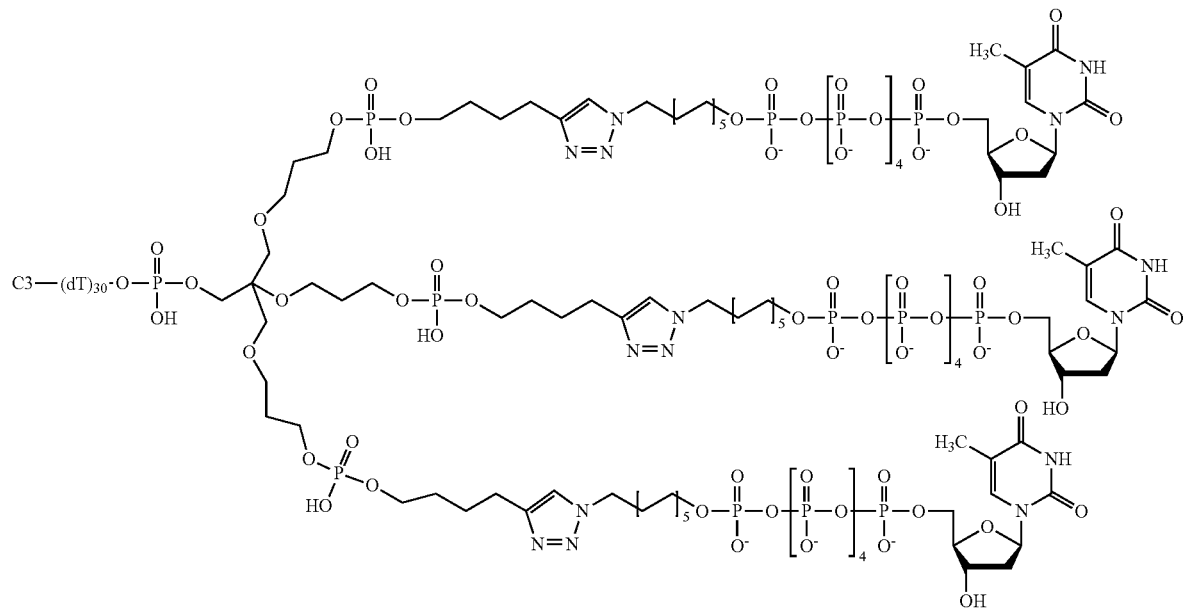
(3b)
The tagged-multi-nucleotides of compound (3a) and (3b) are synthesized via an azido-alkyne click reaction between a propargyl-modified "doubler" linker (or "Y-Linker") or "trebler" linker (or "W-Linker") attached to a single $dT_{30}$ oligonucleotide tag shown as compounds (2a) or (2b), respectively
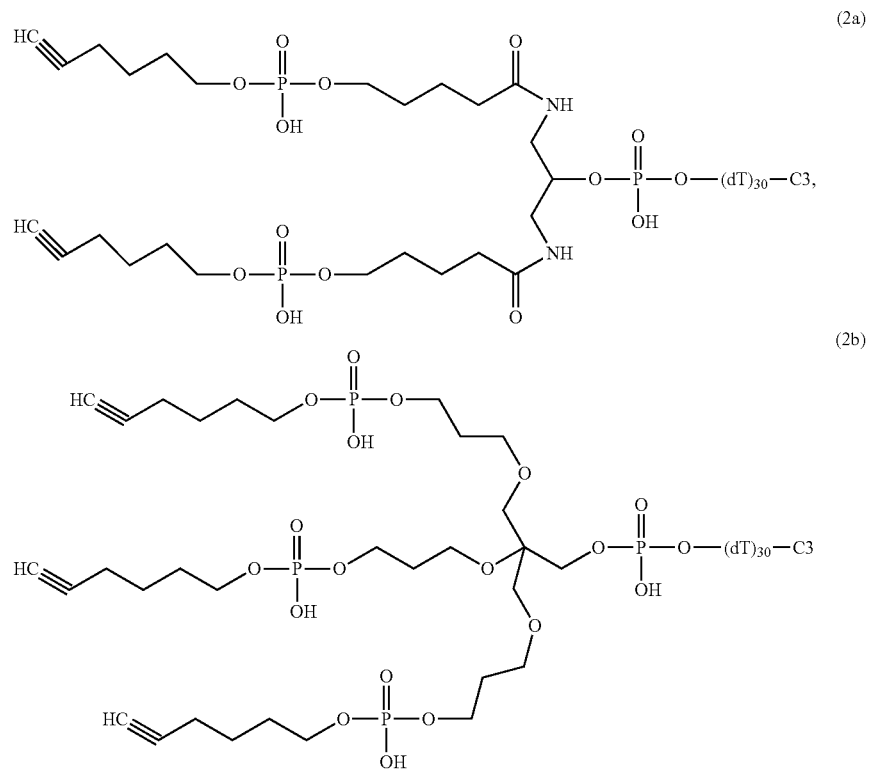
(2a)
(2b)

and an azide-linker-modified nucleoside hexaphosphate, dT6P—(CH$_2$)$_{11}$—N$_3$ of compound (1):

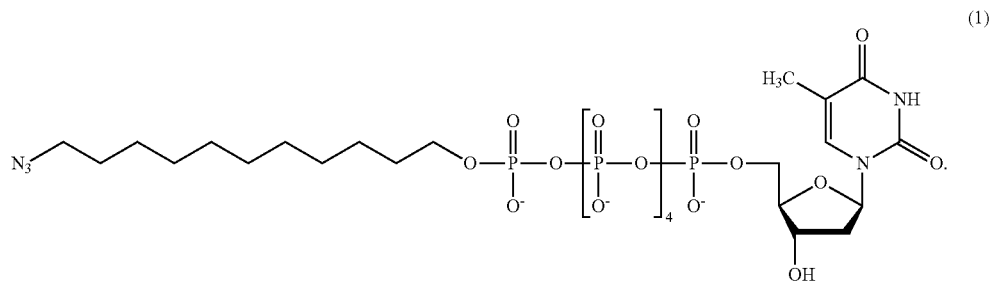

A. Synthesis dT6P-azide (Compound (1))

Preparation of 11-azido-1-undecanol 11-azido-1-undecanol is prepared according to the reaction Scheme 2 and procedure below:

Scheme 2

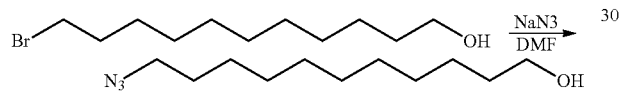

In a dried round bottom flask, sodium azide (1.44 g, 22 mM) was added to a solution of 11-Bromo-1-undecanol (1.84 g, 7.38 mmol) in anhydrous DMF (40 mL). The resulting white suspension was stirred under nitrogen atmosphere at ambient temperature overnight. The suspension was filtered and rinsed with DCM (50 mL). The solution was concentrated under vacuum to give yellowish oil. The compound can be used in the following steps without further purification.

Preparation of 11-azido-1-undecanyl triphosphate 11-azido-1-undecanyl triphosphate is prepared according to the reaction of Scheme 3 and procedure below:

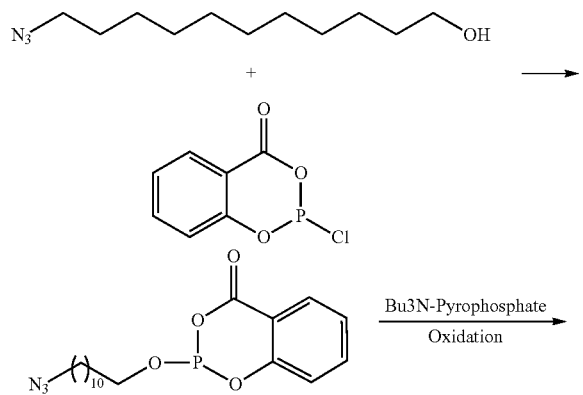

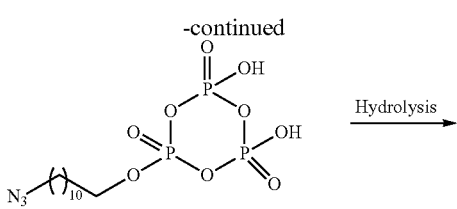

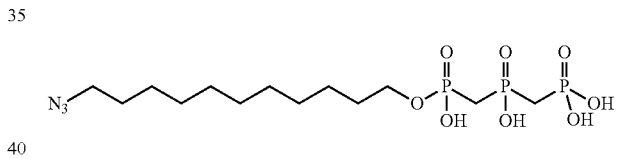

In a dried round bottom flask, 11-azido-1-undecanol (0.20 g, 0.94 mmol) was dissolved in anhydrous DMF (2.0 mL). Salicyl chlorophosphite (0.20 g, 1.03 mmol) was added in one portion. The resulting solution was stirred at ambient temperature under nitrogen for 45 minutes. In another flask, a solution of pyrophosphate tributylamine (0.566, 1.03 mmol) in anhydrous DMF and tributylamine (1.39 g, 7.51 mmol) was prepared and then added to the reaction solution. The resulting mixture was stirred for an hour and was oxidized with 20 mM iodine solution (80 mL, 1.55 mmol), giving cyclic meta-triphosphate intermediate that can be analyzed by mass spectrometer. After another hour of stirring, the reaction was quenched first with Na$_2$SO$_3$ (10%, 4 mL), allowed to stir for 20 minutes, followed by TEAB (0.10 M, 20 mL). The resulting mixture was stirred at ambient temperature overnight. The crude product was purified by TeleDyne CombiFlash RF+ column system using 30 g HP C18 column eluting with CH$_3$CN/0.1TEAA (0% to 50% CH$_3$CN in 16 minutes). The product was concentrated under vacuum and dried on a lyophilizer.

Preparation of dT6P-azide (Compound (1))

dT6P-azide is prepared according to the reaction of Scheme 4 and procedure below:

Scheme 4

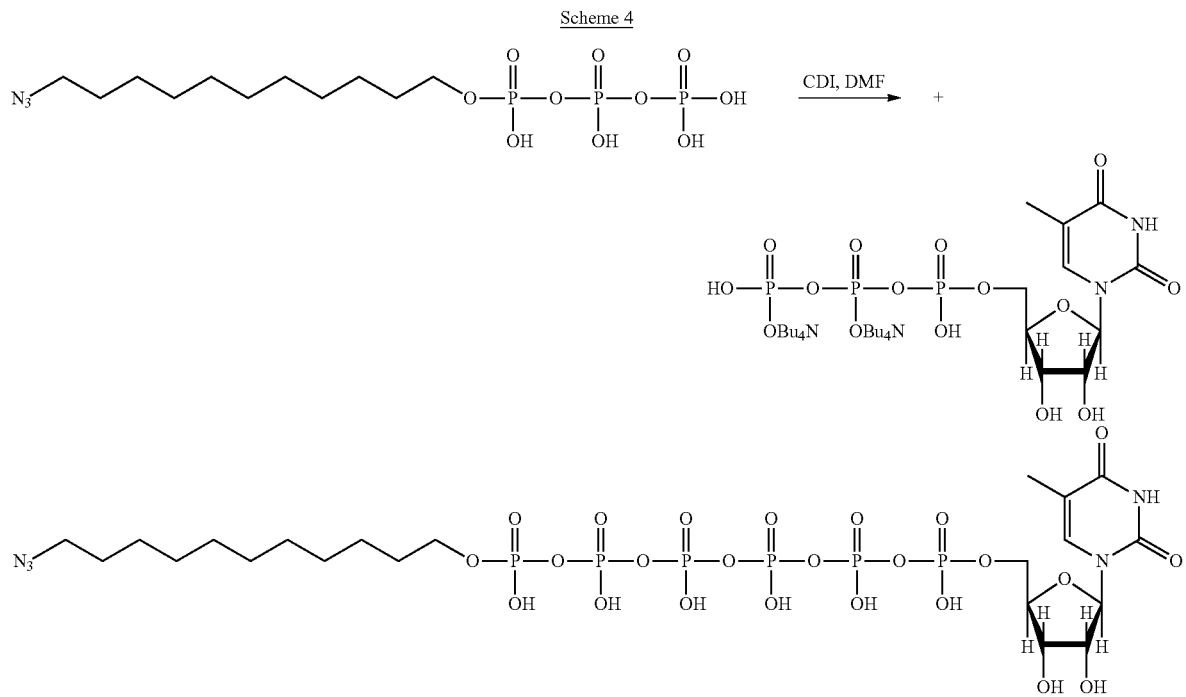

11-azido-1-undecanyl triphosphate (0.091 g, 0.12 mmol) was dissolved in anhydrous DMF (1.5 mL) and was activated with carbonyl diimidazole ("CDI") (0.078 g, 0.48 mmol) for 4 hours at ambient temperature. The excess CDI was quenched with methanol (0.029 mL, 0.72 mmol), stirring additional 30 minutes. Then a solution of dTTP+3Bu4N (0.20 g, 0.17 mmol) in anhydrous DMF (2.0 mL) was added, followed by $MgCl_2$ (0.114 g, 1.20 mmol). The resulting slurry solution was stirred for 24-36 hours at ambient temperature. The reaction was quenched with TEAB 0.1 M (20 mL), stirring for 30 minutes. The crude compound (1) was purified by ion-exchange chromatography (0.1 M to 1 M in 30 minutes), followed by RP-C18 HPLC (10-45% $CH_3CN$ in 35 minutes) to yield 15-30 μmol of product. The formation of the compound (1) was confirmed by mass spectrometry (cal. 917.06, observed 916.03 for negative ion).

B. Synthesis of $dT_{30}$ Tag with Propargyl-Modified Doubler and Trebler Linkers (Compounds (2a) and (2b))

The $dT_{30}$ oligonucleotide used as a tag was synthesized on an ABI 3900 DNA Synthesizer using standard solid phase phosphoramidite chemistry protocols and commercially available reagents. In the penultimate synthesis step the doubler linker phosphoramidite unit of compound (19) or the trebler linker phosphoramidite unit of compound (20).

Then, in the final automated oligonucleotide synthesis step a propargyl-$C_5$-phosphoramidite linker was added resulting in the propargyl-modified doubler and trebler reagents of compounds (2a) and (2b), respectively.

C. Click Conjugation of Nucleotides to Tags with Doubler or Trebler Linkers to Form Tagged Multi-Nucleotides of Compound (3a) and Compound (3b)

Doubler Linker Conjugation:

The doubler-linker conjugation reaction to tagged multi-nucleotide compound (3a) is carried out according to the general reaction scheme depicted in FIG. 1 and the following procedures. dT6P-azide (compound (1)) (300 nmol) and doubler-dT$_{30}$-C3 (compound (2a)) (100 nmol) were mixed in DI-water (100 μL). The conjugation was initiated by copper-catalyzed azido-alkyne click-reaction according to the standard literature procedure using Cu(I) bromide (6000 nmol) and THPTA (4000 nmol) in a mixture solution of DMSO/t-Butanol (3:1). The reaction solution was mixed at ambient temperature overnight on a shaker. The crude mixture was purified by RP C18-HPLC (0.1M TEAA/CH3CN). Formation of the desired conjugated product of compound (3a) was confirmed by mass spectrometer (cal. 11708; observed 11708.97 for negative ion).

Figure 2:
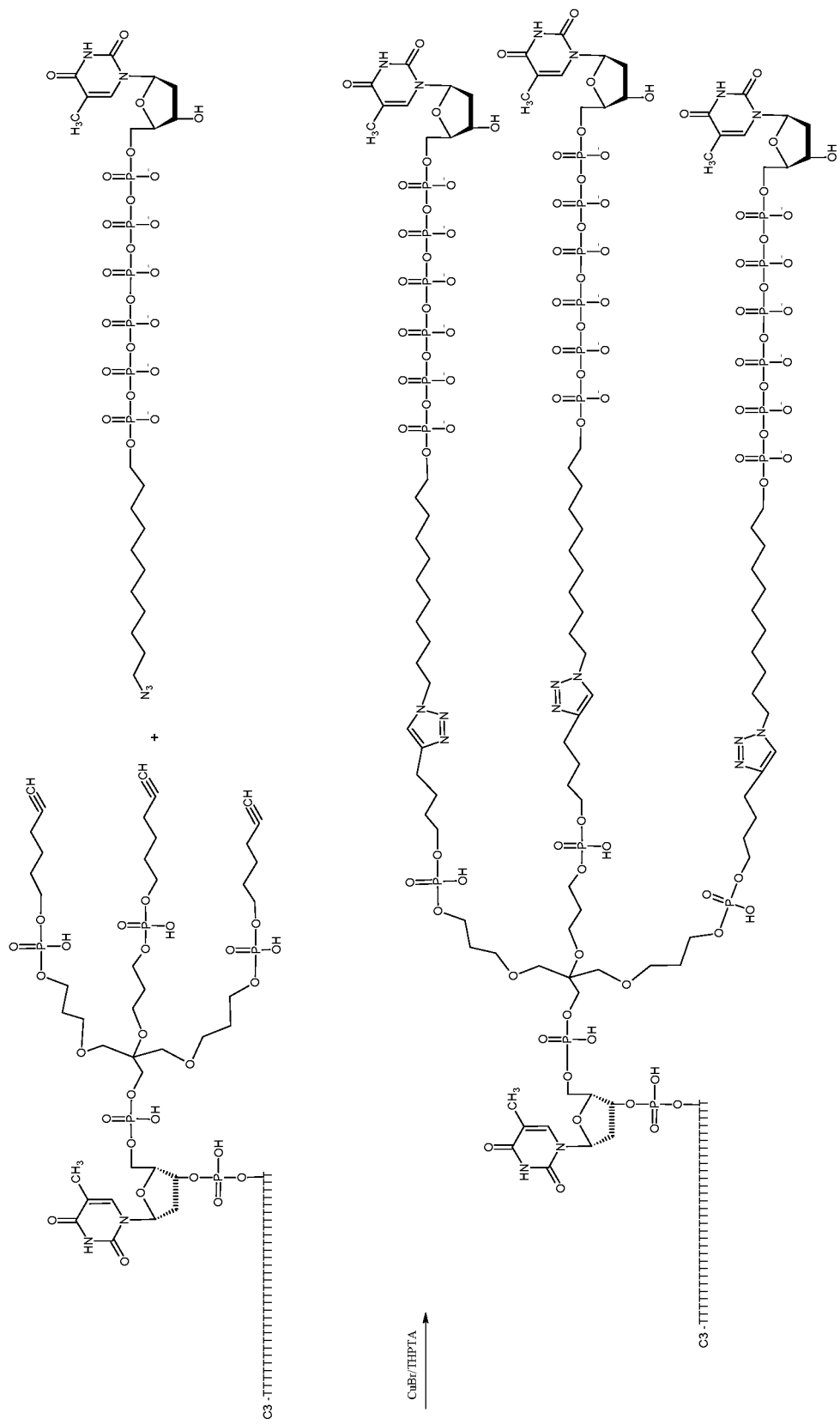
FIG. 2 depicts a trebler-linker conjugation reaction useful for preparing the tagged multi-nucleotide substrate of the structure [dT6P-linker]$_3$-$dT_{30}$-$C_3$ (compound (3b)).

Trebler Linker Conjugation:

The trebler-linker conjugation reaction to tagged multi-nucleotide compound (3b) is carried out according to the general reaction scheme depicted in FIG. 2 and the following procedure similar to that used for the doubler-linker conjugation. dT6P-azide (compound (1)) (450 nmol) and trebler-dT$_{30}$-C3 (compound (2b)) (100 nmol) were mixed in DI-water (100 μL). The conjugation is initiated using Cu(I) bromide (6000 nmol) and THPTA (4000 nmol) and mixed at a temperature of 40 C overnight on a shaker. The crude mixture is purified by HPLC and formation of the desired conjugated product of compound (3b) confirmed by mass spectrometer (cal. 12804.7; observed 12806.62 for negative ion).

Example 2: Comparative Polymerase Substrate Characteristics of Tagged Multi-Nucleotides This example illustrates the improved polymerase substrate characteristics of the tagged multi-nucleotide compounds which comprise two nucleotides linked to a single tag relative to a standard tagged nucleotide compound having a single oligonucleotide tag linked to a single nucleotide.

Assay Protocol:

The assay is a displacement assay that uses an exonuclease deficient variant of the Pol6 polymerase (e.g., "Pol6-44 D44A" which is a variant having a D44A mutation), together with a Cy5-labeled displacement template and a BHQ-labeled quencher primer. A range of additional Pol6 variants useful for nanopore sequencing are available and can be used in the assay of this example, such as the Pol6 variants disclosed in U.S. Ser. No. 15/151,264, filed May 10, 2016, which is hereby incorporated by reference herein. An assay solution containing the Pol6 polymerase, 5'-Cy5-labelled displacement DNA template, and 3'-BHQ-labelled quencher primer in 75 mM potassium glutamate ("K-Glu") is prepared in the absence of any substrate or Mg$^{2+}$ ion (other buffer conditions: 25 mM HEPES, 0.2 mM EDTA, 0.05% Triton X-100, 5 mM TCEP, 25 μg/mL BSA, pH 7.5).

The DNA displacement template is a hairpin sequence 5'-labeled with Cy5 and a 3 carbon spacer near the 3' end: /5Cy5/AGA GTG ATA GTA TGA TTA TGT AGA TGT AGG ATT TGA TAT GTG AGT AGC CGA ATG AAA CCT T/iSpC3/TT GGT TTC ATT CGG (SEQ ID NO: 124). The quencher primer sequence 3'-labelled with BHQ-2 is: TTT TCA TAA TCA TAC TAT CAC TCT/3BHQ_2/(SEQ ID NO: 125). ("BHQ-2"=BLACK HOLE QUENCHER-2=4'-(4-Nitro-phenyldiazo)-2'-methoxy-5'-methoxy-azobenzene-4"-(N-ethyl-2-O-(4,4'-dimethoxytrityl))-N-ethyl-2-O-glycolate-CPG; available from Glen Research, Sterling, Va., USA)

A solution, containing the tagged multi-nucleotide compound to be tested and the three other nucleotide-hexaphosphate ("dN6P") substrates (i.e., dA6P, dC6P, dG6P) required for polymerase synthesis of a strand complementary to the DNA template, is added to the polymerase solution. Additional K-Glu is added to bring the total K-Glu concentration in the mixture up to 300 mM. The polymerase reaction is then initiated by addition of MgCl$_2$. The final concentrations in the assay reaction mixture are: 100 nM Pol6-44 D44A enzyme, 50 nM Cy5 displacement DNA template, 40 μM each of other dN6P substrates, 300 mM K-Glu, 25 mM HEPES, 0.2 mM EDTA, 0.05% Triton X-100, 5 mM TCEP, 25 μg/mL BSA, 5 mM MgCl$_2$, pH 7.5. Assays are carried out for each of the test substrates at the following initial concentrations: 0 μM, 5 μM, 10 μM, 20 μM, and 50 μM. Polymerase activity is followed by fluorometrically monitoring the change in FRET between the Cy5 and BHQ labels as the polymerase incorporates the substrates in the DNA extension reaction.

The specific polymerase substrates tested in the assay protocol and the results of the assays are shown in Table 6:

TABLE 6

| Substrate | Tag (SEQ ID NO:) | Initial Conc. (μM) | | | | |
|---|---|---|---|---|---|---|
| | | 50 | 20 | 10 | 5 | 0 |
| | | Rate ($k_{cat} + k_{on}$) | | | | |
| dT6P | n/a | 2.59 | 2.52 | 2.28 | 1.79 | 0.00 |
| dT6P-Cy3-(N3CET)$_{30}$-C3 | 100 | 1.71 | 1.24 | 0.86 | 0.67 | 0.00 |
| (dT6P)$_2$-(dT)$_{30}$-C3 (compound (3a)) | 101 | 0.55 | 1.29 | 1.48 | 1.37 | 0.00 |
| dT6P-dT$_{30}$-C6-dT6P (i.e., dT6P at each of the 5' and 3' ends of a dT$_{30}$-C6 tag.) | 10 | 1.82 | 1.34 | 1.15 | 0.63 | 0.00 |

As shown by the polymerase assay results in Table 6, the tagged multi-nucleotide compound, [dT6P-Linker]$_2$-(dT)$_{30}$-C3 which has two nucleotides covalently linked through a doubler linker to a single dT$_{30}$-C3 oligonucleotide tag (SEQ ID NO: 101) exhibited an initial rate twice that of the single dT6P nucleotide substrate with a single dT$_{30}$-C3 oligonucleotide tag. This increased rate ($k_{cat}+k_{on}$) of polymerase activity is consistent with the tagged multi-nucleotide substrate having a significantly increased on-rate and/or effective concentration at the polymerase active site.

Example 3: Comparative Polymerase Substrate Characteristics of Single, Double, Triple, and Quadruple-Nucleotides Linked to a Single Tag This example illustrates the improved polymerase substrate characteristics of tagged multi-nucleotide compounds which comprise two, three, or four nucleotides linked to a single tag relative to a standard tagged nucleotide compound having a single oligonucleotide tag linked to a single nucleotide.

The standard tagged single nucleotide substrate used in this example is dA6P-dT$_{30}$-C3 ("Full Tag") of compound (3d) which include a dA6P moiety linked to the dT30-C3 oligonucleotide tag through a "C11-triazole-C4" linker of structural formula (XVd) (formed via standard click-chemistry) as shown below:

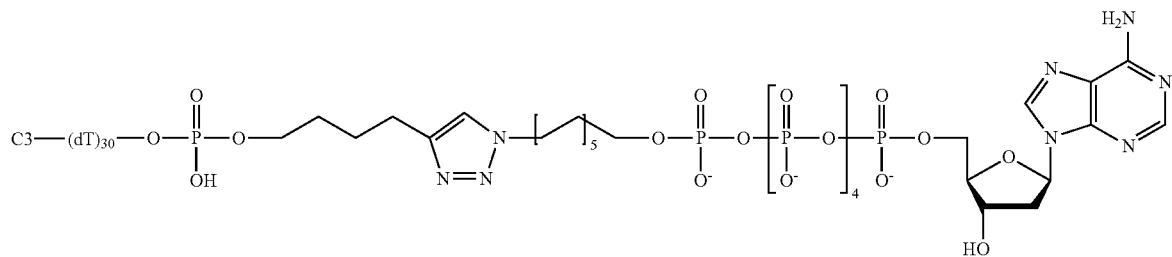

(3d)

The tagged multi-nucleotide compounds used in this example are: (dT6P)$_2$-(dT)$_{30}$-C3 ("Y-tag"), and (dT6P)$_3$-(dT)$_{30}$-C3 ("W-tag"), which correspond to compounds (3a) and (3b), respectively (see Example 1). The example also describes the polymerase substrate characteristics of a multi-nucleotide compound with four nucleotides via a quaternary linker, (dT6P)$_4$-(dT)$_{20}$-C3 ("Q-Tag"), which corresponds to compound (3c):

(3c)
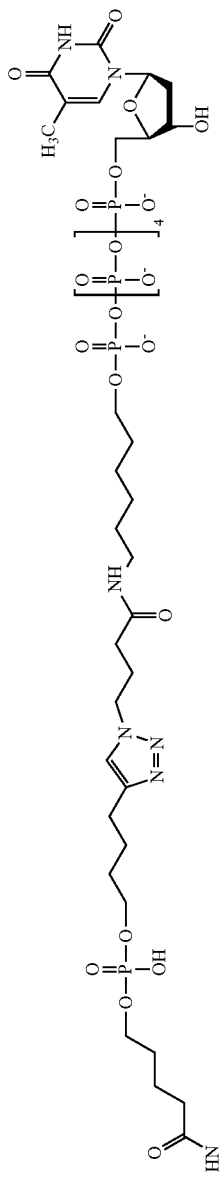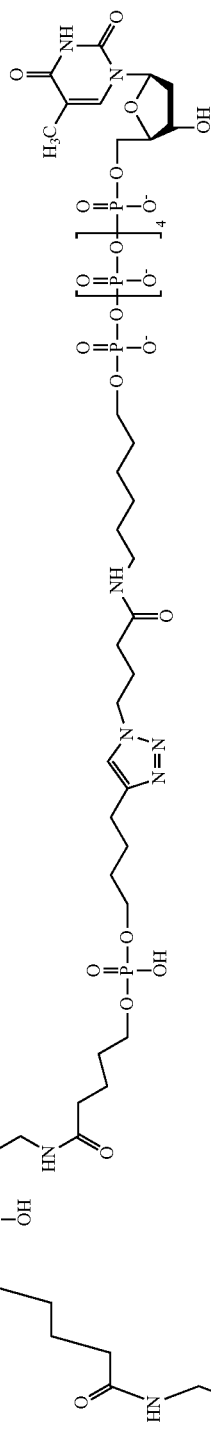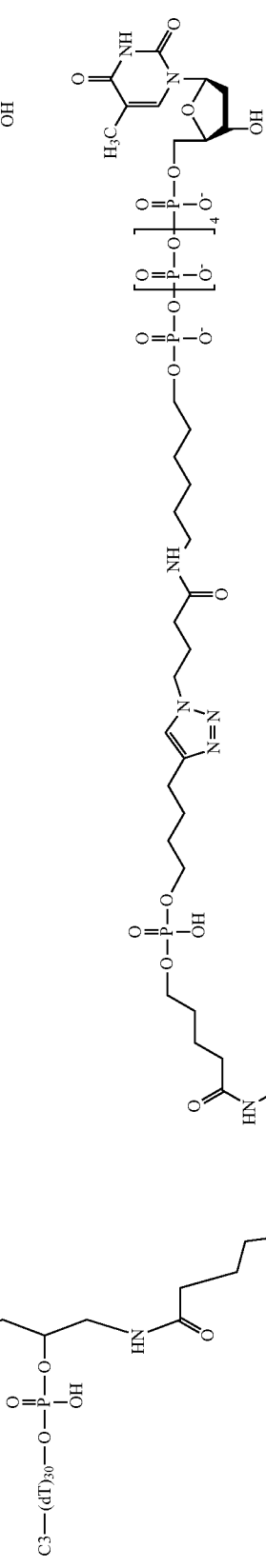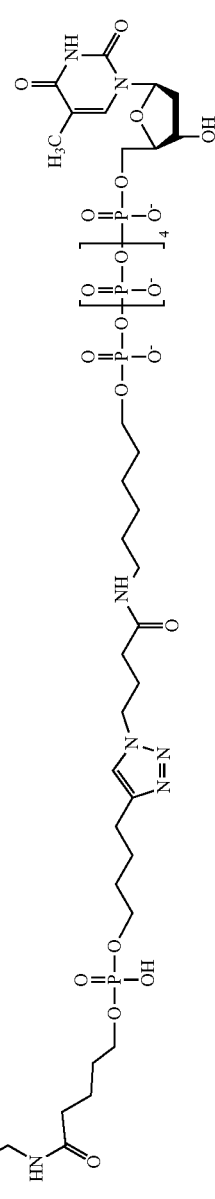

A. Synthesis of "Q-Tap" of Compound (3c)

1. The reagent, 6-(Fmoc-amino)-1-hexanol monophosphate (2) was prepared according to the reaction of Scheme 5 and procedure described below:

Scheme 5

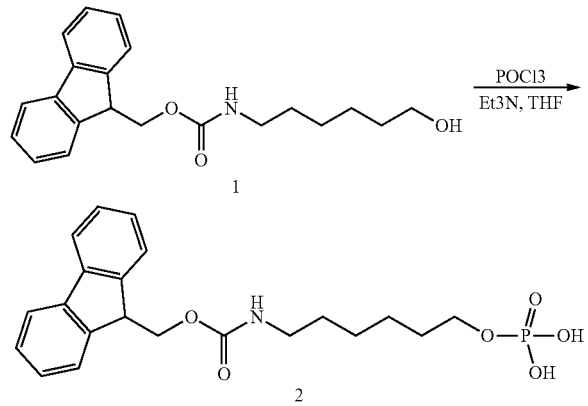

6-(Fmoc-amino)-1-hexanol (2.54 mmol) was co-evaporated with anhydrous acetonitrile (20 mL) three times and then placed under high vacuum for an hour. The yellow oil was dissolved in anhydrous THF (12 mL), followed by triethylamine (5.58 mmol). The solution was cooled with an ice-bath. After about 10 minutes, $POCl_3$ (5.70 mmol) was added via a syringe. The reaction solution was allowed to stir at ambient temperature overnight. The reaction was quenched with water and stirred for 4 hours. The solution was adjusted to pH 9 with saturated aqueous $NaHCO_3$ and was washed with ethyl acetate (20 mL) twice to remove organic soluble impurities. The aqueous solution was then adjusted to pH 1 with concentrated HCl. The solution was extracted with 3× with 20 mL ethyl acetate to recover the product. The ethyl acetate solution was dried with $Na_2SO_4$ and then concentrated under a rotavap to give yellow oil. The product 6-(Fmoc-amino)-1-hexanol monophosphate can be used in the preparation of 6-(Fmoc-amino)-1-hexanol triphosphate without further purification.

2. The reagent, 6-(Fmoc-amino)-1-hexanol triphosphate (3) was prepared according to the reaction of Scheme 6 and procedure described below:

Scheme 6

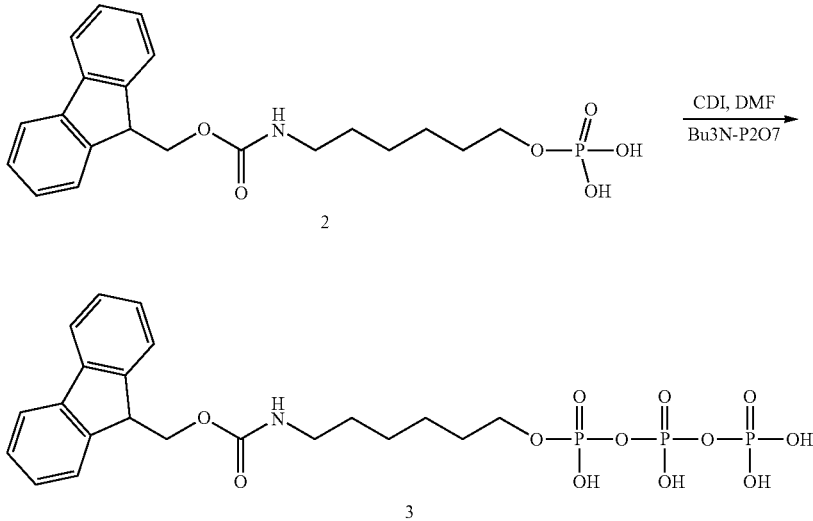

6-(Fmoc-amino)-1-hexanol monophosphate (1.02 mmol) of step 1 (above) was co-evaporated with anhydrous acetonitrile (20 mL×3) and was placed under vacuum for 1 hour. The oil was taken up in anhydrous DMF (4 mL) and CDI (4.1 mmol) was added in one portion, stirring under nitrogen at ambient temperature for 4 hours. Methanol (6.14 mmol) was added and allowed to stir for 30 minutes to decompose excess CDI in the solution. Then a solution of $Bu_3N$-$P_2O_7$ (2.56 mol) in DMF (2 mL) was added, stirring under nitrogen at ambient temperature overnight. The reaction was quenched with TEAA (0.1 M, 50 mL). After about 30 minutes, the crude product was purified by LC-TeleDyne CombiFlash RF+ column system on 30 g HP C18, eluting with 0.1M TEAA/$CH_3CN$ (0-50% $CH_3CN$ in 20 minutes). The solution was concentrated on a speed-vac and then lyophilized to give the desired 6-(Fmoc-amino)-1-hexanol triphosphate as a white solid.

3. The nucleotide-hexaphosphate-linker reagent, dT6P-C6-NH$_2$ (6) was prepared according to the reaction of Scheme 7 and procedure described below:
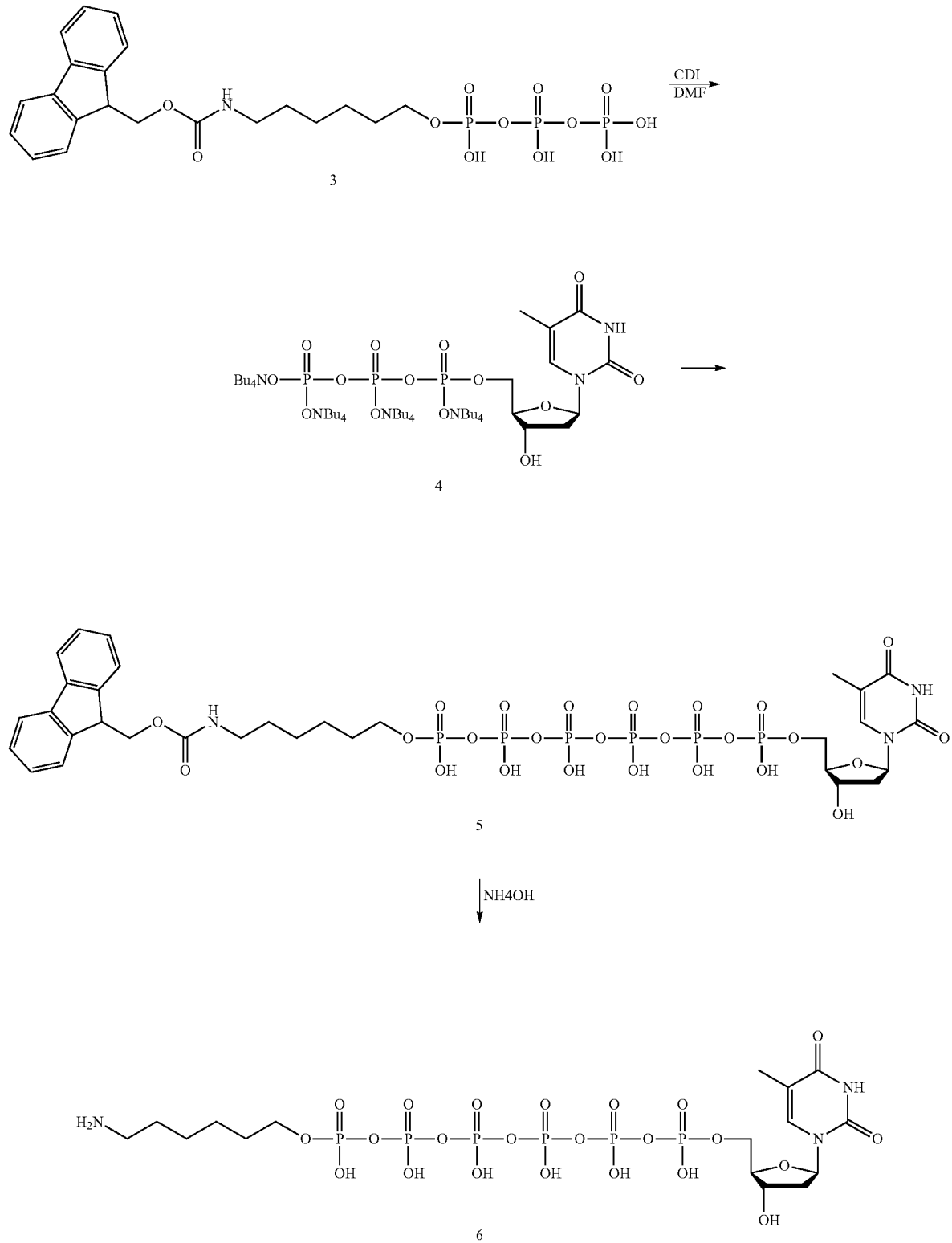
Scheme 7

The κ-(Fmoc-amino)-1-hexanol triphosphate (0.291 mmol) reagent of step 2 (above) was co-evaporated with anhydrous acetonitrile three times and then placed under high vacuum for an hour. The oil residue was taken up in anhydrous DMF (2.50 mL) and the triphosphate was reacted with CDI (1.16 mmol), stirring under nitrogen for 4 hours at ambient temperature. Methanol (1.74 mmol) was added to quenched remaining unreacted CDI. After another 30 minutes, a solution of dTTP+$(Bu_4N)_4$ (0.407 mmol) solution in DMF (2 mL) was added, followed by anhydrous $MgCl_2$ (2.9 mmol). The resulting suspension was stirred under nitrogen for 72 hours at ambient temperature. Then it was quenched with TEAA (0.1 M, 50 mL), stirring for an hour. The crude mixture was eluted through Sephadex-A25 DEAE ion exchange column using TEAA (0.1 M to 1 M gradient) to remove ion impurities. The product fractions were collected, analyzed by mass spectrometer, and then concentrated on a speed-vac. The recovered product was treated with concentrated ammonium hydroxide for 2 hours at ambient temperature to remove the Fmoc protecting group. The product was purified by HPLC on C18-column, eluting with 0.1M TEAA/CH3CN (10-50% CH3CN in 45 minutes) to give pure product dT6P-C6-$NH_2$ (6).

4. The azide-modified nucleotide hexaphosphate reagent, dT6P-C6-$N_3$ (6) was prepared according to the reaction of Scheme 8 and procedure described below:

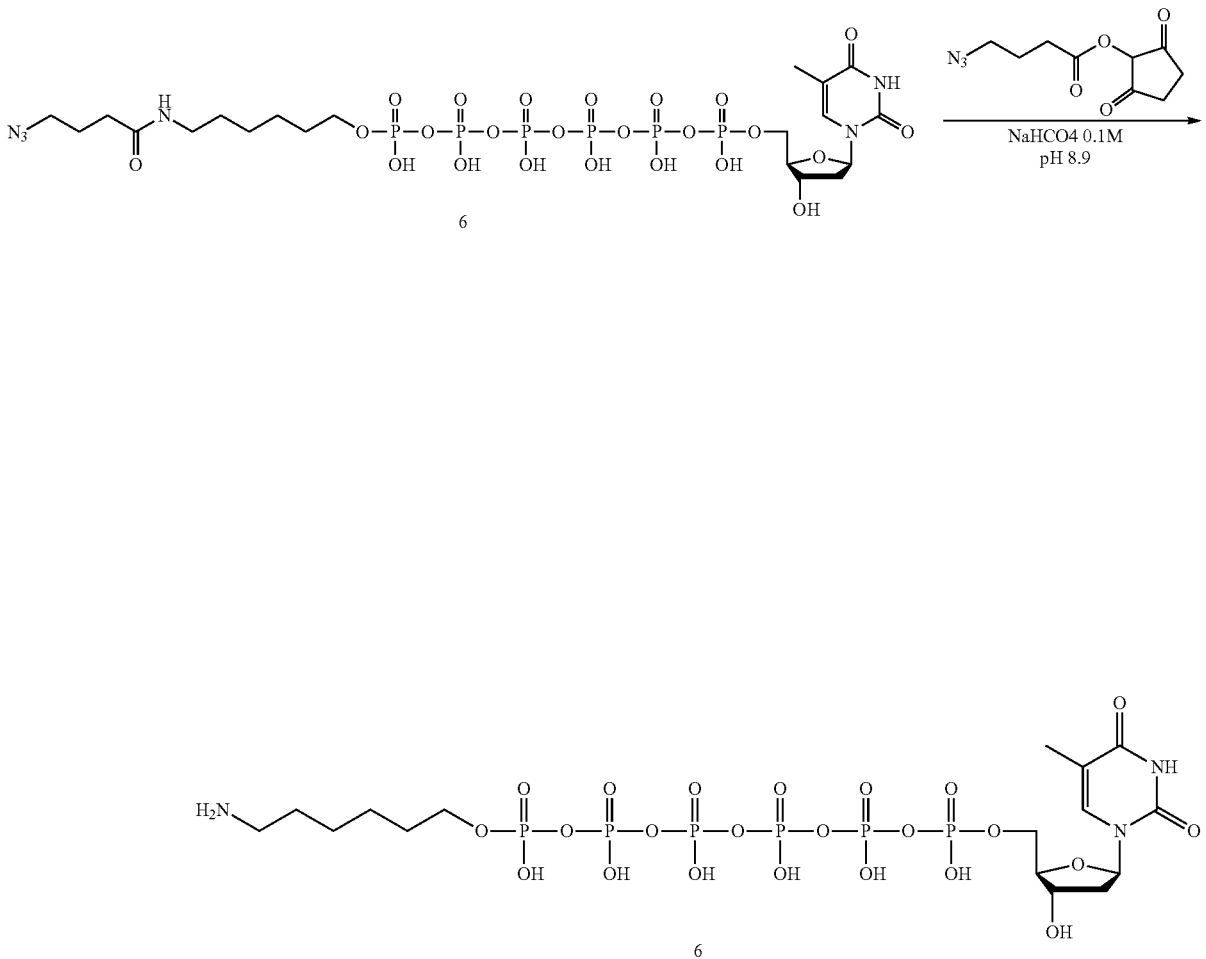

Scheme 8

The dT6P-C6-$NH_2$ product (2 μmol) of step 3 (above) was dried on a speed-vac and re-dissolved 400 μL of $NaHCO_3$ solution (0.1 M, pH 8.9). Then a solution of azidobutyric acid NHS ester (5 μmol, 125 mM in DMF) was added. The solution was mixed vigorously and placed on a Thermo-mixer at ambient temperature overnight. Purification was carried out on a HPLC C18 column using 0.1M TEAA/$CH_3CN$ as solvents and gradient of 10-40% $CH_3CN$ in 40 minutes.

5. The reagent of compound (2c) comprises a single $dT_{20}$-C3 tag attached via phosphodiester linkages to a "quaternary linker" with four propargyl reactive groups available for click-chemistry attachment to four azide-modified nucleotides.

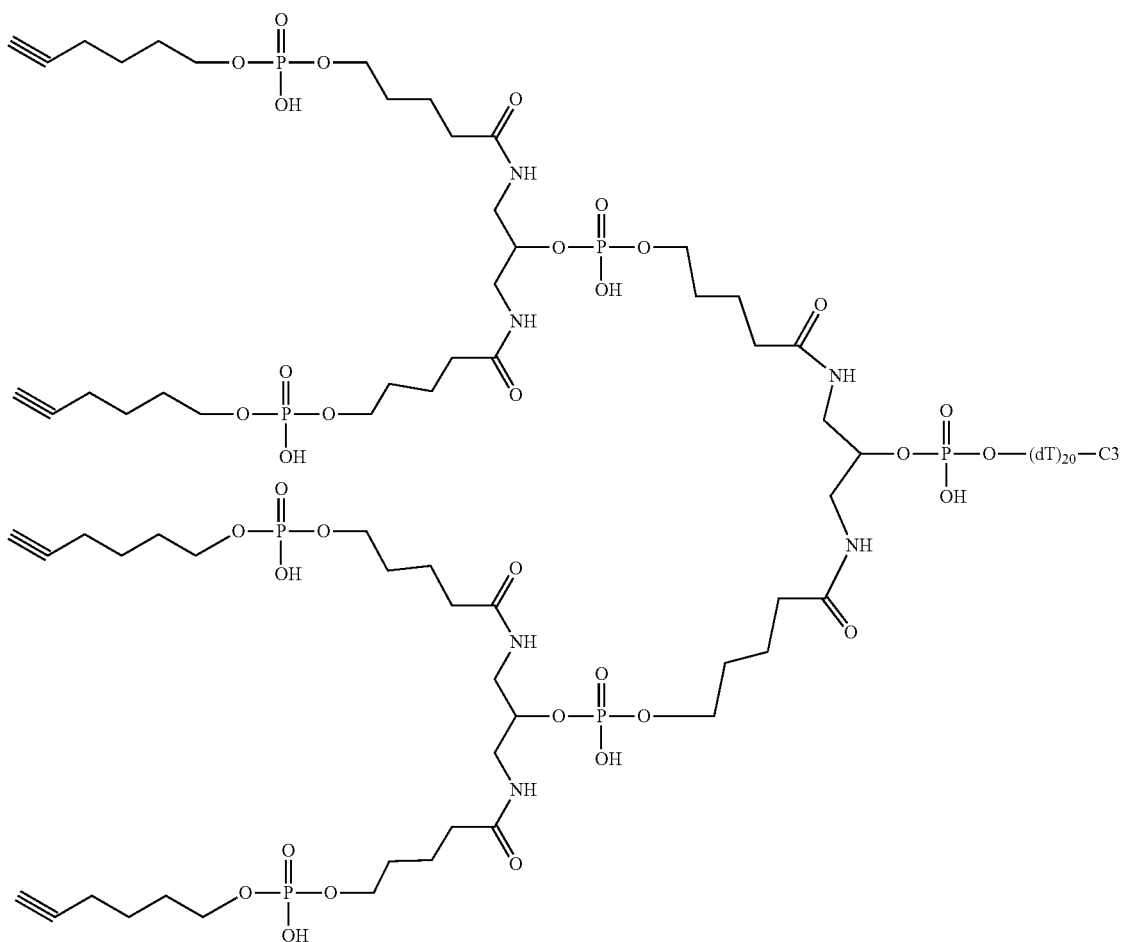

(2c)

The quaternary linker with dT$_{20}$-C3 tag reagent of compound (2c) is synthesized on an ABI 3900 DNA synthesizer generally as described for compound (2b) in Example 1, except that a second consecutive doubler-linker phosphoramidite unit of compound (19) is added in the penultimate oligonucleotide synthesis step. The second doubler linker results in a total of four DMT protected groups available for the addition of a propargyl-C$_5$-phosphoramidite linker to each of the four available groups on the two doubler-linkers. The resulting product is the quaternary linker of compound (2c).

6. The quaternary-linker of compound (2c) produced in step 5 (above) is conjugated via click-chemistry with the azide-modified nucleotide, dT6P-C6-N$_3$ of step 4 to produce the "Q-Tag" multi-nucleotide of compound (3c), which comprises a "C6-amide-C4-triazole-C4" linker of formula (XVe) between the terminal phosphate of the dT6P and the doubler-linker. The reaction is carried out according to the general reaction of scheme described in Example 1, step C for doubler-linker conjugation. Briefly, dT6P-C6-N$_3$ (525 nmol) and the quaternary linker reagent of compound (2c) (87.5 nmol) are mixed in DI-water (100 μL). The conjugation reaction is initiated using Cu(I) bromide (8000 nmol) and THPTA (12000 nmol) and that reaction mixed at 40 C overnight on a shaker. The resulting crude product mixture is purified by HPLC. Formation of the conjugated "Q-Tag" product of compound (3c) confirmed by mass spectrometer (cal. 11521.1; observed 11527.13 for negative ion).

B. Assay Protocol

The assay is a displacement assay using an exonuclease deficient variant of the Pol6 polymerase as described in Example 2, wherein polymerase activity is followed by fluorometrically monitoring the change in FRET between the Cy5 and BHQ labels as the polymerase incorporates the substrates in the DNA extension reaction.

Figure 3:
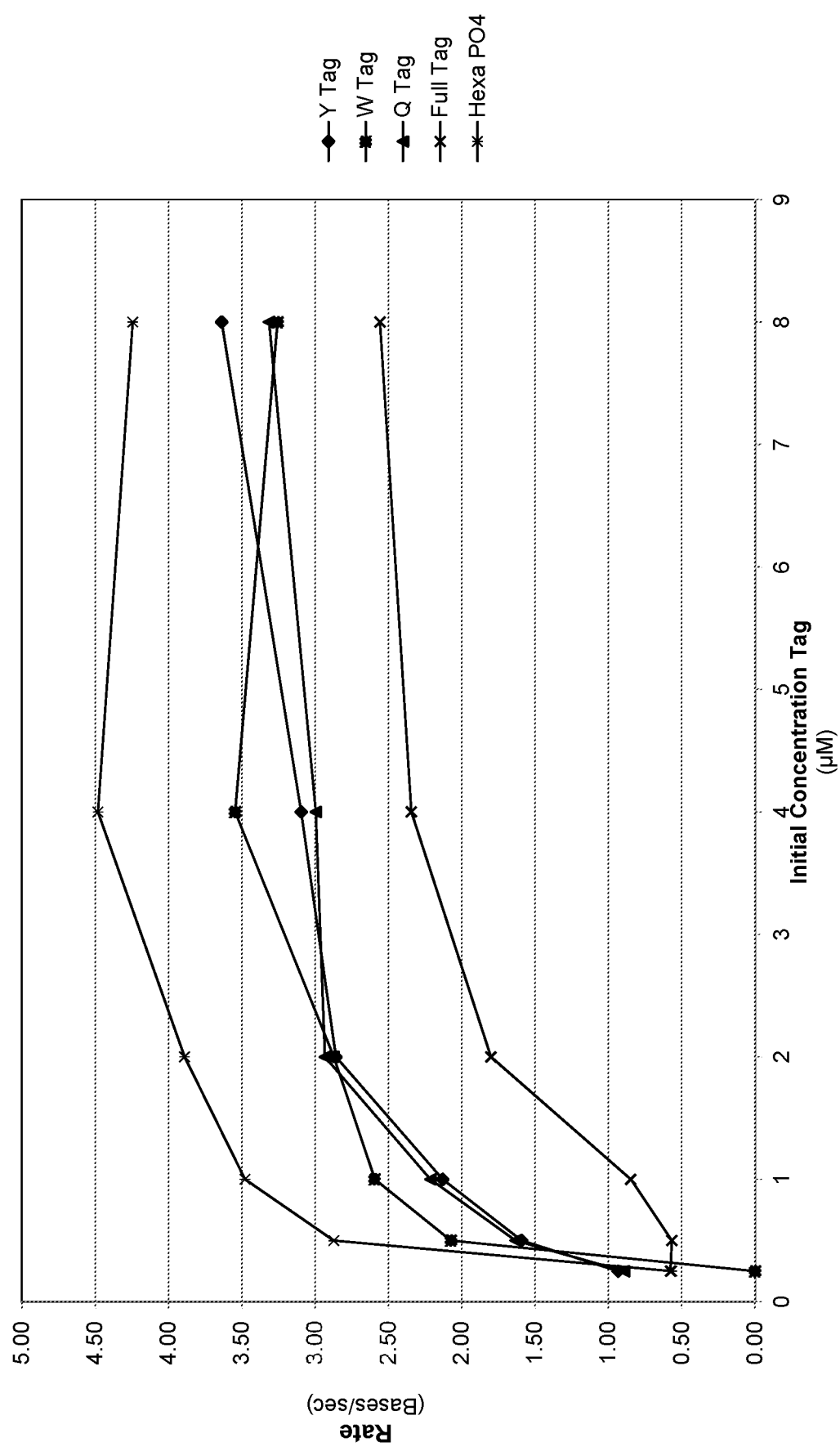
FIG. 3 depicts a plot of tag concentration versus rate (bases/sec) as a polymerase substrate in displacement assays of tagged multi-nucleotide substrates having 2, 3, and 4 substrates linked to a single oligonucleotide tag, as well as, a tagged single nucleotide substrate, and an un-tagged nucleotide hexaphosphate substrate.

Briefly, an assay solution containing the Pol6 polymerase, the 5'-Cy5-labelled displacement DNA template of SEQ ID NO: 124, and the 3'-BHQ-labelled quencher primer of SEQ ID NO: 124 in 75 mM potassium glutamate ("K-Glu") is prepared in the absence of the substrate or Mg$^{2+}$ ion. A substrate solution is prepared containing either the multi-nucleotide compound to be assayed (i.e., "Y-Tag," "W-Tag," or "Q-Tag"), the non-tagged dT6P ("Hexa-PO4), or the tagged single nucleotide substrate, dA6P-dT$_{30}$-C3 ("Full Tag") of compound (3d). Also included in the substrate solution are the other three nucleotide-hexaphosphate ("dN6P") substrates required for polymerase synthesis of a strand complementary to the DNA template (i.e., dA6P, dC6P, dG6P). This substrate solution is added to the polymerase solution. Assays are carried out for each of the test substrates at the following initial concentrations: 0.25 μM, 0.5 µM, 1.0 µM, 2.0 µM, 4.0 µM, and 8.0 µM. Additional K-Glu is added to bring the total K-Glu concentration in the mixture up to 300 mM. The polymerase reaction is then initiated by addition of $MgCl_2$. Final concentrations in the assay reaction mixture are: 100 nM Pol6 enzyme, 50 nM Cy5 displacement DNA template, 40 µM each of other dN6P substrates, 300 mM K-Glu, 25 mM HEPES, 0.2 mM EDTA, 0.05% Triton X-100, 5 mM TCEP, 25 µg/mL BSA, 5 mM $MgCl_2$, pH 7.5. The initial rates are plotted as shown in FIG. 3 and the concentrations and rate values summarized in Table 7.

TABLE 7

| Substrate | Tag (SEQ ID NO:) | Initial Conc. Tag (µM) | | | | | |
|---|---|---|---|---|---|---|---|
| | | 8.0 | 4.0 | 2.0 | 1.0 | 0.5 | 0.25 |
| | | Rate (Bases/sec) | | | | | |
| dT6P ("Hexa-PO4") | n/a | 4.24 | 4.48 | 3.89 | 3.48 | 2.87 | 0.57 |
| dA6P-dT$_{30}$-C3 ("Full Tag" of compound (3d)) | 101 | 2.56 | 2.34 | 1.80 | 0.85 | 0.57 | 0.58 |
| (dT6P)$_2$-(dT)$_{30}$-C3 ("Y-Tag" of compound (3a)) | 101 | 3.64 | 3.09 | 2.86 | 2.13 | 1.59 | 0.93 |
| (dT6P)$_3$-(dT)$_{30}$-C3 ("W-Tag" of compound (3b)) | 101 | 3.26 | 3.54 | 2.87 | 2.59 | 2.07 | 0.00 |
| (dT6P)$_4$-(dT)$_{20}$-C3 ("Q-Tag" compound (3c)) | 101 | 3.31 | 2.99 | 2.93 | 2.21 | 1.63 | 0.89 |

[1]Single-dN6P substrates include C11-triazole-C4 linker (as in compound (3d)) between terminal hexaphosphate moiety and tag sequence.
[2]Double-dN6P substrates include doubler-linker (as in compound(3a)) between terminal hexaphosphate moiety and tag sequence.
[3]Abbreviations for tag sequences are those commonly used for oligonucleotide synthesis (see e.g., abbreviations in Table 3).

As shown by the results of FIG. 3 and Table 7, the tagged multi-nucleotide compounds with two of more nucleotides exhibit initial rates nearly twice that of the single nucleotide substrate with a single dT$_{30}$-C3 oligonucleotide tag ("Full Tag") of compound (3d). The tagged double-, triple-, and quadruple-nucleotide substrates of compounds (3a), (3b), and (3c), exhibit comparably increased rates. The increased rate of polymerase activity is consistent with the tagged multi-nucleotide substrate having a significantly increased on-rate and/or effective concentration at the polymerase active site. Further increases in the rates of the triple- and quadruple-nucleotide substrate may be obtainable through optimization of the distance of the nucleotides from the doubler and trebler linker branch points in these compounds.

Example 4: Use of Tagged Multi-Nucleotides for Nanopore Sequencing

This example illustrates the improved characteristics of a set of four differently tagged multi-nucleotide compounds, each of which comprises a different single 20-mer length oligonucleotide tag covalently linked via a doubler-linker to two nucleotide hexaphosphate (dN6P) moieties, each capable of being a polymerase substrate. These tagged multi-nucleotides are compared to a set of tagged single nucleotide compounds, wherein the set of tags comprises a comparable 30-mer oligonucleotides connected to the nucleotide substrate via the C11-triazole-C4 linker as in compound (3d). The use of a 30-mer oligonucleotide tag in the single nucleotide substrates accounts for a shorter linker relative to the multi-nucleotide substrates which include the additional doubler-linker between the nucleotide substrate and tag. The two sets of tagged dN6P substrates compared in the example are shown in Table 8.

TABLE 8

| | Tag[3] (SEQ ID NO:) |
|---|---|
| Single-dN6P Substrate Set[1] | |
| dA6P-Cy3-dT$_4$-(dSp-dT)$_4$-dT$_{18}$-C3 | 72 |
| dC6P-Cy3-dT$_{30}$-C3 | 34 |
| dT6P-Cy3-dT$_4$(N3CET)$_3$-dT$_{23}$-C3 | 102 |
| dG6P-dT$_6$-(Tmp)$_6$-dT$_{18}$-C3 | 103 |
| Double-dN6P Substrate Set[2] | |
| (dA6P)$_2$-dT$_4$-(dSp-dT)$_4$-dT$_8$-C3 | 104 |
| (dC6P)$_2$-dT$_{20}$-C3 | 105 |
| (dT6P)$_2$-dT$_4$-(N3CET)$_3$-dT$_{13}$-C3 | 106 |
| (dG6P)$_2$-dT$_6$-(Tmp)$_6$-dT$_8$-C3 | 107 |

[1]Single-dN6P substrates include C11-triazole-C4 linker (as in compound (3d)) between terminal hexaphosphate moiety and tag sequence.
[2]Double-dN6P substrates include doubler-linker (as in compound (3a)) between terminal hexaphosphate moiety and tag sequence.
[3]Abbreviations for tag sequences are those commonly used for oligonucleotide synthesis (see e.g., abbreviations in Table 3).

Briefly, the nanopore sequencing is carried out using an array of α-HL nanopores each conjugated to Pol6 polymerase. The α-HL-Pol6 nanopore conjugates are embedded in membranes formed over an array of individually addressable integrated circuit chips. This α-HL-Pol6 nanopore array is exposed to a DNA template and a set of the four differently tagged nucleotide substrates, either a set of the four single-dN6P substrates or the double-dN6P substrates shown in Table 8. The double-dN6P substrates are prepared using doubler-linkers according to the general method of Example 1 for preparing compound (3a), except the desired nucleotide and oligonucleotide tag are substituted. As the specific tagged nucleotide that is complementary to the DNA template is captured and bound to the Pol6 polymerase active site, the tag moiety becomes positioned in the α-HL nanopore conjugated nearby. Under the applied AC potential, the presence of the tag in the pore causes a distinctive blocking current compared to the open pore current (i.e., current with no tag in the nanopore). The sequence of blocking currents measured as the conjugated Pol6 synthesizes the DNA extension strand complementary to the template identifies the sequence of DNA template.

Nanopore Detection System:

The nanopore blocking current measurements are performed using a nanopore array microchip comprising a CMOS microchip that has an array of 128,000 silver electrodes within shallow wells (chip fabricated by Genia Technologies, Mountain View, Calif., USA). Methods for fabricating and using such nanopore array microchips can also be found in U.S. Patent Application Publication Nos. 2013/0244340 A1, US 2013/0264207 A1, and US2014/0134616 A1 each of which is hereby incorporated by reference herein. Each well in the array is manufactured using a standard CMOS process with surface modifications that allow for constant contact with biological reagents and conductive salts. Each well can support a phospholipid bilayer membrane with a nanopore-polymerase conjugate embedded therein. The electrode at each well is individually addressable by computer interface. All reagents used are introduced into a simple flow cell above the array microchip using a computer-controlled syringe pump. The chip supports analog to digital conversion and reports electrical measurements from all electrodes independently at a rate of over 1000 points per second. Nanopore blocking current measurements can be made asynchronously at each of 128K addressable nanopore-containing membranes in the array at least once every millisecond (msec) and recorded on the interfaced computer.

Formation of Lipid Bilayer on Chip:

The phospholipid bilayer membrane on the chip is prepared using 1,2-diphytanoyl-sn-glycero-3-phosphocholine (Avanti Polar Lipids). The lipid powder is dissolved in decane at 15 mM and then painted in a layer across the wells on the chip. A thinning process then is initiated by pumping air through the cis side of the array wells, thus reducing multi-lamellar lipid membranes to a single bilayer. Bilayer formation is tested using a ramping voltage from 0 to 1000 mV. A typical single bilayer would temporarily open at an applied voltage of between 300 to 500 mV.

Insertion of α-HL-Pol6 Conjugate in Membrane:

After the lipid bilayer forms on the wells of the array chip, 3 μM of the set of tagged nucleotides (from Table 8), 0.1 μM of a 6:1 α-HL-Pol6 nanopore-polymerase conjugate, 0.4 μM of the desired DNA template, all in a buffer solution of 3 mM $CaCl_2$, 20 mM HEPES, and 500 mM K-Glu, pH 8, at 20° C. is added to the cis side of the chip. The nanopore-polymerase conjugate in the mixture spontaneously inserts into the lipid bilayer. Since only $Ca^{2+}$ (and no $Mg^{2+}$ ion) is present, the ternary complex is able to form at the Pol6 active site but a tagged nucleotide is not incorporated and the 5'-phosphate-linked tag is not released.

The DNA template is the dumb-bell circular template, "HP7" which has the sequence:

(SEQ ID NO: 126)
CGATTACTTTAGTTTTCGTTTTTACTACTGACTGTCCTCCTCCTCCGTT

ATTGTAAAAACGAAAACTAAAGTAATCGCGATTACTTTAGTTTTCGTTT

TTACTACTGACTGTCCTCCTCCTCCGTTATTGTAAAAACGAAAACTAAA

GTAATCG.

Nanopore Blocking Current Measurements:

The buffer solution used as the electrolyte solution for the nanopore current blockade measurements is 500 mM potassium glutamate, pH 8, 3 mM $MgCl_2$, 20 mM HEPES, 5 mM TCEP, at 20° C. A Pt/Ag/AgCl electrode setup is used and an AC current of a −10 mV to 200 mV square waveform applied. AC current can have certain advantages for nanopore detection as it allows for the tag to be repeatedly directed into and then expelled from the nanopore thereby providing more opportunities to detection. AC current also can provide a steadier potential for a more stable current signal and less degradation of the electrodes over time.

Signals representing four distinct current blockade events are observed from the sets of four different tagged nucleotides as they are captured by the α-HL-Pol6 nanopore-polymerase conjugates primed with the DNA template. Plots of the sequence of blocking current events are recorded over time and analyzed. Generally, blocking current events that last longer than 10 ms and that reduce the open channel current from 0.8 to 0.2 indicate productive nucleotide capture coincident with polymerase incorporation of the correct base complementary to the template strand.

Results

Average values for relevant nanopore array sequencing parameters determined in experiments carried out with the two set of tagged dN6P substrates are shown in Table 9.

TABLE 9

|  | Double-dN6P-Single-Tag (20-mer length) Substrates | Single-dN6P-Single-Tag (30-mer length) Substrates |
| --- | --- | --- |
| Waiting Time | 1.1 | 2.7 |
| Transition Rate (bases/sec) | 0.3 | 0.16 |
| Dwell time (sec) | 0.62 | 0.64 |
| Heteropolymer Read Length | 254 | 119 |

As shown by the results in Table 9, the set of four differently tagged multi-nucleotide polymerase substrates exhibit significantly increased processivity and read length when used in a nanopore sequencing experiment. Additionally, plots of read length versus accuracy (in calling the sequence) show that the tagged multi-nucleotide compounds result in no loss of accuracy with the longer read length relative to the single-nucleotide-single-tag substrate compounds. Selected nanopores in the arrays are able to achieve read lengths of above 800 bp. In a typical example of a longer heteropolymer read length achievable with the tagged multi-nucleotide substrates, a read length of 531 bp heteropolymer sequence is called with the following score: 71% (375/531), 21 insertions, 133 deletions, 2 mismatches. In a typical example of a longer homopolymeric read length achievable with the tagged multi-nucleotide substrates, a read length of 770 bp homopolymer sequence is called with the following score: 53% (521/982), 212 insertions, 247 deletions, 2 mismatches.

Example 5: Improved Conditions for Nanopore Sequencing Using Tagged Multi-Nucleotides This example further illustrates how to use a set of four differently tagged multi-nucleotide compounds for nanopore sequencing and exemplifies materials and conditions that provide further improved sequencing results. As in Example 4, a set of tagged multi-nucleotides, with two nucleotides per tag attached via a doubler-linker to oligonucleotide tags of 20-mer length, are compared to a set of tagged single nucleotide compounds having a comparable set of oligonucleotide tags of 30-mer length. The two sets of tagged dN6P substrates used in the example are shown in Table 10.

TABLE 10

| Sindle-dN6P Substrate Set[1] | Tag[3] SEQ ID NO: |
| --- | --- |
| $dA6P-Cy3-dT_5-(BHEB)-dT_{24}-C3$ | 108 |
| $dC6P-Cy3-dT_{30}-C3$ | 34 |
| $dT6P-Cy3-dT_4-(N3CET)_3-dT_{23}-C3$ | 102 |
| $dG6P-dT_6-(Tmp)_6-dT_{18}-C3$ | 103 |
| Double-dN6P Substrate Set[2] |  |
| $(dA6P)_2-dT_5-(BHEB)-dT_{14}-C3$ | 109 |
| $(dC6P)_2-dT_{20}-C3$ | 105 |
| $(dT6P)_2-dT_4-(N3CET)_3-dT_{13}-C3$ | 106 |
| $(dG6P)_2-dT_6-(Tmp)_6-dT_8-C3$ | 107 |

[1]Single-dN6P substrates include C11-triazole-C4 linker (as in compound (3d)) between terminal hexaphosphate moiety and tag sequence.
[2]Double-dN6P substrates include doubler-linker (as in compound (3a)) between terminal hexaphosphate moiety and tag sequence.
[3]Abbreviations for Tag sequences are those commonly used for oligonucleotide synthesis (see e.g., abbreviations in Table 3).

The double-dN6P substrates are prepared using doubler-linkers according to the general method of Example 1 for preparing compound (3a), except the desired nucleotide and oligonucleotide tag are substituted.

The nanopore sequencing in this Example is carried out using the same materials and methods as in Example 4 except for some changes in the buffer and AC waveform conditions used during blocking current measurements. Most significantly, the concentration of K-Glu is 300 mM rather than 500 mM as in Example 3. The cis side buffer contains 300 mM K-Glu, 3 mM MgCl$_2$, 5 mM TCEP, and 10 µM of each of the tagged dN6P substrates of Table 10. The trans side buffer contains 340 mM K-Glu and 3 mM MgCl$_2$. The AC waveform is characterized as follows: voltage mode, 50 Hz, 40% duty cycle, 235 mV, 7200 S.

The DNA template is the same dumb-bell circular template, HP7 of SEQ ID NO: 126 described in Example 3.

Results

Average values for relevant nanopore array sequencing parameters determined in experiments carried out with the two set of tagged dN6P substrates are shown in Table 11.

TABLE 11

| | Double-dN6P-Single-Tag (20-mer length) Substrates | Single-dN6P-Single-Tag (30-mer length) Substrates |
|---|---|---|
| Waiting Time | 0.86 | 1.57 |
| Transition Rate (bases/sec) | 0.34 | 0.20 |
| Dwell time (sec) | 0.70 | 0.71 |
| Heteropolymer Read Length | 300 | 161 |

As shown by the results in Table 11, the set of four differently tagged multi-nucleotide polymerase substrates of Table 10 exhibit significantly increased polymerase processivity and read length when used in a nanopore sequencing experiment in the presence of 300 mM K-Glu. In a typical example of a longer heteropolymer read length achievable with the tagged multi-nucleotide substrates under the 300 mM K-Glu conditions, a read length of 2926 bp is achieved with the following score: 70% (1399/2011); procession length: 2926; 73 insertions; 529 deletions, 10 mismatches. Homopolymeric read length achievable with the tagged multi-nucleotide substrates under the 300 mm K-Glu conditions: 51% (1797/3554); procession length; 2926; 628 insertions; 1118 deletions, 11 mismatches.

Additionally, the set of four multi-tagged nucleotides show in Table 10 exhibit particularly good blocking current level separation under the 300 mM K-Glu conditions of this example. The blocking current levels (measured as Fraction of Open Current) are as follows:

(dA6P)$_2$-dT$_5$-(BHEB)-dT$_{14}$-C3=0.88+/−0.03;

(dC6P)$_2$-dT$_{20}$-C3=0.76+/−0.04;

(dT6P)$_2$-dT$_4$-(N3CE-dT)$_3$-dT$_{13}$-C3=0.62+/−0.05;

(dG6P)$_2$-dT$_6$-(Tmp)$_6$-dT$_8$-C3=0.38+/−0.08

The good separation between the blocking current levels of these tags allows for more accurate calls in nanopore sequencing.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A method for determining the sequence of a nucleic acid comprising:

(a) providing a nanopore sequencing composition comprising: a membrane, an electrode on the cis side and the trans side of the membrane, a nanopore with its pore extending through the membrane, an electrolyte solution in contact with both electrodes, an active polymerase situated adjacent to the nanopore, and a primer strand complexed with the polymerase;

(b) contacting the nanopore sequencing composition with (i) a strand of the nucleic acid; and (ii) a set of compounds each comprising a single tag covalently linked to a plurality of nucleoside-5'-oligophosphate moieties, wherein the tag is a molecular moiety selected from a polyethylene-glycol (PEG) oligomer, an oligonucleotide comprising natural and/or non-natural analog monomer units, a polypeptide comprising natural and/or non-natural analog monomer units, and an oligomeric moiety comprising a combination of any of these and is capable of producing a detectable signal, each nucleoside-5'-oligophosphate moiety is capable of being a substrate for a polymerase, and each member of the set of compounds has a different tag that produces a different detectable signal when the tag is situated in a nanopore; and (c) detecting the different detectable signals of the tags over time and correlating to each of the different tags the different compounds incorporated by the polymerase which are complementary to the nucleic acid sequence, and thereby determining the nucleic acid sequence.

2. The method of claim 1, wherein each compound of the set has a structural formula (I)

[N-P-L]$_m$-T     (I)

wherein,

N is a nucleoside;

P is an oligophosphate covalently attached to a 5'—O group of the nucleoside, wherein the oligophosphate consists of 3 to 12 phosphate groups;

L is a linker covalently attached to a terminal phosphate group of the oligophosphate;

m is from 2 to 12 and indicates the number of N-P-L moieties; and

T is the tag covalently attached the N-P-L moieties.

3. The method of claim 2, wherein m is from 2 to 6.

4. The method of claim 1, wherein each compound of the set has structural formula (II)

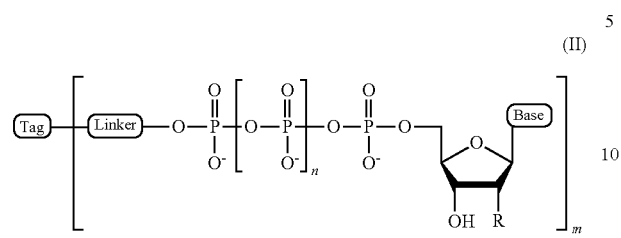

wherein,

Base is selected from adenosine, cytidine, guanosine, thymidine, and uridine;

R is selected from H and OH;

n is from 1 to 4;

Linker is a linker comprising a covalently bonded chain of 2 to 100 atoms;

m is from 2 to 12; and

Tag is the tag.

5. The method of claim 4, wherein m is from 2 to 6.

6. The method of claim 4, wherein the linker comprises a chemical group having structural formula (XVd) or (XVe):

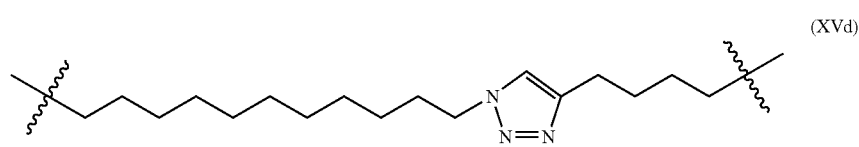

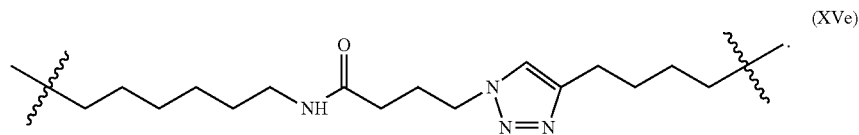

7. The method of claim 1, wherein each compound of the set has a structural formula selected from formula (IIIa), (IIIb), or (IIIc):

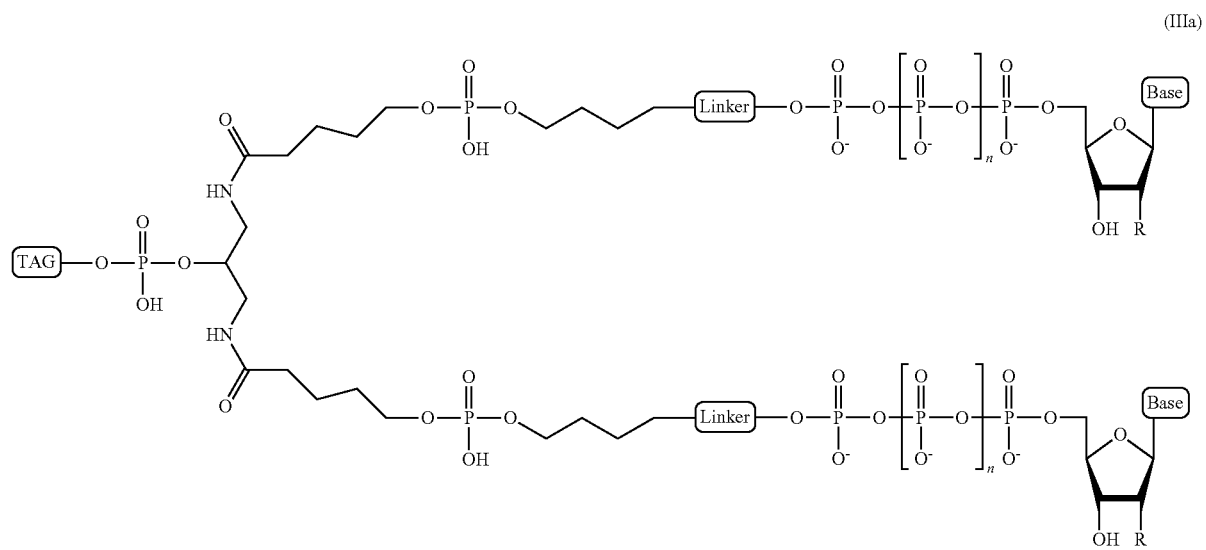

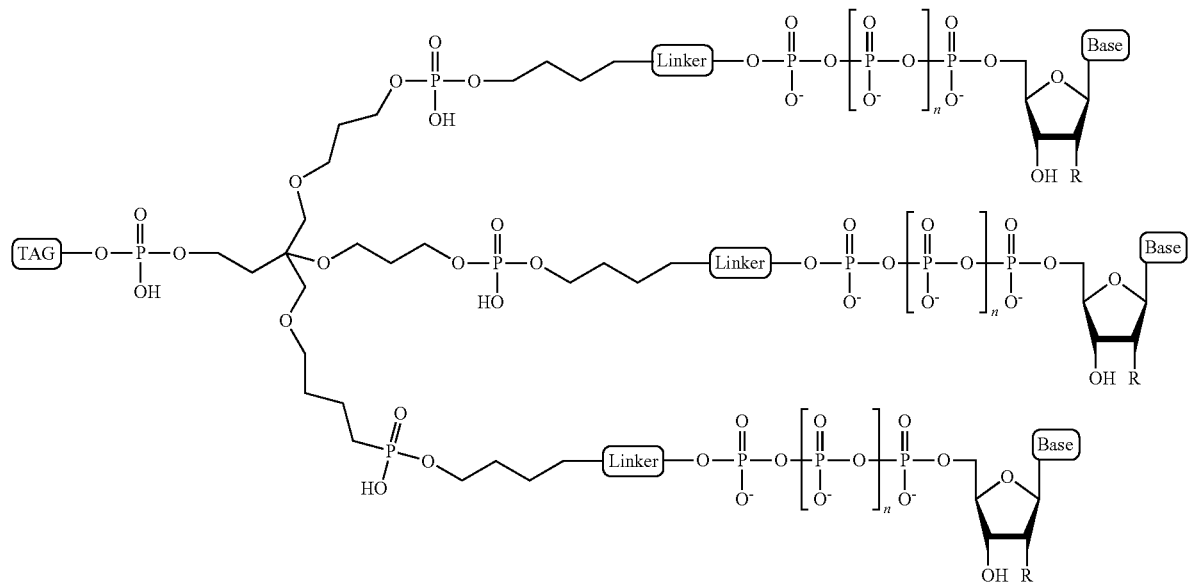
(IIIb)
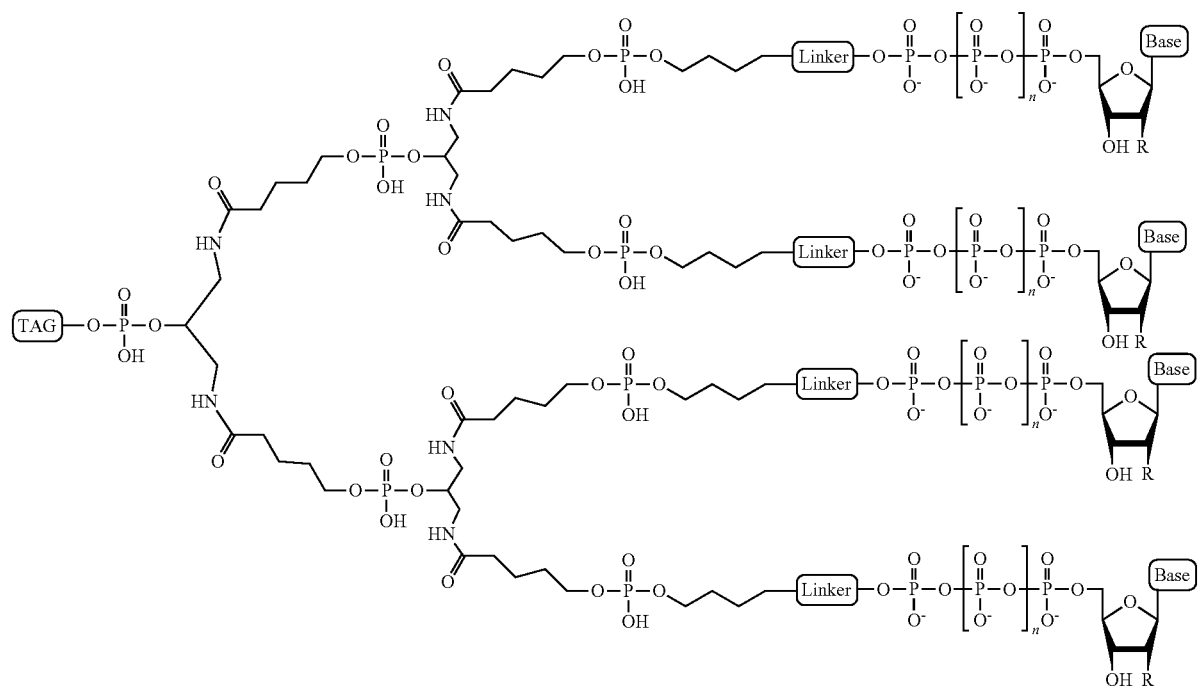
(IIIc)
wherein,
Base is selected from adenosine, cytidine, guanosine, thymidine, and uridine;
R is selected from H and OH;
n is from 1 to 4;
Linker is a linker comprising a covalently bonded chain of 2 to 100 atoms; and
Tag is the tag.

8. The method of claim 3, wherein the linker comprises a chemical group having structural formula (XVd) or (XVe):
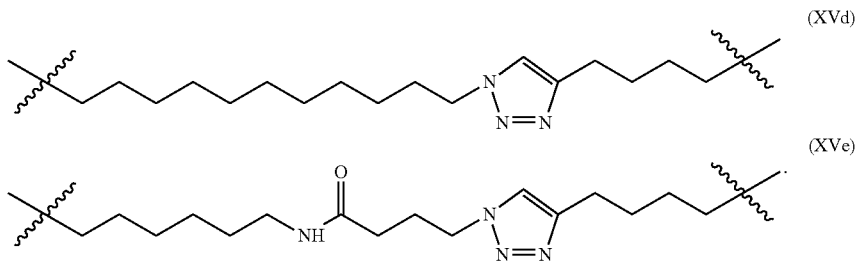
9. The method of claim 1, wherein each compound has a structural formula selected from formula (IIId), (IIIe), or (IIIf):
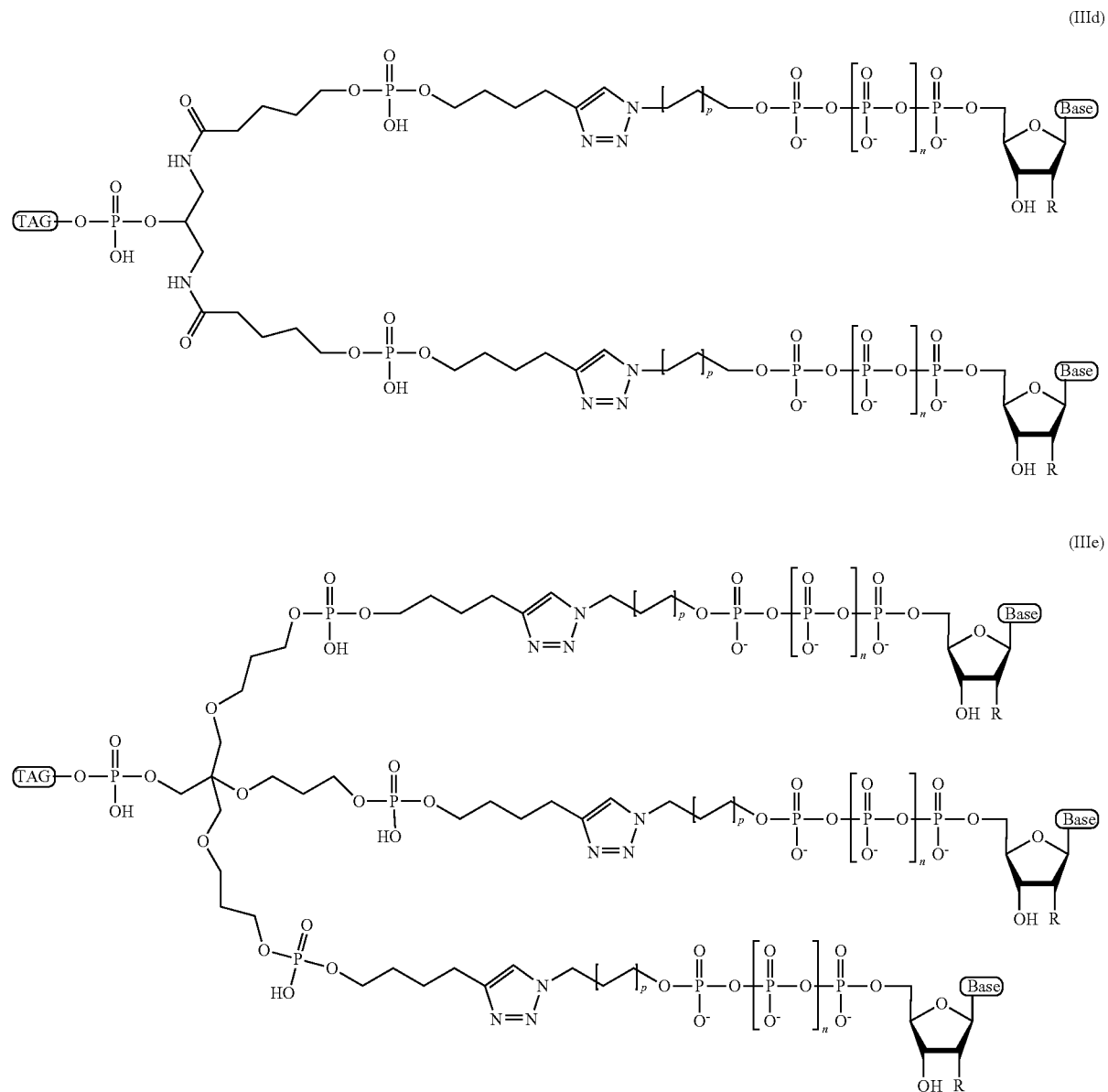

(IIIf)

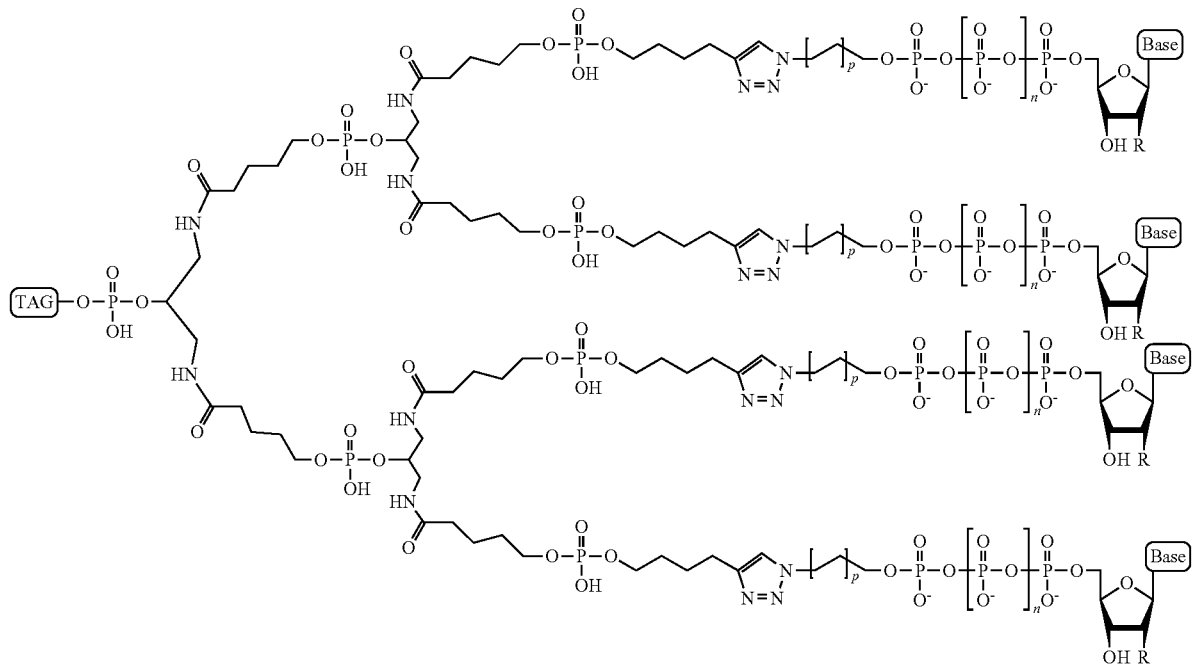

wherein,
Base is selected from adenosine, cytidine, guanosine, thymidine, and uridine;
R is selected from H and OH;
n is from 1 to 4;
p is from 2 to 10; and
Tag is the tag.

10. The method of claim 1, wherein at least one of the different tags comprises an oligonucleotide having a monomer unit length of from 15-mer to 45-mer.

11. The method of claim 1, wherein at least one of the different tags comprises an oligonucleotide having a structure selected from Table 3, 7, 8, or 10, or a sequence selected from SEQ ID NO: 1-109.

12. The method of claim 1, wherein at least one of the different tags comprises a polypeptide.

13. The method of claim 1, wherein at least one of the different tags comprises a polypeptide having a structure selected from Table 5, or a sequence selected from SEQ ID NO: 110-123.

14. The method of claim 1, wherein the linker comprises a chemical group selected from the group consisting of: ester, ether, thioether, amine, amide, imide, benzene, benzyl ether, phenol, bis-hydroxyethylbenzene, carbonate, carbamate, squarate, thiazole, thiazolidine, hydrazone, oxime, triazole, dihydropyridazine, phosphodiester, polyethylene glycol (PEG), and combinations thereof.

15. The method of claim 1, wherein the detectable signals produced by at least two compounds of the set differ by at least 10%, at least 25%, at least 50%, or at least 75%.

16. The method of claim 1, wherein the set of compounds comprises $(dA6P)_2$-$dT_5$-(BHEB)-$dT_{14}$-C3; $(dC6P)_2$-$dT_{20}$-C3; $(dT_6P)_2$-$dT_4$-(N3CE-dT)$_3$-$dT_{13}$-C3; and $(dG6P)_2$-$dT_6$-(Tmp)$_6$-$dT_8$-C3.

17. The method of claim 1, wherein the set of compounds comprises $(dA6P)_2$-$dT_4$-(idSp-dT)$_4$-$dT_8$-C3; $(dC6P)_2$-$dT_{20}$-C3; $(dT_6P)_2$-$dT_4$-(N3CE-dT)$_3$-$dT_{13l\_c}$3; and $(dG6P)_2$-$dT_6$-(Tmp)$_6$-$dT_8$-C3.

* * * * *

SEQUENCE LISTING

<160> NUMBER OF SEQ ID NOS: 126

<210> SEQ ID NO 1
<211> LENGTH: 30
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: 5'-cyanine 3-phosphate-T

<400> SEQUENCE: 1
tttttttttt tttttttttt tttttttttt                                    30

<210> SEQ ID NO 2
<211> LENGTH: 30
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: thiophosphate diester bond to following T
<220> FEATURE:
<221> NAME/KEY: misc_feature
<222> LOCATION: (3)..(3)
<223> OTHER INFORMATION: thiophosphate diester bond to following T
<220> FEATURE:
<221> NAME/KEY: misc_feature
<222> LOCATION: (5)..(5)

```
<223> OTHER INFORMATION: thiophosphate diester bond to following T
<220> FEATURE:
<221> NAME/KEY: misc_feature
<222> LOCATION: (7)..(7)
<223> OTHER INFORMATION: thiophosphate diester bond to following T
<220> FEATURE:
<221> NAME/KEY: misc_feature
<222> LOCATION: (9)..(9)
<223> OTHER INFORMATION: thiophosphate diester bond to following T
<220> FEATURE:
<221> NAME/KEY: misc_feature
<222> LOCATION: (11)..(11)
<223> OTHER INFORMATION: thiophosphate diester bond to following T
<220> FEATURE:
<221> NAME/KEY: misc_feature
<222> LOCATION: (13)..(13)
<223> OTHER INFORMATION: thiophosphate diester bond to following T
<220> FEATURE:
<221> NAME/KEY: misc_feature
<222> LOCATION: (15)..(15)
<223> OTHER INFORMATION: thiophosphate diester bond to following T
<220> FEATURE:
<221> NAME/KEY: misc_feature
<222> LOCATION: (17)..(17)
<223> OTHER INFORMATION: thiophosphate diester bond to following T
<220> FEATURE:
<221> NAME/KEY: misc_feature
<222> LOCATION: (19)..(19)
<223> OTHER INFORMATION: thiophosphate diester bond to following T
<220> FEATURE:
<221> NAME/KEY: misc_feature
<222> LOCATION: (21)..(21)
<223> OTHER INFORMATION: thiophosphate diester bond to following T
<220> FEATURE:
<221> NAME/KEY: misc_feature
<222> LOCATION: (23)..(23)
<223> OTHER INFORMATION: thiophosphate diester bond to following T
<220> FEATURE:
<221> NAME/KEY: misc_feature
<222> LOCATION: (25)..(25)
<223> OTHER INFORMATION: thiophosphate diester bond to following T
<220> FEATURE:
<221> NAME/KEY: misc_feature
<222> LOCATION: (27)..(27)
<223> OTHER INFORMATION: thiophosphate diester bond to following T
<220> FEATURE:
<221> NAME/KEY: misc_feature
<222> LOCATION: (29)..(29)
<223> OTHER INFORMATION: thiophosphate diester bond to following T

<400> SEQUENCE: 2
tttttttttt tttttttttt tttttttttt                                    30

<210> SEQ ID NO 3
<211> LENGTH: 30
<212> TYPE: DNA
<213> ORGANISM: Artificial Sequence
<220> FEATURE:
<223> OTHER INFORMATION: synthesized oligonucleotide

<400> SEQUENCE: 3
tttttttttt tttttttttt tttttttttt                                    30

<210> SEQ ID NO 4
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (7)..(14)
<223> OTHER INFORMATION: furan amidite

<400> SEQUENCE: 4
``` tttttttnnnn nnnntttttt tttttttttt                                               30

<210> SEQ ID NO 5
<211> LENGTH: 30
<212> TYPE: DNA
<213> ORGANISM: Artificial sequence
<220> FEATURE:
<223> OTHER INFORMATION: synthesized oligonucleotide
<220> FEATURE:
<221> NAME/KEY: misc_feature
<222> LOCATION: (7)..(16)
<223> OTHER INFORMATION: thiophosphate diester bond to following T

<400> SEQUENCE: 5
tttttttttt tttttttttt tttttttttt                                                30

<210> SEQ ID NO 6
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (4)..(6)
<223> OTHER INFORMATION: furan amidite

<400> SEQUENCE: 6
tttnnntttt tttttttttt tttttttttt                                                30

<210> SEQ ID NO 7
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (8)..(10)
<223> OTHER INFORMATION: furan amidite

<400> SEQUENCE: 7
tttttttnnn tttttttttt tttttttttt                                                30

<210> SEQ ID NO 8
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (11)..(13)
<223> OTHER INFORMATION: furan amidite

<400> SEQUENCE: 8
tttttttttt nnnttttttt tttttttttt                                                30

<210> SEQ ID NO 9
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (14)..(16)
<223> OTHER INFORMATION: furan amidite

```
<400> SEQUENCE: 9
tttttttttt tttnnnttttt tttttttttt                                    30

<210> SEQ ID NO 10
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (30)..(30)
<223> OTHER INFORMATION: hexanol-T

<400> SEQUENCE: 10
tttttttttt tttttttttt tttttttttt                                    30

<210> SEQ ID NO 11
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (30)..(30)
<223> OTHER INFORMATION: hexanol

<400> SEQUENCE: 11
tttttttttt tttttttttt tttttttttt                                    30

<210> SEQ ID NO 12
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (5)..(14)
<223> OTHER INFORMATION: furan amidite
<220> FEATURE:
<221> NAME/KEY: misc_feature
<222> LOCATION: (30)..(30)
<223> OTHER INFORMATION: hexanol-T

<400> SEQUENCE: 12
ttttnnnnnn nnnnttttttt tttttttttt                                    30

<210> SEQ ID NO 13
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (5)..(6)
<223> OTHER INFORMATION: nitropyrrole
<220> FEATURE:
<221> NAME/KEY: misc_feature
<222> LOCATION: (11)..(12)
<223> OTHER INFORMATION: nitropyrrole
<220> FEATURE:
<221> NAME/KEY: misc_feature
<222> LOCATION: (17)..(18)
<223> OTHER INFORMATION: nitropyrrole
```

```
<220> FEATURE:
<221> NAME/KEY: misc_feature
<222> LOCATION: (23)..(24)
<223> OTHER INFORMATION: nitropyrrole
<220> FEATURE:
<221> NAME/KEY: misc_feature
<222> LOCATION: (29)..(29)
<223> OTHER INFORMATION: nitropyrrole
<220> FEATURE:
<221> NAME/KEY: misc_feature
<222> LOCATION: (30)..(30)
<223> OTHER INFORMATION: nitropyrrole-propanol

<400> SEQUENCE: 13
ttttnntttt nnttttnntt ttnnttttnn                                30

<210> SEQ ID NO 14
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (5)..(6)
<223> OTHER INFORMATION: nebularine
<220> FEATURE:
<221> NAME/KEY: misc_feature
<222> LOCATION: (11)..(12)
<223> OTHER INFORMATION: nebularine
<220> FEATURE:
<221> NAME/KEY: misc_feature
<222> LOCATION: (17)..(18)
<223> OTHER INFORMATION: nebularine
<220> FEATURE:
<221> NAME/KEY: misc_feature
<222> LOCATION: (23)..(24)
<223> OTHER INFORMATION: nebularine
<220> FEATURE:
<221> NAME/KEY: misc_feature
<222> LOCATION: (29)..(29)
<223> OTHER INFORMATION: nebularine
<220> FEATURE:
<221> NAME/KEY: misc_feature
<222> LOCATION: (30)..(30)
<223> OTHER INFORMATION: nebularine-propanol

<400> SEQUENCE: 14
ttttnntttt nnttttnntt ttnnttttnn                                30

<210> SEQ ID NO 15
<211> LENGTH: 27
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (5)..(5)
<223> OTHER INFORMATION: 18-atom PEG
<220> FEATURE:
<221> NAME/KEY: misc_feature
<222> LOCATION: (27)..(27)
<223> OTHER INFORMATION: T-propanol

<400> SEQUENCE: 15
ttttnttttt tttttttttt ttttttt                                   27

<210> SEQ ID NO 16
<211> LENGTH: 25
<212> TYPE: DNA
<213> ORGANISM: Artificial Sequence
<220> FEATURE:
```

-continued

```
<223> OTHER INFORMATION: synthesized oligonucleotide
<220> FEATURE:
<221> NAME/KEY: misc_feature
<222> LOCATION: (5)..(6)
<223> OTHER INFORMATION: 18-atom PEG-phosphate
<220> FEATURE:
<221> NAME/KEY: misc_feature
<222> LOCATION: (25)..(25)
<223> OTHER INFORMATION: T-propanol
<220> FEATURE:
<221> NAME/KEY: misc_feature
<222> LOCATION: (28)..(28)
<223> OTHER INFORMATION: propanol-T

<400> SEQUENCE: 16
ttttnntttt tttttttttt ttttt                                        25

<210> SEQ ID NO 17
<211> LENGTH: 28
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (5)..(6)
<223> OTHER INFORMATION: 9-atom PEG-phosphate
<220> FEATURE:
<221> NAME/KEY: misc_feature
<222> LOCATION: (28)..(28)
<223> OTHER INFORMATION: T-propanol

<400> SEQUENCE: 17
ttttnntttt tttttttttt ttttttt                                      28

<210> SEQ ID NO 18
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (7)..(12)
<223> OTHER INFORMATION: heptylamine amidite
<220> FEATURE:
<221> NAME/KEY: misc_feature
<222> LOCATION: (30)..(30)
<223> OTHER INFORMATION: T-propanol

<400> SEQUENCE: 18
ttttttnnnn nntttttttt tttttttttt                                   30

<210> SEQ ID NO 19
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (7)..(12)
<223> OTHER INFORMATION: pyrrolidine amidite
<220> FEATURE:
<221> NAME/KEY: misc_feature
<222> LOCATION: (30)..(30)
<223> OTHER INFORMATION: T-propanol

<400> SEQUENCE: 19
ttttttnnnn nntttttttt tttttttttt                                   30
```

```
<210> SEQ ID NO 20
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (7)..(12)
<223> OTHER INFORMATION: aminoethyl dT amidite
<220> FEATURE:
<221> NAME/KEY: misc_feature
<222> LOCATION: (30)..(30)
<223> OTHER INFORMATION: T-propanol

<400> SEQUENCE: 20
ttttttnnnn nntttttttt tttttttttt                                30

<210> SEQ ID NO 21
<211> LENGTH: 27
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (5)..(5)
<223> OTHER INFORMATION: spermine
<220> FEATURE:
<221> NAME/KEY: misc_feature
<222> LOCATION: (27)..(27)
<223> OTHER INFORMATION: T-propanol

<400> SEQUENCE: 21
ttttnttttt tttttttttt ttttttt                                   27

<210> SEQ ID NO 22
<211> LENGTH: 27
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (5)..(5)
<223> OTHER INFORMATION: spermine
<220> FEATURE:
<221> NAME/KEY: misc_feature
<222> LOCATION: (6)..(8)
<223> OTHER INFORMATION: furan amidite
<220> FEATURE:
<221> NAME/KEY: misc_feature
<222> LOCATION: (27)..(27)
<223> OTHER INFORMATION: T-propanol

<400> SEQUENCE: 22
ttttnnnntt tttttttttt ttttttt                                   27

<210> SEQ ID NO 23
<211> LENGTH: 27
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (5)..(5)
<223> OTHER INFORMATION: spermine
<220> FEATURE:
<221> NAME/KEY: misc_feature
<222> LOCATION: (6)..(6)
<223> OTHER INFORMATION: fluorescein dT amidite
<220> FEATURE:
```

-continued

```
<221> NAME/KEY: misc_feature
<222> LOCATION: (27)..(27)
<223> OTHER INFORMATION: T-propanol

<400> SEQUENCE: 23
ttttnntttt tttttttttt ttttttt                                           27

<210> SEQ ID NO 24
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (30)..(30)
<223> OTHER INFORMATION: T-propanol

<400> SEQUENCE: 24
tttttttttt tttttttttt tttttttttt                                        30

<210> SEQ ID NO 25
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3.5-T
<220> FEATURE:
<221> NAME/KEY: misc_feature
<222> LOCATION: (30)..(30)
<223> OTHER INFORMATION: T-propanol

<400> SEQUENCE: 25
tttttttttt tttttttttt tttttttttt                                        30

<210> SEQ ID NO 26
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-cyanine-3-phosphate-T
<220> FEATURE:
<221> NAME/KEY: misc_feature
<222> LOCATION: (30)..(30)
<223> OTHER INFORMATION: T-propanol

<400> SEQUENCE: 26
tttttttttt tttttttttt tttttttttt                                        30

<210> SEQ ID NO 27
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (7)..(7)
<223> OTHER INFORMATION: cyanine 3.5-phosphate
<220> FEATURE:
<221> NAME/KEY: misc_feature
<222> LOCATION: (30)..(30)
<223> OTHER INFORMATION: T-propanol
```

```
<400> SEQUENCE: 27
tttttntttt tttttttttt tttttttttt                              30

<210> SEQ ID NO 28
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (11)..(11)
<223> OTHER INFORMATION: cyanine 3-phosphate
<220> FEATURE:
<221> NAME/KEY: misc_feature
<222> LOCATION: (30)..(30)
<223> OTHER INFORMATION: T-propanol

<400> SEQUENCE: 28
tttttttttt ntttttttttt tttttttttt                             30

<210> SEQ ID NO 29
<211> LENGTH: 45
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (45)..(45)
<223> OTHER INFORMATION: T-propanol

<400> SEQUENCE: 29
ttttcggcgc gtaagcgccg tttttttttt tttttttttt ttttt             45

<210> SEQ ID NO 30
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (7)..(14)
<223> OTHER INFORMATION: furan amidite
<220> FEATURE:
<221> NAME/KEY: misc_feature
<222> LOCATION: (30)..(30)
<223> OTHER INFORMATION: T-propanol

<400> SEQUENCE: 30 tttttnnnn nnnntttttt tttttttttt                               30

<210> SEQ ID NO 31
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (1)..(1)
<223> OTHER INFORMATION: thiophosphate diester bond to following T
<220> FEATURE:
<221> NAME/KEY: misc_feature
<222> LOCATION: (3)..(3)
```

-continued

```
<223> OTHER INFORMATION: thiophosphate diester bond to following T
<220> FEATURE:
<221> NAME/KEY: misc_feature
<222> LOCATION: (5)..(5)
<223> OTHER INFORMATION: thiophosphate diester bond to following T
<220> FEATURE:
<221> NAME/KEY: misc_feature
<222> LOCATION: (7)..(7)
<223> OTHER INFORMATION: thiophosphate diester bond to following T
<220> FEATURE:
<221> NAME/KEY: misc_feature
<222> LOCATION: (9)..(9)
<223> OTHER INFORMATION: thiophosphate diester bond to following T
<220> FEATURE:
<221> NAME/KEY: misc_feature
<222> LOCATION: (11)..(11)
<223> OTHER INFORMATION: thiophosphate diester bond to following T
<220> FEATURE:
<221> NAME/KEY: misc_feature
<222> LOCATION: (13)..(13)
<223> OTHER INFORMATION: thiophosphate diester bond to following T
<220> FEATURE:
<221> NAME/KEY: misc_feature
<222> LOCATION: (15)..(15)
<223> OTHER INFORMATION: thiophosphate diester bond to following T
<220> FEATURE:
<221> NAME/KEY: misc_feature
<222> LOCATION: (17)..(17)
<223> OTHER INFORMATION: thiophosphate diester bond to following T
<220> FEATURE:
<221> NAME/KEY: misc_feature
<222> LOCATION: (19)..(19)
<223> OTHER INFORMATION: thiophosphate diester bond to following T
<220> FEATURE:
<221> NAME/KEY: misc_feature
<222> LOCATION: (21)..(21)
<223> OTHER INFORMATION: thiophosphate diester bond to following T
<220> FEATURE:
<221> NAME/KEY: misc_feature
<222> LOCATION: (23)..(23)
<223> OTHER INFORMATION: thiophosphate diester bond to following T
<220> FEATURE:
<221> NAME/KEY: misc_feature
<222> LOCATION: (25)..(25)
<223> OTHER INFORMATION: thiophosphate diester bond to following T
<220> FEATURE:
<221> NAME/KEY: misc_feature
<222> LOCATION: (27)..(27)
<223> OTHER INFORMATION: thiophosphate diester bond to following T
<220> FEATURE:
<221> NAME/KEY: misc_feature
<222> LOCATION: (29)..(29)
<223> OTHER INFORMATION: thiophosphate diester bond to following T
<220> FEATURE:
<221> NAME/KEY: misc_feature
<222> LOCATION: (30)..(30)
<223> OTHER INFORMATION: T-propanol

<400> SEQUENCE: 31
tttttttttt tttttttttt tttttttttt                                    30

<210> SEQ ID NO 32
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(29)
<223> OTHER INFORMATION: thiophosphate diester bond to following T

<400> SEQUENCE: 32
tttttttttt tttttttttt tttttttttt                                    30
```

```
<210> SEQ ID NO 33
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (1)..(29)
<223> OTHER INFORMATION: thiophosphate diester bond to next T

<400> SEQUENCE: 33
tttttttttt tttttttttt tttttttttt                                    30

<210> SEQ ID NO 34
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (30)..(30)
<223> OTHER INFORMATION: T-propanol

<400> SEQUENCE: 34
tttttttttt tttttttttt tttttttttt                                    30

<210> SEQ ID NO 35
<211> LENGTH: 15
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (15)..(15)
<223> OTHER INFORMATION: T-propanol

<400> SEQUENCE: 35
tttttttttt ttttt                                                    15

<210> SEQ ID NO 36
<211> LENGTH: 20
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (20)..(20)
<223> OTHER INFORMATION: T-propanol

<400> SEQUENCE: 36
tttttttttt tttttttttt                                               20
```

```
<210> SEQ ID NO 37
<211> LENGTH: 25
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (25)..(25)
<223> OTHER INFORMATION: T-propanol

<400> SEQUENCE: 37
tttttttttt tttttttttt ttttt                                     25

<210> SEQ ID NO 38
<211> LENGTH: 25
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3- phosphate-T
<220> FEATURE:
<221> NAME/KEY: misc_feature
<222> LOCATION: (3)..(3)
<223> OTHER INFORMATION: 18-atom PEG-phosphate
<220> FEATURE:
<221> NAME/KEY: misc_feature
<222> LOCATION: (25)..(25)
<223> OTHER INFORMATION: T-propanol

<400> SEQUENCE: 38 ttntttttttt tttttttttt ttttt                                    25

<210> SEQ ID NO 39
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (5)..(12)
<223> OTHER INFORMATION: furan amidite
<220> FEATURE:
<221> NAME/KEY: misc_feature
<222> LOCATION: (30)..(30)
<223> OTHER INFORMATION: T-propanol

<400> SEQUENCE: 39
ttttnnnnnn nntttttttt tttttttttt                                30

<210> SEQ ID NO 40
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (7)..(12)
<223> OTHER INFORMATION: aminoethyl dT amidite
```

-continued

```
<220> FEATURE:
<221> NAME/KEY: misc_feature
<222> LOCATION: (30)..(30)
<223> OTHER INFORMATION: T-propanol

<400> SEQUENCE: 40 tttttnnnn ntttttttt tttttttttt                                        30

<210> SEQ ID NO 41
<211> LENGTH: 28
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (5)..(5)
<223> OTHER INFORMATION: 9 atom PEG-phosphate
<220> FEATURE:
<221> NAME/KEY: misc_feature
<222> LOCATION: (25)..(25)
<223> OTHER INFORMATION: T-propanol

<400> SEQUENCE: 41
ttttnttttt tttttttttt ttttttt                                         28

<210> SEQ ID NO 42
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (2)..(4)
<223> OTHER INFORMATION: furan amidite
<220> FEATURE:
<221> NAME/KEY: misc_feature
<222> LOCATION: (30)..(30)
<223> OTHER INFORMATION: T-propanol

<400> SEQUENCE: 42
tnnntttttt tttttttttt tttttttttt                                      30

<210> SEQ ID NO 43
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (5)..(7)
<223> OTHER INFORMATION: furan amidite
<220> FEATURE:
<221> NAME/KEY: misc_feature
<222> LOCATION: (30)..(30)
<223> OTHER INFORMATION: T-propanol

<400> SEQUENCE: 43
```
ttttnnnttt tttttttttt tttttttttt                30

<210> SEQ ID NO 44
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (8)..(10)
<223> OTHER INFORMATION: furan amidite
<220> FEATURE:
<221> NAME/KEY: misc_feature
<222> LOCATION: (30)..(30)
<223> OTHER INFORMATION: T-propanol

<400> SEQUENCE: 44
tttttttnnn tttttttttt tttttttttt                30

<210> SEQ ID NO 45
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (11)..(13)
<223> OTHER INFORMATION: furan amidite
<220> FEATURE:
<221> NAME/KEY: misc_feature
<222> LOCATION: (30)..(30)
<223> OTHER INFORMATION: T-propanol

<400> SEQUENCE: 45
tttttttttt nnntttttttt tttttttttt                30

<210> SEQ ID NO 46
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (5)..(7)
<223> OTHER INFORMATION: fluorescein dT amidite
<220> FEATURE:
<221> NAME/KEY: misc_feature
<222> LOCATION: (30)..(30)
<223> OTHER INFORMATION: T-propanol

<400> SEQUENCE: 46
ttttnnnttt tttttttttt tttttttttt                30

<210> SEQ ID NO 47
<211> LENGTH: 30
<212> TYPE: DNA
<213> ORGANISM: Artificial Sequence

```
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (5)..(5)
<223> OTHER INFORMATION: fluorescein-dT-amidite
<220> FEATURE:
<221> NAME/KEY: misc_feature
<222> LOCATION: (7)..(7)
<223> OTHER INFORMATION: fluorescein-dT-amidite
<220> FEATURE:
<221> NAME/KEY: misc_feature
<222> LOCATION: (30)..(30)
<223> OTHER INFORMATION: T-propanol

<400> SEQUENCE: 47
ttttntnttt tttttttttt tttttttttt                                       30

<210> SEQ ID NO 48
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (30)..(30)
<223> OTHER INFORMATION: T-cyanine 3-phosphate-propanol

<400> SEQUENCE: 48
tttttttttt tttttttttt tttttttttt                                       30

<210> SEQ ID NO 49
<211> LENGTH: 29
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (9)..(9)
<223> OTHER INFORMATION: spermine
<220> FEATURE:
<221> NAME/KEY: misc_feature
<222> LOCATION: (29)..(29)
<223> OTHER INFORMATION: T-propanol

<400> SEQUENCE: 49 tttttttnt tttttttttt ttttttttt                                         29

<210> SEQ ID NO 50
<211> LENGTH: 44
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (44)..(44)
<223> OTHER INFORMATION: T-propanol

<400> SEQUENCE: 50
ttttggttgg tgtggttggt tttttttttt tttttttttt tttt                       44
```

<210> SEQ ID NO 51
<211> LENGTH: 57
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (57)..(57)
<223> OTHER INFORMATION: T-propanol

<400> SEQUENCE: 51
ttttccggcg cggcgcgtaa gcgccgcgcc ggttttttt tttttttttt tttttttt      57

<210> SEQ ID NO 52
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (6)..(8)
<223> OTHER INFORMATION: furan amidite
<220> FEATURE:
<221> NAME/KEY: misc_feature
<222> LOCATION: (30)..(30)
<223> OTHER INFORMATION: T-propanol

<400> SEQUENCE: 52
tttttnnntt tttttttttt tttttttttt      30

<210> SEQ ID NO 53
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (7)..(9)
<223> OTHER INFORMATION: furan amidite
<220> FEATURE:
<221> NAME/KEY: misc_feature
<222> LOCATION: (30)..(30)
<223> OTHER INFORMATION: T-propanol

<400> SEQUENCE: 53 tttttnnnt tttttttttt tttttttttt      30

<210> SEQ ID NO 54
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T -continued

```
<220> FEATURE:
<221> NAME/KEY: misc_feature
<222> LOCATION: (5)..(8)
<223> OTHER INFORMATION: furan amidite
<220> FEATURE:
<221> NAME/KEY: misc_feature
<222> LOCATION: (30)..(30)
<223> OTHER INFORMATION: T-propanol

<400> SEQUENCE: 54
ttttnnnntt tttttttttt tttttttttt                                           30

<210> SEQ ID NO 55
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (5)..(9)
<223> OTHER INFORMATION: furan amidite
<220> FEATURE:
<221> NAME/KEY: misc_feature
<222> LOCATION: (30)..(30)
<223> OTHER INFORMATION: T-propanol

<400> SEQUENCE: 55
ttttnnnnnt tttttttttt tttttttttt                                           30

<210> SEQ ID NO 56
<211> LENGTH: 29
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (6)..(6)
<223> OTHER INFORMATION: dodecyl amidite-phosphate
<220> FEATURE:
<221> NAME/KEY: misc_feature
<222> LOCATION: (29)..(29)
<223> OTHER INFORMATION: T-propanol
<220> FEATURE:
<221> NAME/KEY: misc_feature
<222> LOCATION: (30)..(30)
<223> OTHER INFORMATION: T-propanol

<400> SEQUENCE: 56
tttttntttt tttttttttt ttttttttt                                            29

<210> SEQ ID NO 57
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (5)..(6)
```

-continued

```
<223> OTHER INFORMATION: hexyl amidite
<220> FEATURE:
<221> NAME/KEY: misc_feature
<222> LOCATION: (30)..(30)
<223> OTHER INFORMATION: T-propanol

<400> SEQUENCE: 57
ttttnntttt tttttttttt tttttttttt                                              30

<210> SEQ ID NO 58
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (5)..(7)
<223> OTHER INFORMATION: propyl amidite
<220> FEATURE:
<221> NAME/KEY: misc_feature
<222> LOCATION: (30)..(30)
<223> OTHER INFORMATION: T-propanol

<400> SEQUENCE: 58
ttttnnnttt tttttttttt tttttttttt                                              30

<210> SEQ ID NO 59
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (3)..(10)
<223> OTHER INFORMATION: furan amidite
<220> FEATURE:
<221> NAME/KEY: misc_feature
<222> LOCATION: (30)..(30)
<223> OTHER INFORMATION: T-propanol

<400> SEQUENCE: 59
ttnnnnnnnn tttttttttt tttttttttt                                              30

<210> SEQ ID NO 60
<211> LENGTH: 34
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (31)..(33)
<223> OTHER INFORMATION: propyl amidite
<220> FEATURE:
<221> NAME/KEY: misc_feature
<222> LOCATION: (34)..(34)
<223> OTHER INFORMATION: propyl amidite-propanol

<400> SEQUENCE: 60
```
tttttttttt tttttttttt tttttttttt nnnn                    34

<210> SEQ ID NO 61
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (30)..(30)
<223> OTHER INFORMATION: T-phosphate

<400> SEQUENCE: 61
tttttttttt tttttttttt tttttttttt                         30

<210> SEQ ID NO 62
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (30)..(30)
<223> OTHER INFORMATION: T-propylamine

<400> SEQUENCE: 62
tttttttttt tttttttttt tttttttttt                         30

<210> SEQ ID NO 63
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: phosphate-T
<220> FEATURE:
<221> NAME/KEY: misc_feature
<222> LOCATION: (30)..(30)
<223> OTHER INFORMATION: T-cyanine 3-phosphate-propylamine-phosphate-
      proparyl-propionamide

<400> SEQUENCE: 63
tttttttttt tttttttttt tttttttttt                         30

<210> SEQ ID NO 64
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: phosphate-T
<220> FEATURE:
<221> NAME/KEY: misc_feature
<222> LOCATION: (25)..(27)
<223> OTHER INFORMATION: furan amidite

```
<220> FEATURE:
<221> NAME/KEY: misc_feature
<222> LOCATION: (30)..(30)
<223> OTHER INFORMATION: T-cyanine 3-phosphate-propylamine-phosphate-
      proparyl-propionamide

<400> SEQUENCE: 64 ttttttttttt tttttttttt ttttnnnttt                                       30

<210> SEQ ID NO 65
<211> LENGTH: 45
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (45)..(45)
<223> OTHER INFORMATION: T-propanol

<400> SEQUENCE: 65
ttttcggcgc gtaagcgccg tttttttttt tttttttttt ttttt                       45

<210> SEQ ID NO 66
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-C
<220> FEATURE:
<221> NAME/KEY: misc_feature
<222> LOCATION: (30)..(30)
<223> OTHER INFORMATION: C-propanol

<400> SEQUENCE: 66
cccccccccc cccccccccc cccccccccc                                        30

<210> SEQ ID NO 67
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (5)..(10)
<223> OTHER INFORMATION: 2'-deoxyinosine
<220> FEATURE:
<221> NAME/KEY: misc_feature
<222> LOCATION: (30)..(30)
<223> OTHER INFORMATION: T-propanol

<400> SEQUENCE: 67
ttttnnnnnn tttttttttt tttttttttt                                        30

<210> SEQ ID NO 68
<211> LENGTH: 30
<212> TYPE: DNA
<213> ORGANISM: Artificial Sequence
```

```
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (5)..(10)
<223> OTHER INFORMATION: 5-nitroindole
<220> FEATURE:
<221> NAME/KEY: misc_feature
<222> LOCATION: (30)..(30)
<223> OTHER INFORMATION: T-propanol

<400> SEQUENCE: 68
ttttnnnnnn tttttttttt tttttttttt                                        30

<210> SEQ ID NO 69
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (30)..(30)
<223> OTHER INFORMATION: T-propanol

<400> SEQUENCE: 69
tttcccccct tttttttttt tttttttttt                                        30

<210> SEQ ID NO 70
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (5)..(10)
<223> OTHER INFORMATION: 5-iodo deoxyuridine
<220> FEATURE:
<221> NAME/KEY: misc_feature
<222> LOCATION: (30)..(30)
<223> OTHER INFORMATION: T-propanol

<400> SEQUENCE: 70
ttttnnnnnn tttttttttt tttttttttt                                        30

<210> SEQ ID NO 71
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (5)..(10)
<223> OTHER INFORMATION: 5-pyrene-deoxyuridine
<220> FEATURE:
```

```
<221> NAME/KEY: misc_feature
<222> LOCATION: (30)..(30)
<223> OTHER INFORMATION: T-propanol

<400> SEQUENCE: 71
ttttnnnnnn tttttttttt tttttttttt                                      30

<210> SEQ ID NO 72
<211> LENGTH: 29
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (3)..(30)
<223> OTHER INFORMATION: T-propanol
<220> FEATURE:
<221> NAME/KEY: misc_feature
<222> LOCATION: (5)..(5)
<223> OTHER INFORMATION: furan amidite
<220> FEATURE:
<221> NAME/KEY: misc_feature
<222> LOCATION: (7)..(7)
<223> OTHER INFORMATION: furan amidite
<220> FEATURE:
<221> NAME/KEY: misc_feature
<222> LOCATION: (9)..(9)
<223> OTHER INFORMATION: furan amidite
<220> FEATURE:
<221> NAME/KEY: misc_feature
<222> LOCATION: (11)..(11)
<223> OTHER INFORMATION: furan amidite

<400> SEQUENCE: 72
ttttntntnt nttttttttt tttttttttt                                      29

<210> SEQ ID NO 73
<211> LENGTH: 29
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (6)..(6)
<223> OTHER INFORMATION: furan amidite
<220> FEATURE:
<221> NAME/KEY: misc_feature
<222> LOCATION: (8)..(8)
<223> OTHER INFORMATION: furan amidite
<220> FEATURE:
<221> NAME/KEY: misc_feature
<222> LOCATION: (10)..(10)
<223> OTHER INFORMATION: furan amidite
<220> FEATURE:
<221> NAME/KEY: misc_feature
<222> LOCATION: (12)..(12)
<223> OTHER INFORMATION: furan amidite
<220> FEATURE:
<221> NAME/KEY: misc_feature
<222> LOCATION: (30)..(30)
<223> OTHER INFORMATION: T-propanol

<400> SEQUENCE: 73
tttttntntn tnttttttttt tttttttttt                                     29
```

```
<210> SEQ ID NO 74
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (5)..(10)
<223> OTHER INFORMATION: propanol
<220> FEATURE:
<221> NAME/KEY: misc_feature
<222> LOCATION: (30)..(30)
<223> OTHER INFORMATION: T-propanol

<400> SEQUENCE: 74
ttttnnnnnn tttttttttt tttttttttt                                    30

<210> SEQ ID NO 75
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-L isomer of T
<220> FEATURE:
<221> NAME/KEY: misc_feature
<222> LOCATION: (2)..(29)
<223> OTHER INFORMATION: L isomer of T
<220> FEATURE:
<221> NAME/KEY: misc_feature
<222> LOCATION: (30)..(30)
<223> OTHER INFORMATION: L isomer of T-propanol

<400> SEQUENCE: 75
tttttttttt tttttttttt tttttttttt                                    30

<210> SEQ ID NO 76
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-L isomer of T
<220> FEATURE:
<221> NAME/KEY: misc_feature
<222> LOCATION: (2)..(4)
<223> OTHER INFORMATION: L isomer of T
<220> FEATURE:
<221> NAME/KEY: misc_feature
<222> LOCATION: (5)..(7)
<223> OTHER INFORMATION: furan amidite
<220> FEATURE:
<221> NAME/KEY: misc_feature
<222> LOCATION: (8)..(29)
<223> OTHER INFORMATION: L isomer of T
<220> FEATURE:
<221> NAME/KEY: misc_feature
<222> LOCATION: (30)..(30)
<223> OTHER INFORMATION: L isomer of T-propanol

<400> SEQUENCE: 76
```
ttttnnnttt tttttttttt tttttttttt                                                  30

<210> SEQ ID NO 77
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-L isomer of T
<220> FEATURE:
<221> NAME/KEY: misc_feature
<222> LOCATION: (2)..(4)
<223> OTHER INFORMATION: L isomer of T
<220> FEATURE:
<221> NAME/KEY: misc_feature
<222> LOCATION: (5)..(12)
<223> OTHER INFORMATION: furan amidite
<220> FEATURE:
<221> NAME/KEY: misc_feature
<222> LOCATION: (13)..(29)
<223> OTHER INFORMATION: L isomer of T
<220> FEATURE:
<221> NAME/KEY: misc_feature
<222> LOCATION: (30)..(30)
<223> OTHER INFORMATION: L isomer of T-propanol

<400> SEQUENCE: 77
ttttnnnnnn nnttttttttt tttttttttt                                                 30

<210> SEQ ID NO 78
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-L isomer of T
<220> FEATURE:
<221> NAME/KEY: misc_feature
<222> LOCATION: (2)..(4)
<223> OTHER INFORMATION: L isomer of T
<220> FEATURE:
<221> NAME/KEY: misc_feature
<222> LOCATION: (5)..(10)
<223> OTHER INFORMATION: 2'-deoxy I
<220> FEATURE:
<221> NAME/KEY: misc_feature
<222> LOCATION: (11)..(29)
<223> OTHER INFORMATION: L isomer of T
<220> FEATURE:
<221> NAME/KEY: misc_feature
<222> LOCATION: (30)..(30)
<223> OTHER INFORMATION: L isomer of T-propanol

<400> SEQUENCE: 78
ttttnnnnnn tttttttttt tttttttttt                                                  30

<210> SEQ ID NO 79
<211> LENGTH: 45
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature

```
<222> LOCATION: (45)..(54)
<223> OTHER INFORMATION: T-propanol

<400> SEQUENCE: 79
ttttgggtgg gtgggtgggt tttttttttt tttttttttt ttttt                45

<210> SEQ ID NO 80
<211> LENGTH: 46
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (46)..(46)
<223> OTHER INFORMATION: T-propanol

<400> SEQUENCE: 80
ttttgggtgg gttgggtggg tttttttttt tttttttttt tttttt               46

<210> SEQ ID NO 81
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (5)..(6)
<223> OTHER INFORMATION: dodecyl amidite
<220> FEATURE:
<221> NAME/KEY: misc_feature
<222> LOCATION: (30)..(30)
<223> OTHER INFORMATION: T-propanol

<400> SEQUENCE: 81
ttttnntttt tttttttttt tttttttttt                                 30

<210> SEQ ID NO 82
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (4)..(6)
<223> OTHER INFORMATION: dodecyl amidite
<220> FEATURE:
<221> NAME/KEY: misc_feature
<222> LOCATION: (30)..(30)
<223> OTHER INFORMATION: T-propanol

<400> SEQUENCE: 82
tttnnntttt tttttttttt tttttttttt                                 30

<210> SEQ ID NO 83
<211> LENGTH: 33
<212> TYPE: DNA
```

<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (5)..(8)
<223> OTHER INFORMATION: hexyl amidite
<220> FEATURE:
<221> NAME/KEY: misc_feature
<222> LOCATION: (33)..(33)
<223> OTHER INFORMATION: T-propanol

<400> SEQUENCE: 83
ttttnnnntt tttttttttt tttttttttt ttt         33

<210> SEQ ID NO 84
<211> LENGTH: 32
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (5)..(9)
<223> OTHER INFORMATION: hexyl amidite
<220> FEATURE:
<221> NAME/KEY: misc_feature
<222> LOCATION: (32)..(32)
<223> OTHER INFORMATION: T-propanol

<400> SEQUENCE: 84
ttttnnnnnt tttttttttt tttttttttt tt          32

<210> SEQ ID NO 85
<211> LENGTH: 33
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (6)..(9)
<223> OTHER INFORMATION: hexyl amidite
<220> FEATURE:
<221> NAME/KEY: misc_feature
<222> LOCATION: (33)..(33)
<223> OTHER INFORMATION: T-propanol

<400> SEQUENCE: 85
tttttnnnnt tttttttttt tttttttttt ttt         33

<210> SEQ ID NO 86
<211> LENGTH: 32
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T

```
<220> FEATURE:
<221> NAME/KEY: misc_feature
<222> LOCATION: (3)..(7)
<223> OTHER INFORMATION: hexyl amidite
<220> FEATURE:
<221> NAME/KEY: misc_feature
<222> LOCATION: (32)..(32)
<223> OTHER INFORMATION: T-propanol

<400> SEQUENCE: 86
ttnnnnnttt tttttttttt tttttttttt tt                                32

<210> SEQ ID NO 87
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (5)..(5)
<223> OTHER INFORMATION: spermine
<220> FEATURE:
<221> NAME/KEY: misc_feature
<222> LOCATION: (30)..(30)
<223> OTHER INFORMATION: T-propanol

<400> SEQUENCE: 87
ttttnttttt tttttttttt tttttttttt                                   30

<210> SEQ ID NO 88
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (3)..(3)
<223> OTHER INFORMATION: spermine
<220> FEATURE:
<221> NAME/KEY: misc_feature
<222> LOCATION: (30)..(30)
<223> OTHER INFORMATION: T-propanol

<400> SEQUENCE: 88
ttnttttttt tttttttttt tttttttttt                                   30

<210> SEQ ID NO 89
<211> LENGTH: 30
<212> TYPE: DNA
<213> ORGANISM: Artificial sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (3)..(4)
<223> OTHER INFORMATION: spermine
<220> FEATURE:
<221> NAME/KEY: misc_feature
<222> LOCATION: (30)..(30)
```

<223> OTHER INFORMATION: T-propanol

<400> SEQUENCE: 89 ttnnttttttt tttttttttt tttttttttt                                30

<210> SEQ ID NO 90
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (5)..(5)
<223> OTHER INFORMATION: 5-pyrene-deoxyuridine
<220> FEATURE:
<221> NAME/KEY: misc_feature
<222> LOCATION: (7)..(7)
<223> OTHER INFORMATION: 5-pyrene-deoxyuridine
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (30)..(30)
<223> OTHER INFORMATION: T-propanol

<400> SEQUENCE: 90
ttttnttntt tttttttttt tttttttttt                                30

<210> SEQ ID NO 91
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (5)..(10)
<223> OTHER INFORMATION: thymidine methylphosphonate
<220> FEATURE:
<221> NAME/KEY: misc_feature
<222> LOCATION: (30)..(30)
<223> OTHER INFORMATION: T-propanol

<400> SEQUENCE: 91
ttttnnnnnn tttttttttt tttttttttt                                30

<210> SEQ ID NO 92
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (5)..(10)
<223> OTHER INFORMATION: pyrrolidine
<220> FEATURE:
<221> NAME/KEY: misc_feature

```
<222> LOCATION: (30)..(30)
<223> OTHER INFORMATION: T-propanol

<400> SEQUENCE: 92
ttttnnnnnt tttttttttt tttttttttt                                30

<210> SEQ ID NO 93
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-pyrrolidine-phosphate-T
<220> FEATURE:
<221> NAME/KEY: misc_feature
<222> LOCATION: (30)..(30)
<223> OTHER INFORMATION: T-propanol

<400> SEQUENCE: 93
tttttttttt tttttttttt tttttttttt                                30

<210> SEQ ID NO 94
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-pyrrolidine-phosphate-pyrrolidine-phosphate-
      T
<220> FEATURE:
<221> NAME/KEY: misc_feature
<222> LOCATION: (30)..(30)
<223> OTHER INFORMATION: T-propanol

<400> SEQUENCE: 94
tttttttttt tttttttttt tttttttttt                                30

<210> SEQ ID NO 95
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-pyrrolidine-phosphate-pyrrolidine-phosphate-
      pyrrolidine-phosphate-T
<220> FEATURE:
<221> NAME/KEY: misc_feature
<222> LOCATION: (30)..(30)
<223> OTHER INFORMATION: T-propanol

<400> SEQUENCE: 95
tttttttttt tttttttttt tttttttttt                                30

<210> SEQ ID NO 96
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
```

<223> OTHER INFORMATION: 5'-propyl amidite-cyanine 3-phosphate-T
<220> FEATURE:
<221> NAME/KEY: misc_feature
<222> LOCATION: (30)..(30)
<223> OTHER INFORMATION: T-propanol

<400> SEQUENCE: 96
tttttttttt tttttttttt tttttttttt                                              30

<210> SEQ ID NO 97
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-propyl amidite-propyl amidite-cyanine 3-
      phosphate-T
<220> FEATURE:
<221> NAME/KEY: misc_feature
<222> LOCATION: (30)..(30)
<223> OTHER INFORMATION: T-propanol

<400> SEQUENCE: 97
tttttttttt tttttttttt tttttttttt                                              30

<210> SEQ ID NO 98
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-hexyl amidite-cyanine 3-phosphate-T
<220> FEATURE:
<221> NAME/KEY: misc_feature
<222> LOCATION: (30)..(30)
<223> OTHER INFORMATION: T-propanol

<400> SEQUENCE: 98
tttttttttt tttttttttt tttttttttt                                              30

<210> SEQ ID NO 99
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (5)..(7)
<223> OTHER INFORMATION: alpha anomer of T
<220> FEATURE:
<221> NAME/KEY: misc_feature
<222> LOCATION: (30)..(30)
<223> OTHER INFORMATION: T-propanol

<400> SEQUENCE: 99
tttttttttt tttttttttt tttttttttt                                              30

<210> SEQ ID NO 100
<211> LENGTH: 30
<212> TYPE: DNA

```
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (1)..(29)
<223> OTHER INFORMATION: 3-N-cyanoethyl-dT amidite
<220> FEATURE:
<221> NAME/KEY: misc_feature
<222> LOCATION: (30)..(30)
<223> OTHER INFORMATION: 3-N-cyanoethyl-dT-propanol

<400> SEQUENCE: 100
nnnnnnnnnn nnnnnnnnnn nnnnnnnnnn                                   30

<210> SEQ ID NO 101
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (30)..(30)
<223> OTHER INFORMATION: T-propanol

<400> SEQUENCE: 101
tttttttttt tttttttttt tttttttttt                                   30

<210> SEQ ID NO 102
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (5)..(7)
<223> OTHER INFORMATION: 3-N-cyanoethyl-dT amidite
<220> FEATURE:
<221> NAME/KEY: misc_feature
<222> LOCATION: (30)..(30)
<223> OTHER INFORMATION: T-propanol

<400> SEQUENCE: 102
ttttnnnttt tttttttttt tttttttttt                                   30

<210> SEQ ID NO 103
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (7)..(12)
<223> OTHER INFORMATION: thymidine methylphosphonate
<220> FEATURE:
<221> NAME/KEY: misc_feature
<222> LOCATION: (30)..(30)
<223> OTHER INFORMATION: T-propanol

<400> SEQUENCE: 103
ttttttnnnn nntttttttt tttttttttt                                   30
```

```
<210> SEQ ID NO 104
<211> LENGTH: 20
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (5)..(5)
<223> OTHER INFORMATION: furan amidite
<220> FEATURE:
<221> NAME/KEY: misc_feature
<222> LOCATION: (7)..(7)
<223> OTHER INFORMATION: furan amidite
<220> FEATURE:
<221> NAME/KEY: misc_feature
<222> LOCATION: (9)..(9)
<223> OTHER INFORMATION: furan amidite
<220> FEATURE:
<221> NAME/KEY: misc_feature
<222> LOCATION: (11)..(11)
<223> OTHER INFORMATION: furan amidite
<220> FEATURE:
<221> NAME/KEY: misc_feature
<222> LOCATION: (20)..(20)
<223> OTHER INFORMATION: T-propanol

<400> SEQUENCE: 104
ttttntntnt nttttttttt                                        20

<210> SEQ ID NO 105
<211> LENGTH: 20
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (20)..(20)
<223> OTHER INFORMATION: T-propanol

<400> SEQUENCE: 105
tttttttttt tttttttttt                                        20

<210> SEQ ID NO 106
<211> LENGTH: 20
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (5)..(7)
<223> OTHER INFORMATION: 3-N-cyanoethyl-dT amidite
<220> FEATURE:
<221> NAME/KEY: misc_feature
<222> LOCATION: (20)..(20)
<223> OTHER INFORMATION: T-propanol

<400> SEQUENCE: 106
ttttnnnttt tttttttttt                                        20

<210> SEQ ID NO 107
<211> LENGTH: 20
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (7)..(12)
```

```
<223> OTHER INFORMATION: thymidine methylphosphonate
<220> FEATURE:
<221> NAME/KEY: misc_feature
<222> LOCATION: (20)..(20)
<223> OTHER INFORMATION: T-propanol

<400> SEQUENCE: 107
ttttttnnnn nntttttttt                                                     20

<210> SEQ ID NO 108
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(1)
<223> OTHER INFORMATION: 5'-cyanine 3-phosphate-T
<220> FEATURE:
<221> NAME/KEY: misc_feature
<222> LOCATION: (6)..(6)
<223> OTHER INFORMATION: bis-hydroxyethylbenzene
<220> FEATURE:
<221> NAME/KEY: misc_feature
<222> LOCATION: (30)..(30)
<223> OTHER INFORMATION: T-propanol

<400> SEQUENCE: 108
tttttntttt tttttttttt tttttttttt                                          30

<210> SEQ ID NO 109
<211> LENGTH: 20
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (6)..(6)
<223> OTHER INFORMATION: bis-hydroxyethylbenzene
<220> FEATURE:
<221> NAME/KEY: misc_feature
<222> LOCATION: (20)..(20)
<223> OTHER INFORMATION: T-propanol

<400> SEQUENCE: 109
tttttntttt tttttttttt                                                     20

<210> SEQ ID NO 110
<211> LENGTH: 69
<212> TYPE: PRT
<213> ORGANISM: Artificial Sequence
<220> FEATURE:
<223> OTHER INFORMATION: artificial

<400> SEQUENCE: 110
```

Glu Ala Ala Ala Glu Ala Ala Ala Glu Ala Ala Ala Glu Ala Ala Ala
1               5                   10                  15

Glu Ala Ala Ala Glu Ala Ala Ala Glu Ala Ala Ala Glu Ala Ala Ala
            20                  25                  30

Glu Ala Ala Ala Glu Ala Ala Ala Glu Ala Ala Ala Glu Ala Ala Ala
        35                  40                  45

Glu Ala Ala Ala Glu Ala Ala Ala Glu Ala Ala Ala Glu Ala Ala Ala
    50                  55                  60

Glu Glu Glu Glu Glu
65

<210> SEQ ID NO 111
<211> LENGTH: 57
<212> TYPE: PRT
<213> ORGANISM: Artificial Sequence
<220> FEATURE:
<223> OTHER INFORMATION: Synthetic peptide

<400> SEQUENCE: 111

Glu Ala Ala Ala Glu Ala Ala Ala Glu Ala Ala Ala Glu Ala Ala Ala
1               5                   10                  15

Glu Ala Ala Ala Glu Ala Ala Ala Glu Ala Ala Ala Glu Ala Ala Ala
            20                  25                  30

Glu Ala Ala Ala Glu Ala Ala Ala Glu Ala Ala Ala Glu Ala Ala Ala
        35                  40                  45

Glu Ala Ala Ala Glu Glu Glu Glu Glu
    50                  55

<210> SEQ ID NO 112
<211> LENGTH: 45
<212> TYPE: PRT
<213> ORGANISM: Artificial Sequence
<220> FEATURE:
<223> OTHER INFORMATION: synthetic peptide

<400> SEQUENCE: 112

Glu Ala Ala Ala Glu Ala Ala Ala Glu Ala Ala Ala Glu Ala Ala Ala
1               5                   10                  15

Glu Ala Ala Ala Glu Ala Ala Ala Glu Ala Ala Ala Glu Ala Ala Ala
            20                  25                  30

Glu Ala Ala Ala Glu Ala Ala Ala Glu Glu Glu Glu Glu
        35                  40                  45

<210> SEQ ID NO 113
<211> LENGTH: 69
<212> TYPE: PRT
<213> ORGANISM: Artificial Sequence
<220> FEATURE:
<223> OTHER INFORMATION: synthetic peptide

<400> SEQUENCE: 113

Glu Ala Ala Ala Glu Ala Ala Ala Glu Ala Ala Ala Glu Ala Ala Ala
1               5                   10                  15

Glu Ala Ala Ala Glu Ala Ala Ala Glu Ala Ala Ala Glu Ala Ala Ala
            20                  25                  30

Glu Ala Ala Ala Glu Ala Ala Ala Glu Ala Ala Ala Glu Ala Ala Ala
        35                  40                  45

Glu Ala Ala Ala Glu Ala Ala Ala Glu Ala Ala Ala Glu Ala Ala Ala
    50                  55                  60

Gly Gly Gly Gly Glu
65

<210> SEQ ID NO 114
<211> LENGTH: 50
<212> TYPE: PRT
<213> ORGANISM: Artificial Sequence
<220> FEATURE:
<223> OTHER INFORMATION: synthetic peptide

<400> SEQUENCE: 114

Ala Glu Ala Glu Ala Glu Ala Glu Ala Glu Ala Glu Ala Glu Ala Glu
1               5                   10                  15

Ala Glu Ala Glu Ala Glu Ala Glu Ala Glu Ala Glu Ala Glu
            20                  25                  30

Ala Glu Ala Glu Ala Glu Ala Glu Ala Glu Ala Glu Ala Glu
        35                  40                  45

Ala Glu
    50

<210> SEQ ID NO 115
<211> LENGTH: 70
<212> TYPE: PRT
<213> ORGANISM: Artificial Sequence
<220> FEATURE:
<223> OTHER INFORMATION: synthetic peptide

<400> SEQUENCE: 115

Glu Ala Ala Ala Glu Ala Ala Ala Glu Ala Ala Ala Glu Ala Ala Ala
1               5                   10                  15

Glu Ala Ala Ala Glu Ala Ala Ala Glu Ala Ala Ala Glu Ala Ala Ala
            20                  25                  30

Pro Glu Ala Ala Ala Glu Ala Ala Ala Glu Ala Ala Ala Glu Ala Ala
        35                  40                  45

Ala Glu Ala Ala Ala Glu Ala Ala Ala Glu Ala Ala Ala Glu Ala Ala
    50                  55                  60

Ala Glu Glu Glu Glu Glu
65                  70

<210> SEQ ID NO 116
<211> LENGTH: 72
<212> TYPE: PRT
<213> ORGANISM: Artificial Sequence
<220> FEATURE:
<223> OTHER INFORMATION: synthetic peptide

<400> SEQUENCE: 116

Glu Ala Ala Ala Glu Ala Ala Ala Glu Ala Ala Ala Glu Ala Ala Ala
1               5                   10                  15

Pro Glu Ala Ala Ala Glu Ala Ala Ala Glu Ala Ala Ala Glu Ala Ala
            20                  25                  30

Ala Pro Glu Ala Ala Ala Glu Ala Ala Ala Glu Ala Ala Ala Glu Ala
        35                  40                  45

Ala Ala Pro Glu Ala Ala Ala Glu Ala Ala Ala Glu Ala Ala Ala Glu
    50                  55                  60

Ala Ala Ala Glu Glu Glu Glu Glu
65                  70

<210> SEQ ID NO 117
<211> LENGTH: 69
<212> TYPE: PRT
<213> ORGANISM: Artificial Sequence
<220> FEATURE:
<223> OTHER INFORMATION: synthetic peptide

<400> SEQUENCE: 117

Glu Ala Ala Ala Lys Ala Ala Ala Glu Ala Ala Ala Lys Ala Ala Ala
1               5                   10                  15

Glu Ala Ala Ala Lys Ala Ala Ala Glu Ala Ala Ala Lys Ala Ala Ala
            20                  25                  30

Glu Ala Ala Ala Glu Ala Ala Ala Glu Ala Ala Ala Glu Ala Ala Ala
        35                  40                  45

Glu Ala Ala Ala Glu Ala Ala Ala Glu Ala Ala Ala Glu Ala Ala Ala 50                  55                  60

Glu Glu Glu Glu Glu
 65

<210> SEQ ID NO 118
<211> LENGTH: 69
<212> TYPE: PRT
<213> ORGANISM: Artificial Sequence
<220> FEATURE:
<223> OTHER INFORMATION: synthetic peptide

<400> SEQUENCE: 118

Glu Ala Ala Ala Lys Ala Ala Ala Glu Ala Ala Ala Lys Ala Ala Ala
 1               5                  10                  15

Glu Ala Ala Ala Lys Ala Ala Ala Glu Ala Ala Ala Lys Ala Ala Ala
             20                  25                  30

Glu Ala Ala Ala Lys Ala Ala Ala Glu Ala Ala Ala Lys Ala Ala Ala
         35                  40                  45

Glu Ala Ala Ala Lys Ala Ala Ala Glu Ala Ala Ala Lys Ala Ala Ala
     50                  55                  60

Glu Glu Glu Glu Glu
 65

<210> SEQ ID NO 119
<211> LENGTH: 55
<212> TYPE: PRT
<213> ORGANISM: Artificial Sequence
<220> FEATURE:
<223> OTHER INFORMATION: synthetic peptide

<400> SEQUENCE: 119

Glu Pro Pro Pro Pro Pro Pro Pro Glu Pro Pro Pro Pro Pro Pro Pro
 1               5                  10                  15

Pro Pro Pro Pro Glu Pro Pro Pro Pro Pro Pro Pro Glu Pro Pro Pro
             20                  25                  30

Pro Pro Pro Pro Pro Pro Pro Glu Pro Pro Pro Pro Pro Pro Pro Pro
         35                  40                  45

Pro Pro Glu Glu Glu Glu Glu
     50                  55

<210> SEQ ID NO 120
<211> LENGTH: 69
<212> TYPE: PRT
<213> ORGANISM: Artificial Sequence
<220> FEATURE:
<223> OTHER INFORMATION: synthetic peptide

<400> SEQUENCE: 120

Glu Pro Pro Pro Glu Pro Pro Pro Glu Pro Pro Pro Glu Pro Pro Pro
 1               5                  10                  15

Glu Pro Pro Pro Glu Pro Pro Pro Glu Pro Pro Pro Glu Pro Pro Pro
             20                  25                  30

Glu Pro Pro Pro Glu Pro Pro Pro Glu Pro Pro Pro Glu Pro Pro Pro
         35                  40                  45

Glu Pro Pro Pro Glu Pro Pro Pro Glu Pro Pro Pro Glu Pro Pro Pro
     50                  55                  60

Glu Glu Glu Glu Glu
 65

<210> SEQ ID NO 121

```
<211> LENGTH: 50
<212> TYPE: PRT
<213> ORGANISM: Artificial Sequence
<220> FEATURE:
<223> OTHER INFORMATION: synthetic peptide

<400> SEQUENCE: 121

Pro Pro Pro Pro Pro Pro Pro Pro Pro Pro Pro Pro Pro Pro Pro
1               5                   10                  15

Pro Pro Pro Pro Pro Pro Pro Pro Pro Pro Pro Pro Pro Pro Pro
            20                  25                  30

Pro Pro Pro Pro Pro Pro Pro Pro Pro Pro Pro Glu Glu Glu
        35                  40                  45

Glu Glu
    50

<210> SEQ ID NO 122
<211> LENGTH: 69
<212> TYPE: PRT
<213> ORGANISM: Artificial Sequence
<220> FEATURE:
<223> OTHER INFORMATION: synthetic peptide

<400> SEQUENCE: 122

Arg Ala Ala Ala Arg Ala Ala Ala Arg Ala Ala Ala Arg Ala Ala
1               5                   10                  15

Arg Ala Ala Ala Arg Ala Ala Ala Arg Ala Ala Ala Arg Ala Ala
            20                  25                  30

Arg Ala Ala Ala Arg Ala Ala Ala Arg Ala Ala Ala Arg Ala Ala
        35                  40                  45

Arg Ala Ala Ala Arg Ala Ala Ala Arg Ala Ala Ala Arg Ala Ala
    50                  55                  60

Arg Arg Arg Arg Arg
65

<210> SEQ ID NO 123
<211> LENGTH: 69
<212> TYPE: PRT
<213> ORGANISM: Artificial Sequence
<220> FEATURE:
<223> OTHER INFORMATION: synthetic peptide

<400> SEQUENCE: 123

Glu Ala Thr Ala Glu Ala Thr Ala Glu Ala Thr Ala Glu Ala Thr Ala
1               5                   10                  15

Glu Ala Thr Ala Glu Ala Thr Ala Glu Ala Thr Ala Glu Ala Thr Ala
            20                  25                  30

Glu Ala Thr Ala Glu Ala Thr Ala Glu Ala Thr Ala Glu Ala Thr Ala
        35                  40                  45

Glu Ala Thr Ala Glu Ala Thr Ala Glu Ala Thr Ala Glu Ala Thr Ala
    50                  55                  60

Glu Glu Glu Glu Glu
65

<210> SEQ ID NO 124
<211> LENGTH: 76
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
```

```
<222> LOCATION: (1)..(1)
<223> OTHER INFORMATION: 5'-Cyanine-5 3-phosphate-A
<220> FEATURE:
<221> NAME/KEY: misc_feature
<222> LOCATION: (62)..(62)
<223> OTHER INFORMATION: propyl amidite

<400> SEQUENCE: 124
agagtgatag tatgattatg tagatgtagg atttgatatg tgagtagccg aatgaaacct    60
tnttggtttc attcgg                                                    76

<210> SEQ ID NO 125
<211> LENGTH: 24
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (24)..(24)
<223> OTHER INFORMATION: 3'-BHQ-T
<220> FEATURE:
<221> NAME/KEY: misc_feature
<222> LOCATION: (24)..(24)
<223> OTHER INFORMATION: T-3'-BHQ-2

<400> SEQUENCE: 125
ttttcataat catactatca ctct                                           24

<210> SEQ ID NO 126
<211> LENGTH: 154
<212> TYPE: DNA
<213> ORGANISM: Artificial Sequence
<220> FEATURE:
<223> OTHER INFORMATION: synthesized oligonucleotide

<400> SEQUENCE: 126
cgattacttt agttttcgtt tttactactg actgtcctcc tcctccgtta ttgtaaaaac    60
gaaaactaaa gtaatcgcga ttactttagt tttcgttttt actactgact gtcctcctcc   120
tccgttattg taaaaacgaa aactaaagta atcg                               154
```